US009677098B2

(12) United States Patent
Lee et al.

(10) Patent No.: US 9,677,098 B2
(45) Date of Patent: Jun. 13, 2017

(54) YEAST CELL-PRODUCING LACTATE WITH REDUCED ACTIVITY OF RIM15 AND IGO2, METHOD OF PRODUCING THE YEAST CELL, AND METHOD OF PRODUCING LACTATE BY USING THE YEAST CELL

(71) Applicant: Samsung Electronics Co., Ltd., Suwon-si, Gyeonggi-do (KR)

(72) Inventors: Juyoung Lee, Daegu (KR); Changduk Kang, Gwacheon-si (KR); Jiyoon Song, Seoul (KR); Seunghyun Lee, Asan-si (KR); Jinhwan Park, Suwon-si (KR); Kwangmyung Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 47 days.

(21) Appl. No.: 14/808,556

(22) Filed: Jul. 24, 2015

(65) Prior Publication Data

US 2016/0177347 A1 Jun. 23, 2016

(30) Foreign Application Priority Data

Dec. 18, 2014 (KR) ........................ 10-2014-0183303

(51) Int. Cl.
*C12P 7/56* (2006.01)
*C12N 9/12* (2006.01)
*C12N 9/04* (2006.01)
*C07K 14/395* (2006.01)

(52) U.S. Cl.
CPC .............. *C12P 7/56* (2013.01); *C07K 14/395* (2013.01); *C12N 9/0006* (2013.01); *C12N 9/1205* (2013.01); *C12Y 101/01027* (2013.01); *C12Y 101/01028* (2013.01)

(58) Field of Classification Search
CPC ................. C07K 14/395; C12Y 101/01027
USPC ........................................................ 435/139
See application file for complete search history.

(56) References Cited

U.S. PATENT DOCUMENTS

2003/0044946 A1 3/2003 Longo
2014/0220647 A1 8/2014 Kim et al.

FOREIGN PATENT DOCUMENTS

| EP | 2826857 A1 | 1/2015 |
|---|---|---|
| JP | 2014-039533 A | 3/2006 |
| JP | 2013-169198 A | 2/2012 |
| JP | 2012-191885 A | 10/2012 |
| KR | 2001-0032245 A | 4/2001 |
| WO | WO 2007/117282 A2 | 10/2007 |
| WO | WO 2012/055996 A1 | 5/2012 |

OTHER PUBLICATIONS

Abbott et al.,"Metabolic engineering of *Saccharomyces cerevisiae* for production of carboxylic acids: current status and challenges", *FEMS Yeast Res.*, 9: 1123-1136 (2009).
Ookubo et al., "Improvement of L-Lactate Production by *CYB2* Gene Disruption in a Recombinant *Saccharomyces cerevisiae* Strain under Low pH condition", *Biosci. Biotechnol. Biochem.*, 72(11):3063-3066 (2008).
Song et al., "Introduction of a bacterial acetyl-CoA synthesis pathway improves lactic acid production in *Saccharomyces cerevisiae*", *Metabolic Engineering*, 35:38-45 (2015).
Database UniProt online, Nov. 1, 1995, RecName: Full=Serine/threonine-protein kinase RIM15; EC=2.7.11.1, XP002756609, retrieved from EBI accession No. UNIPROT: P43565, Database accession No. P43565.
Database UniProt online, Jul. 11, 2006, RecName: Full=mRNA stability protein IG02; AltName: Full=Initiation of G zero protein 2; XP002756610, retrieved from EBI accession No. UNIPROT: Q9P305, Database accession No. Q9P305.
European Patent Office, Extended European Search Report for Application No. 15188701.5, dated Apr. 28, 2016, 10 pp.
Bisschops et al., "To divide or not to divide: A key role of Rim15 in calorie-restricted yeast cultures", *Biochimica et Biophysica Acta*, 1843: 1020-1030 (2014).
Chae et al., "A route to high surface area, porosity and inclusion of large molecules in crystals", *Nature*, 42:523-527 (2004).
Chen et al., "Greatly enhanced mechanical properties and heat distortion resistance of poly(L-lactic acid) upon compositing with functionalized reduced grapheme oxide†", *Journal of Materials Chemistry*, 1:9028-9032 (2013).
Lee et al., "Measurement of the Elastic Properties and Intrinsic Strength of Monolayer Graphene", *Science*, 321: 385-388 (2008).
Li et al., "Preparation of Polylactide/Graphene Composites From Liquid-Phase Exfoliated Graphite Sheets", *Polymer Composites*, pp. 396-403 (2014).
Potts et al., "Graphene-based polymer nanocomposites", *Polymer*, 52: 5-25 (2011).
Stankovich et al., "Synthesis of graphene-based nanosheets via chemical reduction of exfoliated graphite oxide", *Carbon*, 45: 1558-1565 (2007).
Sun et al., "Synthesis and Stereocomplex Crystallization of Poly(lactide)—Graphene Oxide Nanocomposites", *ACS Macro Letters*, 1: 709-713 (2012).
Wan et al., "Reinforcement and interphase of polymer/graphene oxide nanocomposites", *Journal of Materials Chemistry*, 22: 3637-3646 (2012).
Wang et al., "Crystallization kinetics and morphology of biodegradable poly(l-lactic acid)/graphene oxide nanocomposites: Influences of graphene oxide loading and crystallization temperature", *Thermochimica Acta*, 527: 40-46 (2012).

(Continued)

*Primary Examiner* — Tekchand Saidha
(74) *Attorney, Agent, or Firm* — Leydig, Voit & Mayer, Ltd.

(57) ABSTRACT

A yeast cell capable of producing lactate, a method of preparing the yeast cell, and a method of producing lactate by using the yeast cell, wherein theyeast cell has a reduced activity of rim15 protein, igo2 protein, or a combination thereof, and an increased activity of an enzyme that catalyzes conversion from pyruvate to lactate, compared to a parent cell.

19 Claims, 3 Drawing Sheets

(56) References Cited

OTHER PUBLICATIONS

Xu et al., "In situ Polymerization Approach to Graphene-Reinforced Nylon-6 Composites", *Macromolecules*, 43:6716-6723 (2010).
Yan et al., "Structural characteristics and thermal properties of plasticized poly(L-lactide)-silica nanocomposites synthesized by sol-gel method", *Materials Letters*, 61: 2683-2686 (2007).
Yang et al., Preparation and characterization of poly(L-lactide)—graphene composites using the in situ ring-opening polymerization of PLLA with graphene as the initiator†, *Journal of Materials Chemistry*, 22:10805-10815 (2012).

YEAST CELL-PRODUCING LACTATE WITH REDUCED ACTIVITY OF RIM15 AND IGO2, METHOD OF PRODUCING THE YEAST CELL, AND METHOD OF PRODUCING LACTATE BY USING THE YEAST CELL

RELATED APPLICATIONS

This application claims the benefit of Korean Patent Application No. 10-2014-0183303, filed on Dec. 18, 2014, in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 143,685 Byte ASCII (Text) file named "720717_ST25.TXT," created on Jul. 14, 2015.

BACKGROUND

1. Field

The present disclosure relates to a yeast cell capable of producing lactate, a method of preparing the same, and a method of producing lactate using the yeast cell.

2. Description of the Related Art

Lactate is an organic acid which is widely used in various industrial fields such as food, pharmaceutical, chemical, and electronic industries. Lactate is a colorless, odorless, and highly water-soluble substance having low volatility. As lactate is nontoxic to the human body, lactate is used as a flavoring agent, an acidifier, and a preservative. In addition, lactate is a raw material of polylactic acid (PLA), which is an environment-friendly alternative polymer substance and a biodegradable plastic. Technologically, PLA is a polyester resin formed by converting lactate into lactide, which is a dimer, for polymerization, and performing a ring-open polymerization with the lactide. PLA may be processed into various forms such as a film, a sheet, a fiber, and an injection molding product. Therefore, as PLA is a bio-plastic which may extensively be substituted for conventional general-purpose petrochemical plastics such as polyethylene (PE), polypropylene (PP), polyethylene terephthalate (PET), and polystyrene (PS), the demand for PLA has greatly increased in recent times. In addition, lactate has both a hydroxyl group and a carboxyl group and thus is highly reactive. Thus, lactate may be easily converted to industrially important compounds such as ester of lactate, acetaldehyde, and propylene glycol. Therefore, lactate is drawing attention in the field of chemical engineering as a next-generation alternative chemical raw material.

At present, lactate is industrially produced by a petrochemical synthetic process and a biological fermentative process. In the petrochemical synthetic process, lactate is prepared by oxidizing ethylene derived from crude oil, converting the resulting acetaldehyde into lactonitrile by an addition reaction of hydrogen cyanide, purifying the resulting lactonitrile by distillation, and hydrolyzing the purified lactonitrile by using hydrochloric acid or sulfuric acid. In the biological fermentative process, lactate may be prepared by using assimilable carbohydrates such as starch, sucrose, maltose, glucose, fructose, and xylose as substrates for microbial fermentation to produce lactate. Therefore, despite the existence of these conventional technologies, a microbial strain capable of efficiently producing lactate and a method of producing lactate by using the same are still needed. In accordance with the need, a method of producing lactate by using a microorganism, such as yeast, has been recently developed. However, due to homeostasis of the microorganism, it is difficult for the microorganism to produce only one substance in large quantities.

Thus, there remains a need for yeast cells with increased lactate production capability.

SUMMARY

Provided is a recombinant yeast cell capable of efficiently producing lactate. The recombinant yeast cell comprises a genetic modification that reduces the activity of rim15 protein, igo2 protein, or any combination thereof, as compared to a parent yeast cell; and further comprising a genetic modification that increases the activity of an enzyme that catalyzes the conversion from pyruvate into lactate as compared to a parent yeast cell.

Also provided is a method of producing a recombinant yeast cell capable of efficiently producing lactate, the method comprising introducing into a yeast cell a gene that encodes an enzyme catalyzing conversion from pyruvate to lactate; and disrupting in the yeast cell a gene that encodes rim15 protein, a gene that encodes igo2 protein, or both a gene that encodes rim15 protein and a gene that encodes igo2 protein.

Further provided is a method of producing lactate by using the recombinant yeast cell.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
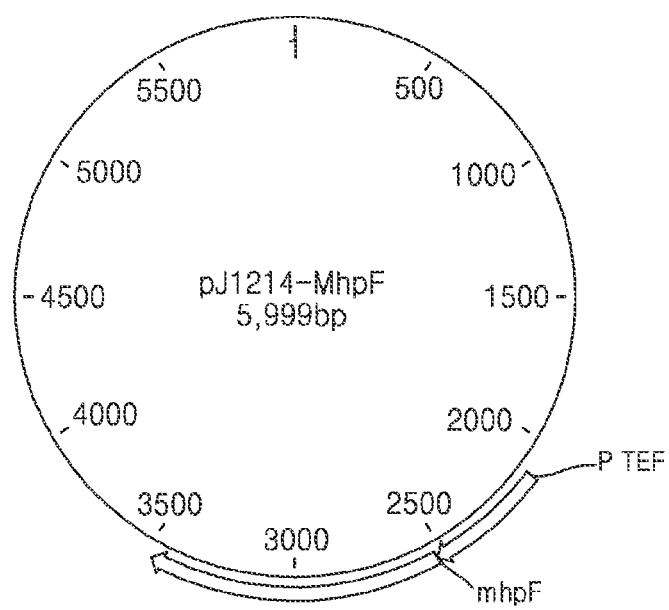
FIG. 1 is a map of pJ1214-MhpF vector.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The terms "increase in activity", or "increased activity" or the like used herein may refer to a detectable increase in activity of a cell, a protein, or an enzyme. The terms "increase in activity", or "increased activity" used herein may mean that a modified (for example, genetically engineered) cell, protein, or enzyme shows higher activity than a comparable cell, protein, or enzyme of the same type, like a cell, a protein, or an enzyme that does not have a particular genetic modification (for example, a parent or "wild-type" cell, protein, or enzyme). For example, activity of a modified or engineered cell, protein, or enzyme may be higher than activity of a non-engineered cell, protein, or enzyme of the same type, for example, a wild-type or parent cell, protein, or enzyme by about 5% or more, about 10% or more, about 15% or more, about 20% or more, about 30% or more, about 50% or more, about 60% or more, about 70% or more, or about 100% or more. The activity of a particular protein or enzyme in a recombinant or engineered cell may be higher than the activity of a protein or enzyme of the same type in a parent cell, for example, a non-engineered cell by about 5% or more, about 10% or more, about 15% or more, about 20% or more, about 30% or more, about 50% or more, about 60% or more, about 70% or more, or about 100% or more. Increased activity of an enzyme or protein in a cell may be verified by any methods known in the art. The cell with increased activity may have, compared to a cell that does not have a genetic modification, one or more genetic modifications that increase an activity of an enzyme or a polypeptide. The term "a recombinant cell" used herein is interchangeably used with the term"an engineered cell".

The terms "decrease in activity" or "decreased activity" or the like used herein include a case in which a cell contains an enzyme or polypeptide, of which activity is lower than that in a parent cell (for example, a cell that is not genetically engineered). Also, the terms "decrease in activity" or "decrease in activity" include a case in which activity of separated enzyme or polypeptide is lower than that of parent or wild-type enzyme or polypeptide. The terms "decrease in activity" or "decreased activity" include a cell, enzyme, or polypeptide exhibiting no activity. For example, an enzyme conversion activity of a modified (for example, genetically engineered) cell or enzyme from a substrate to a product is lower than an enzyme conversion activity of non-modified cell or enzyme, for example, a parent cell or "wild-type" cell or enzyme by about 20% or more, about 30% or more, about 40% or more, about 50% or more, about 55% or more, about 60% or more, about 70% or more, about 75% or more, about 80% or more, about 85% or more, about 90% or more, about 95% or more, or about 100%. The decrease in activity in an enzyme or a cell may be verified by using any methods that are known in the art. The decrease in activity includes a case in which a gene encoding the enzyme is expressed, yet compared to a cell expressing an unmodified enzyme, for example, a parent cell or a wild-type cell, the enzyme may have no activity or decreased activity (e.g., a genetic modification resulting in a partially or completely defective enzyme or protein). The decrease in activity also includes a case in which expression of a gene encoding an enzyme is decreased or eliminated in a modified cell compared to a cell without a particular genetic modification, for example, a parent cell or a wild-type cell (e.g., a genetic modification that decreases or eliminates expression of an enzyme or protein, resulting in lower amounts of the enzyme or protein). The cell with decreased activity may have, compared to a cell that does not have a genetic modification, one or more genetic modifications that decrease the activity of an enzyme or a polypeptide.

The term "parent cell" used herein refers to an original cell, for example, in the case of an engineered yeast cell, a yeast cell before being genetically engineered in a particular manner. Regarding a particular genetic modification, the "parent cell" is a cell that does not have the particular genetic modification. However, in other aspects, the parent cell may be identical to a genetically engineered cell of the same type. Accordingly, the parent cell may be a cell that is used as a starting material for the production of a genetically engineered yeast cell.

The terms "disruption", "disrupted", and the like used herein refer to reduced expression of a given gene due to a genetic modification. Disruption can be caused by a genetic modification that completely nullifies expression of a referenced gene (hereinafter, referred to as "inactivation" of a gene.). Disruption also includes a genetic modification that causes expression of a gene at decreased levels without completely nullifying expression (hereinafter, referred to as "attenuation" of a gene.). Expression, in this sense, refers to transcription of a gene product as well as translation of an active gene product. Thus, inactivation includes a case in which a gene is not transcribed or translated, such that the product of a gene is not expressed, and a case in which, although a gene is transcribed and translated, the gene product is not functional. Similarly, attenuation includes a case in which transcription and/or translation of a gene is reduced, as well as a case in which transcription and/or translation is not reduced, but the gene product has a lower activity level. Herein, the term "a functional product of a gene" means that the gene product (e.g., protein or enzyme) has a biochemical or physiologic function (for example, enzyme activity). The disruption of the gene includes a functional disruption of the gene, wherein the biochemical or physiologic function in a genetically modified cell is reduced or completely nullified in comparison to a parent or wild-type cell.

Genetic modification includes a modification that introduces a polynucleotide encoding a polypeptide into a cell; a modification that substitutes, adds (i.e., inserts), or deletes one or more nucleotides of the genetic material of a parent cell, including a chemical modification (exposure to a chemical) resulting in a change to the genetic material of a parent cell. Genetic modification includes a heterologous or homologous modification of referenced species. Genetic modification includes a modification of a coding region for polypeptides. Genetic modification also includes a modification of non-coding regulatory regions that change expression of a gene or function of an operon. Non-coding regions include 5'-non-coding sequence (5' of a coding sequence) and 3'-non-coding sequence (3' of a coding sequence).

The disruption of a gene may be achieved by a genetic engineering method, such as homologous recombination, directed mutagenesis, or directed molecular evolution. When a cell includes a plurality of identical genes or 2 or more paralogs of a gene, one or more genes may be disrupted. For example, the genetic modification may involve transforming a cell with a vector including the sequence of a gene, and then culturing the cell to cause a homologous recombination of the exogenous nucleic acid and an endogenous gene of the cell, thereby disrupting the endogenous gene. The cell that has undergone homologous recombination can be screened out (selected) by using a selective marker.

The "gene" used herein refers to a nucleic acid fragment that encodes a particular protein, which may optionally include at least one regulatory sequence, such as a 5'-non-coding sequence and a 3'-non-coding sequence (3' and 5' in reference to the position relative to the coding sequence).

The term "sequence identity" of a nucleic acid or polypeptide used herein refers to a degree of identity of bases or amino acid residues of two corresponding sequences over a particular region measured after the sequences are aligned to be matched with each other as much as possible. The sequence identity is a value that is measured by comparing two optimally aligned corresponding sequences of a particular comparable region, wherein in the comparable region, a part of the sequence may be added or deleted compared to a reference sequence. In some embodiments, a percentage of the sequence identity may be calculated by comparing two optimally aligned corresponding sequences in an entire comparable region, determining the number of locations where an amino acid or a nucleic acid is identical in the two sequences to obtain the number of matched locations, dividing the number of the matched locations by the total number (that is, a range size) of all locations within a comparable range, and multiplying the result by 100 to obtain a percentage of the sequence identity. The percent of the sequence identity may be determined by using known sequence comparison programs, examples of which include BLASTN and BLASTP (NCBI), CLC Main Workbench (CLC bio.), MegAlign™ (DNASTAR Inc).

In identifying polypeptides or polynucleotides of different species that may have identical or similar function or activity, similarity in sequence identity may be used. For example, similar sequences may have a sequence identity of 50% or more, 55% or more, 60% or more, 65% or more, 70% or more, 75% or more, 80% or more, 85% or more, 90% or more, 95% or more, 96% or more, 97% or more, 98% or more, 99% or more, or 100%.

The term "exogenous" and the like used herein refers to a referenced molecule (e.g., nucleic acid) or referenced activity that has been introduced into a host cell. A nucleic acid may be exogenously introduced into a host in any suitable manner. For example, a nucleic acid can be introduced into a host cell and inserted into a host chromosome, or the nucleic acid can be introduced into the host as non-chromosomal genetic material, such as an expression vector (e.g., a plasmid) that does not integrate into the host chromosome. A nucleic acid encoding a protein should be introduced in an expressionable form (i.e., so that the nucleic acid can be transcribed and translated). An exogenous "activity" (e.g., biosynthesis activity) refers to an activity introduced into a host parent cell, such as by introducing one or more nucleic acids to the host that are expressed to provide the activity.

The term "endogenous" refers to a referenced molecule (e.g., nucleic acid) or activity already present in the host cell prior to a particular genetic modification (e.g., a genetic composition, trait, or biosynthetic activity of a "wild-type" cell or a parent cell).

The term "heterologous" refers to molecule (e.g., nucleic acid) or activity derived from a source other than referenced species; and the term "homologous" refers to a molecule (e.g., nucleic acid) or activity derived from a host parent cell. Accordingly, an exogenous molecule or activity (e.g., expression of an exogenous coding nucleic acid) may be heterologous (e.g., a coding nucleic acid from a different species) or homologous (e.g., an additional copy of a coding nucleic acid from the same species).

The term "genetic engineering" used herein refers to an act of introducing one or more genetic modifications into a cell, and the term "genetically engineered" refers to a protein or enzyme that has a non-naturally occurring sequence or a cell having a non-natural genetic composition.

The term "lactate" used herein refers to a lactic acid or a salt thereof.

In an aspect of the present disclosure, there is provided a recombinant yeast cell capable of producing lactate, the yeast cell having a reduced activity of rim15 protein, igo2 protein, or a combination thereof and an increased activity of an enzyme catalyzing conversion from pyruvate into lactate, compared to those of a parent cell of the yeast cell. The yeast cell comprises a genetic modification to reduce the activity of rim15 protein, igo2 protein, or a combination thereof, and a genetic modification to increase the activity of the enzyme catalyzing the conversion from pyruvate into lactate.

In the yeast cell, rim15 protein may be a glucose-repressible protein kinase that is involved in signal transduction during cell proliferation in response to nutrients, especially during the establishment of stationary phase. Rim15 protein, which is primarily identified as a regulator of IME2, may also be involved in phosphorylation of Igo1p and Igo2. Rim15 may be an enzyme of Enzyme Commission (EC) number EC 2.7.11.1 based on the recommendations of the Nomenclature Committee of the International Union of Biochemistry and Molecular Biology (IUBMB). Rim15 protein may be a protein with a 95% or more sequence identity to an amino acid sequence (NP_116620.1) of SEQ ID NO: 1 or a yeast homologue thereof. Rim 15 protein may also be encoded by a nucleotide sequence of SEQ ID NO: 2.

Igo2 protein is a potential protein of unknown function. According to an experimental result obtained with green fluorescent protein (GFP)-fusion protein, Igo2 protein localizes to the cytoplasm and nucleus. Igo2 protein is a protein required for initiation of G0 program and prevents degradation of nutrient-regulated mRNA via the 5'->3' mRNA decay pathway. Igo2 protein is a protein with a 95% or more sequence identity to an amino acid sequence (NP_036194) of SEQ ID NO: 3 or a yeast homologue thereof. Igo2 protein may also be encoded by a nucleotide sequence of SEQ ID NO: 4.

In some embodiments, in the yeast cell, an endogenous gene that encodes rim15 protein, igo2 protein, or a combination thereof may be disrupted. For example, the endogenous gene in the yeast cell may be disrupted to a degree that is sufficient to reduce the activity of rim15 protein, igo2 protein, or a combination thereof to be lower than that in a parent cell of the yeast cell. Disruption can be accomplished by introducing a disruption mutation, such as a complete or partial deletion mutation, of a gene that encodes rim15 protein, igo2 protein, or a combination thereof.

In some embodiments, the enzyme catalyzing the conversion from pyruvate to lactate may be lactate dehydrogenase (LDH) classified as EC 1.1.2.27 or EC 1.1.1.28. LDH may have NAD(P)H-dependency. In some embodiments, LDH may act on D-lactate and/or L-lactate. LDH may have a 95% or more sequence identity to an amino acid sequence of SEQ ID NO: 5. SEQ ID NO: 5 is LDH of *Pelodiscus sinensis japonicus*.

The yeast cell may include an exogenous gene that encodes the enzyme catalyzing the conversion from pyruvate to lactate. A LDH exogenous gene may be, in the yeast cell, expressed in an amount sufficient to increase the activity of the enzyme catalyzing the conversion from pyruvate to lactate. The LDH exogenous gene may encode an amino acid sequence that has a 95% or more sequence identity to an amino acid sequence of SEQ ID NO: 5. The LDH exogenous gene may encode an amino acid sequence that has a 95% or more sequence identity to a nucleotide sequence of SEQ ID NO: 6. The LDH exogenous gene sequence may be changed such that the codons are appropriate for expression in a yeast cell, that is, a sequence having yeast-optimized codons. This codon change may be appropriately made as long as an amino acid sequence of a protein does not change. SEQ ID NO: 6 is a LDH gene of *Pelodiscus sinensis japonicus*.

The LDH exogenous gene may be included in a genome of a cell. The LDH exogenous gene may encode an enzyme that acts on at least one selected from L-lactate and D-lactate. Accordingly, the yeast cell may produce L-lactic acid or D-lactic acid, or a racemic mixture or salt thereof. The LDH exogenous gene may be derived from a bacteria, yeast, a fungus, and an animal, for example, rodents, mammals, amphibian, and Sauropsida. The LDH exogenous gene may be a polynucleotide encoding LDH of one or more species selected from *Pelodiscus sinensis japonicus, Ornithorhynchus anatinus, Tursiops truncatus, Rattus norvegicus,* and *Xenopus laevis. Pelodiscus sinensis japonicus*-derived lactate dehydrogenase, *Ornithorhynchus anatinus*-derived lactate dehydrogenase, *Tursiops truncatus*-derived lactate dehydrogenase, and *Rattus norvegicus*-derived lactate dehydrogenase may have amino acid sequences of SEQ ID NOS: 5, 7, 8, and 9, respectively. The lactate dehydrogenase may have a sequence identity of 75% or more, 80% or more, 85% or more, 90% or more, 95% or more, 96% or more, 97% or more, 98% or more, or 99% or more, or 100%, with respect to the amino acid sequences of SEQ ID NOS: 5, 7, 8, and 9. A gene encoding the lactate dehydrogenase may have a sequence identity of 75% or more, 80% or more, 85% or more, 90% or more, 95% or more, 96% or more, 97% or more, 98% or more, 99% or more, or 100%, with respect to the nucleotide sequences of SEQ ID NO: 6, 10, 11, or 12.

The LDH exogenous gene may be expressed from a vector including the same. The vector may include a replication origin, a promoter, polynucleotide encoding LDH, and a terminator. The replication origin may include a yeast autonomous replication sequence (ARS). The yeast autonomous replication sequence may be stabilized by a yeast centrometric sequence (CEN). The promoter may be selected from the group consisting of a CCW12 promoter, a CYC promoter, a TEF1 promoter, a PGK1 promoter, a GPD promoter, and an ADH promoter. The CCW12 promoter, the CYC promoter, the TEF1 promoter, the PGK1 promoter, the GPD promoter, and the ADH promoter may have nucleotide sequences of SEQ ID NOS: 13, 14, 15, 16, 17, and 18, respectively. The terminator may be selected from the group consisting of PGK1 (phosphoglycerate kinase 1), CYC1 (cytochrome c transcription), and GAL1. The CYC1 terminator may have a nucleotide sequence of SEQ ID NO: 19. The vector may further include a selection marker.

The yeast cell may include a single LDH gene, or a plurality of LDH genes, for example, 2 to 10 copies of LDH gene. The yeast cell may include, for example, 1 to 10, 1 to 8, 1 to 7, 1 to 6, 1 to 5, 1 to 4, 1 to 3, 2 to 10, 2 to 8, 2 to 7, 2 to 6, 2 to 5, 2 to 4, or 2 to 3 copies of LDH gene. When the yeast cell includes a plurality of LDH genes, each gene may include copies of identical gene or two or more different LDH genes. A plurality of copies of exogenous LDH gene may be included in identical gene loci, or various different gene loci in the genome of a host cell.

In some embodiments, the yeast cell may further include a genetic modification to reduce the activity of an enzyme catalyzing the conversion from acetaldehyde to ethanol, and thus may have a reduced activity of the enzyme catalyzing the conversion from acetaldehyde to ethanol.

The enzyme catalyzing the conversion from acetaldehyde into ethanol may be alcohol dehydrogenase (ADH) classified as EC 1.1.1.1. Examples of ADH are ADH1, ADH2, ADH3, ADH4, ADH5, ADH6, and ADH7. The alcohol dehydrogenase may have NADH dependency. ADH1 gene and ADH1 protein may have a nucleotide sequence of SEQ ID NO: 20 and an amino acid sequence of SEQ ID NO: 21, respectively.

In the yeast cell, an endogenous gene that encodes the enzyme catalyzing the conversion from acetaldehyde into ethanol may be disrupted. The endogenous gene in the yeast cell may be disrupted such that an activity of the enzyme catalyzing the conversion from acetaldehyde into ethanol is decreased compared to that of a parent cell thereof.

The yeast cell may be a species classified as any one selected from the group consisting of *Saccharomyces* genus, *Candida* genus, *Schizosaccharomyces* genus, *Kluyveromyces* genus, *Pichia* genus, *Issachenkia* genus, and *Hansenula* genus. A species classified as *Saccharomyces* genus may be, for example, *S. cerevisiae, S. bayanus, S. boulardii, S. bulderi, S. cariocanus, S. cariocus, S. chevaliers, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum,* or *S. zonatus*. A species classified as *Candida* genus may be, for example, *C. albicans, C. ascalaphidarum, C. amphixiae, C. antarctica, C. argentea, C. atlantica, C. atmosphaerica, C. blattae, C. bromeliacearum, C. carpophila, C. carvajalis, C. cerambycidarum, C. chauliodes, C. corydali, C. dosseyi, C. dubliniensis, C. ergatensis, C. fructus, C. glabrata, C. fermentati, C. guilliermondii, C. haemulonii, C. insectamens, C. insectorum, C. intermedia, C. jeffresii, C. kefyr, C. krusei, C. lusitaniae, C. lyxosophila, C. maltosa, C. marina, C. membranifaciens, C. milleri, C. oleophila, C. oregonensis, C. parapsilosis, C. quercitrusa, C. rugosa, C. sake, C. shehatea, C. temnochilae, C. tenuis, C. theae, C. tolerans, C. tropicalis, C. tsuchiyae, C. sinolaborantium, C. sojae, C. subhashii, C. viswanathii, C. utilis,* or *C. ubatubensis*. A species classified as *Schizosaccharomyces* genus may be, for example, *S. pombe, S. japonicus, S. octosporus,* or *S. cryophilus*. A species classified as *Kluyveromyces* genus may be, for example, *K. aestuarii, K. africanus, K. bacillisporus, K. blattae, K. dobzhanskii, K. hubeiensis, K. lactis, K. lodderae, K. marxianus, K. nonfermentans, K. piceae, K. sinensis, K. thermotolerans, K. waltii, K. wickerhamii,* or *K. yarrowii*. A species classified as *Pichia* genus may be, for example, *P. anomala, P. heedii, P. guilliermondii, P. kluyveri, P. membranifaciens, P. norvegensis, P. ohmeri, P. pastoris, P. methanolica,* or *P. subpelliculosa*. A species classified as *Issachenkia* genus may be, for example, *I. orientalis*. A species classified as *Hansenula* genus may be, for example, *H. subpelliculosa, H. anomala, H. polymorpha, H. holstii Wick,* or *H. capsulata Wick.*

In some embodiments, the yeast cell may further include a genetic modification to reduce the activity of an enzyme catalyzing the conversion from pyruvate to acetaldehyde, an enzyme catalyzing the conversion from lactate to pyruvate, an enzyme catalyzing the conversion from dihydroxyacetone phosphate (DHAP) to glycerol-3-phosphate (G3P), an enzyme catalyzing the conversion from glycerol-3-phosphate (G3P) to glycerol, an enzyme catalyzing the conversion from acetaldehyde to acetate, or a combination of these enzymes.

In some embodiments of the yeast cell, the enzyme catalyzing the conversion from pyruvate into acetaldehyde may belong to EC 4.1.1.1, the enzyme catalyzing the conversion from lactate to pyruvate may belong to EC 1.1.2.4 or EC 1.1.2.3, the enzyme catalyzing the conversion from DHAP to G3P may belong to EC 1.1.1.8, the enzyme catalyzing the conversion from glycerol-3-phosphate (G3P) to glycerol may belong to EC 3.1.3.21, and the enzyme catalyzing the conversion from acetaldehyde to acetate may belong to EC 1.2.1.3, EC 1.2.1.4, or EC 1.2.1.5.

In some embodiments, a gene that encodes the enzyme catalyzing the conversion from pyruvate to acetaldehyde, a gene that encodes the enzyme catalyzing the conversion from lactate to pyruvate, a gene that encodes the enzyme catalyzing the conversion from dihydroxyacetone phosphate (DHAP) to glycerol-3-phosphate (G3P), a gene that encodes the enzyme catalyzing the conversion from glycerol-3-phosphate to glycerol, a gene that encodes the enzyme catalyzing the conversion from acetaldehyde to acetate, or a combination may be disrupted in the yeast cell.

The enzyme catalyzing the conversion from pyruvate into acetaldehyde may be pyruvate decarboxylase (PDC). PDC may have a sequence identity of 75% or more, 80% or more, 85% or more, 90% or more, 95% or more, 96% or more, 97% or more, 98% or more, 99% or more, or 100%, with respect to an amino acid sequence of SEQ ID NO: 22. PDC gene may have a sequence identity of 75% or more, 80% or more, 85% or more, 90% or more, 95% or more, 96% or more, 97% or more, 98% or more, 99% or more, or 100%, with respect to a nucleotide sequence of SEQ ID NO: 23. PDC may include PDC1 (SEQ ID NO: 22), PDC5, and PDC6. PDC may catalyze a conversion from pyruvate to acetaldehyde in anaerobic or aerobic conditions. PDC gene may be disrupted due to substitution with LDH gene. In the yeast cell, PDC gene may be attenuated. In some embodiments, in the yeast cell, at least one selected from PDC1 gene, PDC5 gene, and PDC6 gene may be attenuated. In some embodiments, in the yeast cell, a gene that encodes at least one selected from PDC1, PDC5, and PDC6 may be inactivated. For example, PDC1 gene, PDC5 gene, PDC6 gene, PDC1 gene and PDC5 gene, PDC1 gene and PDC6 gene, or PDC5 gene and PDC6 gene may be inactivated.

The enzyme catalyzing the conversion from lactate to pyruvate may be lactate cytochrome-c oxidoreductase (CYB2). The enzyme catalyzing the conversion from lactate to pyruvate may have cytochrome c-dependency. CYB2 may be classified as EC 1.1.2.4 acting on D-lactate, or EC 1.1.2.3 acting on L-lactate. The enzyme catalyzing the conversion from lactate to pyruvate may have a sequence identity of 75% or more, 80% or more, 85% or more, 90% or more, 95% or more, 96% or more, 97% or more, 98% or more, 99% or more or 100%, with respect to the amino acid sequence of SEQ ID NO: 24. A gene that encodes the enzyme catalyzing the conversion from lactate to pyruvate may have a sequence identity of 75% or more, 80% or more, 85% or more, 90% or more, 95% or more, 96% or more, 97% or more, 98% or more, 99% or more or 100%, with respect to the nucleotide sequence of SEQ ID NO: 25. The CYB2 gene may be disrupted by substitution with LDH gene.

The enzyme catalyzing the conversion from DHAP to G3P may be NAD-dependent glycerol-3-phosphate dehydrogenase (GPD). GPD may be an NAD+-dependent enzyme. An example of GPD may be cytosolic glycerol-3-phosphate dehydrogenase, which is an enzyme catalyzing reduction of dihydroxyacetone phosphate (DHAP) into glycerol-3-phosphate by oxidation of NADH into NAD+. GPD may be classified as EC 1.1.1.8. Examples of GPD are GPD1 and GPD2. GPD may have a sequence identity of 75% or more, 80% or more, 85% or more, 90% or more, 95% or more, 96% or more, 97% or more, 98% or more, 99% or more, or 100%, with respect to an amino acid sequence of SEQ ID NO: 26. A gene that encodes GPD may have a sequence identity of 75% or more, 80% or more, 85% or more, 90% or more, 95% or more, 96% or more, 97% or more, 98% or more, 99% or more, or 100%, with respect to a nucleotide sequence of SEQ ID NO: 27. GPD gene may be disrupted by substitution with LDH gene.

The enzyme catalyzing the conversion from glycerol-3-phosphate to glycerol may be glycerol phosphate phosphatase (GPP). Examples of GPP are *S. cerevisiae*-derived GPP1 and GPP2. GPP gene and GPP protein may have a nucleotide sequence of SEQ ID NO: 28 and an amino acid sequence of SEQ ID NO: 29, respectively. GPP gene may be disrupted by substitution with LDH gene.

The enzyme catalyzing the conversion from acetaldehyde to acetate may be acetaldehyde dehydrogenase (ALD). ALD may have NAD(P)+ dependency. ALD may have a sequence identity of 75% or more, 80% or more, 85% or more, 90% or more, 95% or more, 96% or more, 97% or more, 98% or more, 99% or more, or 100%, with respect to an amino acid sequence of SEQ ID NO: 30. ALD gene may have a sequence identity of 75% or more, 80% or more, 85% or more, 90% or more, 95% or more, 96% or more, 97% or more, 98% or more, 99% or more, or 100%, with respect to a nucleotide sequence of SEQ ID NO: 31. ALD may include ALD6 (also referred to as ALD1), ALD2, ALD3, ALD4, and ALD5. ALD gene may be disrupted by substitution with LDH gene. In the yeast cell, ALD gene may be attenuated. In some embodiments, in the yeast cell, at least one selected from ALD6 gene, ALD2 gene, and ALD3 gene may be attenuated. In some embodiments, in the yeast cell, a gene that encodes at least one selected from ALD6 gene, ALD2 gene, and ALD3 may be inactivated.

In some embodiments of the yeast cell, the enzyme catalyzing the conversion from pyruvate to acetaldehyde may be pyruvate decarboxylase (PDC), the enzyme catalyzing the conversion from lactate to pyruvate may be lactate cytochrome-c oxidoreductase (CYB2), the enzyme catalyzing the conversion from DHAP to G3P may be NAD-dependent glycerol-3-phosphate dehydrogenase (GPD), the enzyme catalyzing the conversion from glycerol-3-phosphate to glycerol may be glycerol phosphate phosphatase (GPP), and the enzyme catalyzing the conversion from acetaldehyde to acetate may be acetaldehyde dehygrogenase.

In some embodiments, the yeast cell may have an increased activity of the enzyme catalyzing the conversion from acetaldehyde to acetyl-CoA, compared to that in a parent cell of the yeast cell.

In some embodiments, the enzyme catalyzing the conversion from acetaldehyde to acetyl-CoA may be acylating acetaldehyde dehydrogenase (A-ALD) classified as EC 1.2.1.10.

In some embodiments, a type of the enzyme catalyzing the conversion from acetaldehyde to acetyl-CoA may be a protein that is part of a bifunctional aldolase-dehydrogenase complex involved in 4-hydroxy-2-ketovalerate catabolism. Such bifunctional enzymes catalyze the final two steps in the meta-cleavage pathway for catechol, an intermediate in the degradation of phenols, toluenes, naphthalenes, biphenyls, and other aromatic compounds in many bacterial species. 4-hydroxy-2-ketovalerate is first converted by 4-hydroxy-2-ketovalerate aldolase to pyruvate and acetaldehyde. Subsequently, acetaldehyde is converted by A-ALD to Acetyl-CoA. An example of this type of A-ALD is the DmpF protein in *Pseudomonas* sp. CF600 (Genbank No: CAA43226). The MhpF protein in *E. coli* is a homologue of the DmpF. Another type of the enzyme catalyzing the conversion from acetaldehyde to acetyl-CoA may be a protein that catalyzes the reversible conversion of acetyl-CoA to acetaldehyde in strictly or facultative anaerobic microorganisms, but does not possess alcohol dehydrogenase activity. An example of this type of protein has been reported in *Clostridium kluyveri*. A-ALD is annotated in the genome of *Clostridium kluyveri* DSM 555 (Genbank No: EDK33116). A homologous protein AcdH is identified in the genome of *Lactobacillus plantarum* (Genbank No: NP_784141). Another example of this type of proteins is the gene product in *Clostridium beijerinckii* NRRL B593 (Genbank No: AAD31841). An example of the A-ALD is the MphF in *E. coli* or a functional homologue thereto, for example, EutE from *E. coli* and *S. typhimurium* (EutE gene having a nucleotide sequence of SEQ ID NO: 32 and EutE protein having an amino acid sequence of SEQ ID NO: 33), or the dmpF protein from *Pseudomonas* sp. CF600. The A-ALD may have NAD(P)+ dependency. The A-ALD may have an activity to catalyze the following reaction:

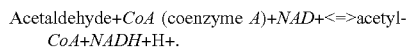

Acetaldehyde+*CoA* (coenzyme *A*)+*NAD*+<=>acetyl-CoA+NADH+H+.

The A-ALD may be expressed without forming a complex with other proteins. In some embodiments, the yeast cell may exclude an exogenous enzyme that belongs to EC 4.1.3.39 or a gene thereof.

The A-ALD may originate from *E. coli*. The A-ALD gene in *E. coli*, i.e., the mhpF, may be one of transcription units consisting of mhpA, mhpB, mhpC, mhpD, mhpE, and mhpF. In general, MhpE and MhpF may be as a complex in other microorganisms. However, MhpE and MhpF may be present separately without forming a complex in yeast, each having catalytic activity. The enzyme catalyzing the conversion of acetaldehyde to acetyl-CoA, for example, MhpF, may have a 95% or more sequence identity to an amino acid sequence of SEQ ID NO: 34.

The yeast cell may include an exogenous gene that encodes the enzyme catalyzing the conversion of acetaldehyde to acetyl-CoA. The A-ALD exogenous gene may be, in the yeast cell, expressed in an amount sufficient to increase an activity of the enzyme catalyzing the conversion from acetaldehyde to acetyl-CoA. The A-ALD exogenous gene may encode an amino acid sequence having a 95% or more sequence identity to an amino acid sequence of SEQ ID NO: 34. The A-ALD exogenous gene may be a nucleotide sequence having a 95% or more sequence identity to a nucleotide sequence of SEQ ID NO: 35 or SEQ ID NO: 36. The nucleotide sequence of SEQ ID NO: 35 is a nucleotide sequence of *E. coli*-derived A-ALD gene. The A-ALD exogenous gene may have an altered sequence with a suitable or optimized codon for expression in the yeast cell. This codon alteration may be appropriately made as long as an amino acid sequence of a protein does not change. The nucleotide sequence of SEQ ID NO: 36 is an example of a nucleotide sequence of *E. coli*-derived A-ALD gene having an optimized codon for expression in the yeast cell.

The A-ALD exogenous gene may be introduced into a parent cell through an expression vector. In some embodiments, the A-ALD exogenous gene may be introduced in the form of a linear polynucleotide into a parent cell. In some embodiments, the A-ALD exogenous gene may be expressed from an intracellular expression vector (for example, plasmid). In some embodiments, for stable expression, the A-ALD exogenous gene may be inserted into an intracellular genetic material (for example, chromosome) and expressed. In some embodiments, the A-ALD exogenous gene may be appropriately regulated by an exogenous promoter that is operably linked to the gene. The exogenous promoter may be ccw12, pdc1, tef1 or pgk1 gene-derived promoter.

In another aspect of the present disclosure, a method of producing a recombinant yeast cell that produces lactate is provided. The method includes: introducing a gene that encodes an enzyme catalyzing conversion from pyruvate to lactate into a yeast cell; and disrupting a gene that encodes rim15 protein, a gene that encodes igo2 protein, or a gene that encodes rim15 protein and a gene that encodes igo2 protein in the yeast cell.

In some embodiments, "the gene that encodes the enzyme catalyzing the conversion from pyruvate to lactate" may be introduced into a yeast cell and inserted into an endogenous genetic material (for example, chromosome) of a yeast cell. This gene may be inserted into one or more locations of a particular endogenous genes of of the yeast cell to disrupt the endogenous genes. The particular endogenous genes to be disrupted may include a gene that encodes the enzyme catalyzing the conversion from pyruvate into acetaldehyde, a gene that encodes the enzyme catalyzing the conversion from lactate to pyruvate, a gene that encodes the enzyme catalyzing the conversion from dihydroxyacetone phosphate (DHAP) to glycerol-3-phosphate (G3P), a gene that encodes the enzyme catalyzing the conversion from glycerol-3-phosphate to glycerol, and a gene that encodes the enzyme catalyzing the conversion from acetaldehyde into ethanol. Examples of the genes to be disrupted are PDC, CYB2, GPD, GPP, and ADH gene."

The gene that encodes the enzyme catalyzing the conversion from pyruvate to lactate may be introduced in the yeast cell, but not inserted into the endogenous genetic material of the yeast cell. For example, the gene may be included in an expression vector, such as a plasmid, and remain separated from the endogenous genetic material of the yeast cell.

The gene that encodes the enzyme catalyzing the conversion from pyruvate to lactate may be introduced in an expressionable form into a yeast cell, and expressed to generate a gene product thereof including "the enzyme catalyzing the conversion from pyruvate to lactate" in the yeast cell. The expressionable form may be a structure in which the gene is operably linked to an expression regulatory sequence. For example, the gene may be operably linked to at least one selected from an exogenous enhancer, an operator, a promoter, and a transcription terminator to be expressionable in a yeast cell, or may be linked to an endogenous regulatory sequence of the yeast cell to be expressionable in the yeast cell. The promoter may be selected from the group consisting of CCW12 promoter, CYC promoter, TEF1 promoter, PGK1 promoter, GPD promoter, and ADH promoter. The CCW12 promoter, CYC promoter, TEF1 promoter, PGK1 promoter, GPD promoter, and ADH promoter may have nucleotide sequences of SEQ ID NO: 13, 14, 15, 16, 17, and 18, respectively. The terminator may be selected from the group consisting of PGK1 (phosphoglycerate kinase 1), CYC1 (cytochrome c transcription), and GAL1. The CYC1 terminator may have a nucleotide sequence of SEQ ID NO: 19. The vector may further include a selection marker.

The introducing of a gene that encodes an enzyme catalyzing conversion from pyruvate to lactate may be performed using any known method of introducing a genetic material into a yeast cell (R. Danile Gietz et al., Biotechniques 30:816-831, April 2001). The introducing may include a spheroplast method, intact yeast cell transformation, electroporation, or a combination thereof. For example, intact yeast cell transformation may use a particular monovalent alkali cation (Na+, K+, Rb+, Cs+, and Li+) in a combination with PEG to promote uptake of DNA, such as a plasmid, by a yeast cell. For example, intact yeast cell transformation may include applying a heat shock to an aqueous solution of PEG, LiAc, carrier ssDNA, plasmid DNA, and a yeast cell. For example, electroporation may include applying an electric pulse to a mixed medium including a yeast cell and DNA, such as plasmid DNA.

Accordingly, the introducing may include contacting a yeast cell with the gene that encodes the enzyme catalyzing the conversion from pyruvate to lactate in an appropriate liquid medium. The yeast cell may be spheroplast or intact yeast cell. The liquid medium may vary depending on a selected transformation method. The liquid medium may be, for example, water, an aqueous solution, or a buffer. The aqueous medium may include PEG and at least one type of monovalent alkali cations selected from $Na^+$, $K^+$, $Rb^+$, $Cs^+$, and $Li^+$. The liquid medium may be carrier ssDNA. The liquid medium may be an aqueous solution that includes PEG, LiAc, and carrier ssDNA.

The contacting may be performed while applying a heat shock or electric pulse. The heat shock may include culturing at a temperature of about 40° C. to about 45° C., for example, about 42° C. The electric pulse may be applied between electrodes in an electroporation cuvette or a petri dish. Variables of the electric pulse such as field strength (kV/cm), capacitance (uF), and resistance may vary depending on a particular condition of prepared cells. Accordingly, transformation efficiency may vary depending on yeast strains. Regarding a given yeast strain, one of ordinary skill in the art may search for variables of pulse depending on a cell and select appropriate variables to obtain a sufficient number of transformants.

In the introduction into the yeast, the gene may be included in a vector, with a homologous sequence with respect to an endogenous genetic material of a parent cell of a yeast cell. The homologous sequence is complementary to a target sequence present in an endogenous genetic material of a parent yeast cell, and accordingly may be substituted with the target sequence by homologous recombination. The target sequence may include a gene that encodes the enzyme catalyzing the conversion from pyruvate to acetaldehyde, a gene that encodes the enzyme catalyzing the conversion from lactate to pyruvate, a gene that encodes the enzyme catalyzing the conversion from dihydroxyacetone phosphate (DHAP) to glycerol-3-phosphate (G3P), a gene that encodes the enzyme catalyzing the conversion from glycerol-3-phosphate to glycerol, and a gene that encodes the enzyme catalyzing the conversion from acetaldehyde to ethanol. Examples of the target sequence are PDC, CYB2, GPD, GPP, and ADH gene. The vector may include two sequences which are respectively homologous to the 5' end and 3' end of the target sequence. In this regard, the introducing may include culturing the yeast cell under a selection pressure during or after the contacting. The selection pressure may indicate a material or state that enables to select only cells where homologous recombination has occurred. The selection pressure may include culturing in the presence of antibiotics. In this regard, the vector may include a gene that provides antibiotic resistance to the yeast cell, for example, a gene that encodes an enzyme that decomposes antibiotics.

In the method of producing a yeast cell that produces lactate, the disrupting a gene that encodes rim15 protein, a gene that encodes igo2 protein, or a gene that encodes rim15 protein, and a gene that encodes igo2 protein in the yeast cell may be performed as follows. The disrupting may include contacting a yeast cell with a polynucleotide that has a homologous sequence with respect to the gene that encodes rim15 protein, the gene that encodes igo2 protein, or the gene that encodes rim15 protein and the gene that encodes igo2 protein in an appropriate liquid medium. The homologous sequence may be entirely or partially homologous with respect to these genes. The homologous sequence may be homologous to an encoding region or expression-regulatory region of these genes. The polynucleotide having a homologous sequence with respect these genes may be linked to a gene, for example, a gene that encodes an enzyme associated with promotion of lactate biosynthesis, such as LDH gene. For example, the polynucleotide having a homologous sequence with respect to these genes may be a polynucleotide present in a vector such as plasmid. The homologous sequence may be used to substitute the gene that encodes rim15 protein, the gene that encodes igo2 protein, or the gene that encodes rim15 protein and the gene that encodes igo2 protein by homologous recombination. The vector may include two sequences which are respectively homologous to the 5' end and 3' end of the target sequence. In this regard, the disrupting may include culturing the yeast cell under a selection pressure during or after the contacting. The selection pressure may indicate a material or state that enables to select only cells where homologous recombination has occurred. The selection pressure may include culturing in the presence of antibiotics. In this regard, the vector may include a gene that provides antibiotic resistance to the yeast cell, for example, a gene that encodes an enzyme that decomposes antibiotics.

For example, the contacting in the disrupting of the gene that encodes rim15 protein, the gene that encodes igo2 protein, or the gene that encodes rim15 protein and the gene that encodes igo2 protein in the yeast cell may be performed under the same conditions as in the introducing of the gene that encodes an enzyme catalyzing conversion from pyruvate to lactate into a yeast cell. For example, the introducing may be performed using any methods known in the art including a spheroplast method, intact yeast cell transformation, and electroporation. For example, intact yeast cell transformation may use a particular monovalent alkali cation ($Na^+$, $K^+$, $Rb^+$, $Cs^+$, and $Li^+$) in a combination with PEG to promote uptaking of DNA such as plasmid by a yeast cell. For example, intact yeast cell transformation may include applying a heat shock to an aqueous solution of PEG, LiAc, carrier ssDNA, and plasmid DNA. For example, electroporation may include applying an electric pulse to a DNA-containing mixed medium including a yeast cell and DNA such as plasmid DNA.

For example, the yeast cell may be a spheroplast or intact yeast cell. The liquid medium may vary depending on a selected transformation method. The liquid medium may be, for example, water, an aqueous solution, or a buffer. The aqueous medium may include PEG and at least one type of monovalent alkali cations selected from $Na^+$, $K^+$, $Rb^+$, $Cs^+$, and $Li^+$. The liquid medium may be carrier ssDNA. The liquid medium may be an aqueous solution that includes PEG, LiAc, and carrier ssDNA.

In the contacting, each of the genes may be included in a vector together with a homologous sequence with respect to an endogenous genetic material of a parent cell of the yeast cell. The homologous sequence is complementary to a target sequence present in an endogenous genetic material of a yeast cell of a parent cell, and accordingly may be substituted with the target sequence by homologous recombination. The target sequence may include a gene that encodes rim15 protein, a gene that encodes igo2 protein, or a gene that encodes rim15 protein and igo2 protein. The target sequence may includes a gene that encodes the enzyme catalyzing the conversion from pyruvate to acetaldehyde, a gene that encodes the enzyme catalyzing the conversion from lactate to pyruvate, a gene that encodes the enzyme catalyzing the conversion from dihydroxyacetone phosphate (DHAP) to glycerol-3-phosphate (G3P), a gene that encodes the enzyme catalyzing the conversion from glycerol-3-phosphate to glycerol, and a gene that encodes the enzyme catalyzing the conversion from acetaldehyde to ethanol. The target sequence may include PDC, CYB2, GPD, GPP, and ADH genes. The vector may include two sequences which are homologous to the 5' end and 3' end, respectively, of the target sequence. In this regard, the disrupting may include culturing the yeast cell under a selection pressure during or after the contacting. The selection pressure may indicate a material or state that enables to select only cells where homologous recombination has occurred. The selection pressure may include culturing in the presence of antibiotics. In this regard, the vector may include a gene that provides antibiotic resistance to the yeast cell, for example, a gene that encodes an enzyme that degrades antibiotics.

In another aspect of the present disclosure, a method of producing lactate is provided, which method includes: culturing a yeast cell according to any of the above-described embodiments in a culture medium to obtain a culture including lactate; and separating lactate from the culture medium.

The culturing may be performed in a culture medium including a carbon source, for example, glucose. The culture medium used in the culturing of the yeast cell may be any general culture medium appropriate for growth of a host cell such as a minimal medium or a complex medium including an appropriate supplement. An appropriate medium may be commercially purchased or may be prepared using a known preparation method. The culture medium used in the culturing of the yeast cell may be a medium satisfying the specific requirements for a yeast cell. The culture medium may include a carbon source, a nitrogen source, a salt, a trace element, or a combination thereof.

To obtain lactate from the genetically engineered yeast cell, the culturing conditions may be appropriately controlled. The yeast cell may be cultured under aerobic conditions for growth. Then, the yeast cell may be cultured under microaerobic conditions or anaerobic conditions to produce lactate. The term "anaerobic conditions" refers to an oxygen-free environment. When "microaerobic conditions" referred to herein is used as the culture or growth conditions for the yeast cell, it means that a concentration of dissolved oxygen (DO) in the culture medium may be greater than 0% and equal to or smaller than about 10% of a saturation concentration of dissolved oxygen in a liquid medium. In some embodiments, the microaerobic conditions may include growing or resting a cell in a liquid medium or a solid agar plate in a sealed chamber in which the concentration of oxygen is maintained at less than 1%. The concentration of oxygen may be maintained by, for example, sparging a culture product with a $N_2/CO_2$ mixture or other appropriate non-oxygen gases. Under the microaerobic conditions, the concentration of dissolved oxygen (DO) may be maintained in a range of about 0% to about 10%, about 0% to about 8%, about 0% to about 6%, about 0% to about 4%, or about 0% to about 2%.

The terms "culture medium" and "culturing condition" refer to conditions and methods for facilitating growth and reproduction of the yeast cell. The terms "culture" and "culture product" refer to materials resulting from the implementation of said conditions and methods. The culture medium may contain a carbon source, a nitrogen source, or oxygen used by the yeast cell. The carbon source may be an assimilable carbon source for any yeast cell. For example, the carbon source may include a monosaccharide, a disaccharide, or a polysaccharide. For example, the carbon source may be glucose, fructose, mannose, or galactose. The nitrogen source may be an organic nitrogen compound or an inorganic nitrogen compound. Examples of the nitrogen source are an amino acid, amide, amine, a nitrate, and an ammonium salt. The culture medium may include a buffering agent to maintain a pH of 3 to 5. The buffering agent may be bicarbonate. The culturing may be performed while maintaining the pH of the culture medium at pH 3 to 5. The maintaining of the pH of the culture medium at pH 3 to 5 may be achieved by adding a buffering agent to the culture medium or by adding an acid or base to the culture medium during the culturing. For example, a base may be added to the culture medium when the culture medium has a pH above 5. An acid may be added to the culture medium when the culture medium has a pH below 3.

The separating of lactate from the culture or culture product may be performed using any common method known in the art, for example, using centrifugation, filtration, ion-exchange chromatography, or crystallization. For example, lactate may be separated by centrifuging the culture or culture product at a low speed to remove biomass therefrom and then by ion-exchange chromatography of a supernatant resulting from the centrifuging.

A yeast cell according to any of the above-described embodiments may be used to efficiently produce lactate.

A method of producing a yeast cell that produces lactate, according to any of the above-described embodiments, may efficiently produce the yeast cell producing lactate.

A method of producing lactate according to any of the above-described embodiments may efficiently produce lactate.

One or more embodiments of the present disclosure will now be described in detail with reference to the following examples. However, these examples are only for illustrative purposes and are not intended to limit the scope of the one or more embodiments of the present disclosure.

EXAMPLE 1

Production of Lactate from Yeast Strain in which Rim15 Gene and/or Igo2 Gene are Disrupted 1. Construction of Strain

*S. cerevisiae* strain used in the following examples was prepared as follows.

(1) Construction of *S. cerevisiae* CEN.PK2-1D (Δadh1::ldh)

(1.1) Construction of adh1 Gene Deletion Cassette

To construct 'ldh cassette'-containing vector, CCW12 gene promoter (hereinafter referred to as "P CCW12" or "CCW12 promoter") was amplified by polymerase chain reaction (PCR) using *S. cerevisiae* CEN.PK2-1D genome DNA as a template, and a primer set of SEQ ID NOS: 37 and 38. The resulting CCW12 gene promoter amplification product (SEQ ID NO: 13) and synthesized ldh gene (SEQ ID NO: 6) (DNA2.0 Inc., USA) were respectively cleaved by using SacI/XbaI and BamHI/SalI, and then linked to a pRS416 vector (ATCC87521™) that was cleaved using the same enzyme. pRS416 vector is a yeast centromere shuttle plasmid having a T7 promoter, ampicillin resistance in bacteria, URA3 cassette (selection marker) in yeast, and a restriction enzyme cloning site.

Figure 2:
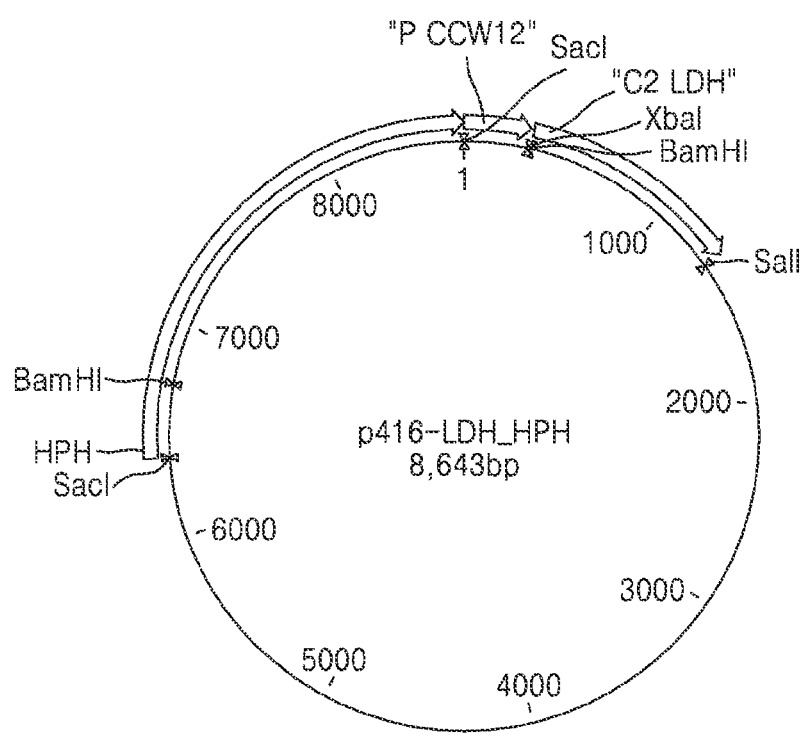
FIG. 2 is a map of p416-Idh-HPH vector.

"Hygromycin B phosphotransferase (HPH) cassette" sequence (SEQ ID NO: 41) was amplified by PCR using pCEP4 plasmid (Invitrogen, Cat. no. V044-50) as a template, and a primer set of SEQ ID NOS: 39 and 40. The resulting amplified "HPH cassette" and the pRS416 vector were cleaved by using a SacI enzyme and then linked to each other to construct a vector p416-Idh-HPH in which the Idh cassette and the HPH cassette were operably linked to each other. FIG. 2 is a cleavage map of p416-Idh-HPH vector. Referring to FIG. 2, "P CCW12" and "C2 LDH" indicate CCW12 promoter and LDH orf, respectively. pCEP4 plasmid is an Episomal mammalian expression vector using a cytomegalovirus (CMV) immediate early enhancer/promoter for high-level transcription of recombined gene inserted into multiple cloning sites. For stable selection, pCEP4 has hygromycin B resistance gene in transfected cell. The Idh cassette indicates a region that includes Idh gene and a regulatory region thereof and thus enables expression of Idh gene. The Idh gene was transcribed in the presence of CCW12 promoter. The HPH cassette indicates a region that includes a hygromycin B resistance gene and a regulatory region thereof and thus enables expression of the hygromycin B resistance gene.

An adh1 deletion cassette was prepared by PCR using p416-Idh-HPH vector as a template and a primer set of SEQ ID NO: 42 and SEQ ID NO: 43. A region of the $1^{st}$ to $51^{st}$ nucleotide in each primer of SEQ ID NO: 42 and SEQ ID NO: 43 substitutes the adh1 gene of the S. cerevisiae genome with the Idh-HPH cassette by homologous recombination.

The adh1 deletion cassette was used to inactivate alcohol dehydrogenase (adh1) and introduce Idh gene in S. cerevisiae CEN.PK2-1 D genome via substitution of adh1 with the Idh-HPH cassette.

(1.2) Construction of S. cerevisiae CEN.PK2-1D (Δadh1::Idh)

To substitute adh1 gene in S. cerevisiae CEN.PK2-1D with Idh gene, "adh1 deletion cassette" prepared in Section (1.1) was introduced into S. cerevisiae CEN.PK2-1D strain by heat shock transformation, and the result was cultured in 200 ug/mL of a hygromycin-containing YPD medium (1% (w/v) of yeast extract, 1% (w/v) of peptone, and 2% (w/v) of glucose) at about 30° C. for 3 days to substitute chromosomal adh1 gene with Idh gene, thereby producing S. cerevisiae CEN.PK2-1D(Δadh1::Idh) strain.

(2) Construction of S. cerevisiae CEN.PK2-1D (Δ adh1::Idh, Δ pdc1::Idh, Δ cyb2::Idh, Δ gpd1::Idh)

(2.1) Construction of pdc1, cyb2, and gpd1 Deletion Vectors

A pyruvate decarboxylase1 (Pdc1) deletion cassette was prepared as follows. PCR was performed using p416-Idh-HPH as a template and a primer set of SEQ ID NOS: 44 and 45. The resulting amplified product was cleaved using SacI, and then linked to pUC57-Ura3HA vector (DNA2.0 Inc.: SEQ ID NO: 46) cleaved by using the same enzyme, to construct pUC57-ura3HA-Idh. Then, PCR was performed using pUC57-ura3HA-Idh as a template and a primer set of SEQ ID NOS: 47 and 48, thereby preparing the pdc1 deletion cassette. A region of the $1^{st}$ to $42^{nd}$ nucleotides and a region of the $1^{st}$ to $44^{th}$ nucleotides in primer of SEQ ID NO: 47 and SEQ ID NO: 48, respectively are to be substituted with pdc1 gene by homologous recombination with a homologous sequence of S. cerevisiae genome.

An L-lactate cytochrome-c oxidoreductase (cyb2) deletion cassette was amplified by PCR using pUC57-ura3HA-Idh deletion vector as a template and a primer set of SEQ ID NOS: 49 and 50. A region of the $1^{st}$ to $45^{th}$ nucleotides in each primer of SEQ ID NO: 49 and SEQ ID NO: 50 are to be substituted with cyb2 gene by homologous recombination with a homologous sequence of S. cerevisiae genome.

A Glycerol-3-phosphate dehydrogenase) (gpd1) deletion cassette was amplified by PCR using pUC57-ura3HA-Idh deletion vector as a template and a primer set of SEQ ID NOS: 51 and 52. A region of the $1^{st}$ to $50^{th}$ nucleotides in the primer of SEQ ID NO: 52 is to be substituted with gpd1 gene by homologous recombination with a homologous sequence of S. cerevisiae genome.

(2.2) Construction of S. cerevisiae CEN.PK2-1D (Δ adh1::Idh, Δ pdc1::Idh, Δ cyb2::Idh, Δ gpdt:Idh) Strain First, to substitute pdc1 gene with Idh gene in S. cerevisiae CEN.PK2-1D(Δadh1::Idh), "pdc1 deletion cassette" prepared in Section (2.1) was introduced to S. cerevisiae CEN.PK2-1D (Δadh1::Idh) prepared in Section (1) by heat shock transformation, followed by culturing the result in a selection marker Ura-dropout medium at about 30° C. for 3 days to substitute chromosomal pdc1 gene with Idh gene. To analyze the genotype of the constructed strain, the deletion or not of pdc1 gene was confirmed by PCR using the genome of the constructed strain as a template and a primer set of SEQ ID NOS: 53 and 54.

As a result, the constructed strain was identified to be S. cerevisiae CEN.PK2-1D (Δadh1::Idh, Δpdc1::Idh) strain.

Next, to substitute cyb2 gene with Idh gene in S. cerevisiae CEN.PK2-1D (Δadh1::Idh, Δpdc1::Idh) strain, "cyb2 deletion cassette" prepared in Section (2.1) was introduced to the strain by heat shock transformation, followed by culturing the result in a selection marker Ura-dropout medium at about 30° C. for 3 days to substitute chromosomal cyb2 gene with Idh gene. To analyze the genotype of the constructed strain, the deletion or not of cyb2 gene was confirmed by PCR using the genome of the constructed strain as a template and a primer set of SEQ ID NOS: 55 and 56.

As a result, the constructed strain was identified to be S. cerevisiae CEN.PK2-1D (Δadh1::Idh,Δpdc1::Idh,Δcyb2::Idh) strain.

Next, to substitute gpd1 gene with Idh gene in S. cerevisiae CEN.PK2-1D (Δadh1::Idh,4pdc1::Idh,4cyb2::Idh) strain, "gpd1 deletion cassette" prepared in Section (2.1) was introduced to the strain by heat shock transformation, followed by culturing cultured in a selection marker Ura-dropout medium at about 30° C. for 3 days to substitute chromosomal gpd1 gene with Idh gene. To analyze the genotype of the constructed strain, the deletion or not of gpd1 gene was confirmed by PCR using the genome of the constructed strain as a template and a primer set of SEQ ID NOS: 57 and 58.

As a result, the constructed strain was identified to be S. cerevisiae CEN.PK2-1D (Δadh1::Idh,Δpdc1::Idh,Δcyb2::Idh,Δgpd1::Idh) strain.

(3) Construction of S. cerevisiae CEN.PK2-1D (Δ adh1:: Idh, Δ pdc1 ::Idh, Δ cyb2::Idh, Δ gpd1::Idh,mhpF, Δ aId6, EutE)

(3.1) Construction and Introduction of mhpF Insertion Vector

MhpF gene was inserted to enhance a conversion pathway from acetaldehyde to acetyl-CoA in S. cerevisiae CEN.PK2-1D (Δ adh1::Idh, Δ pdc1::Idh, Δ cyb2::Idh, Δ gpd1::Idh).

To express E. coli-derived MhpF gene (SEQ ID NO: 35) in S. cerevisiae from a vector, the MhpF gene (SEQ ID NO: 36) (DNA2.0 Inc., USA) optimized with a codon that frequently occurs in S. cerevisiae was synthesized. This synthesized MhpF gene was linked to a TEF1 promoter sequence (SEQ ID NO: 15) at the 5' end to regulate transcription by the TEF1 promoter. pJ1214-MhpF (DNA2.0 Inc., USA) including the synthesized TEF1 promoter-MhpF gene was used. pJ1214 (DNA2.0 Inc., USA), an expression vector for S. cerevisiae, included a URA3 marker and a 2um on sequence.

FIG. 1 is a cleavage map of pJ1214-MhpF vector. In FIG. 1, "P TEF" indicates a TEF promoter. The pJ1214-mhpF vector had a nucleotide sequence of SEQ ID NO: 59.

The MhpF gene of pJ1214-mhpF and 'HIS3 cassette' were each linked to 'pUC19 vector'(NEB, N3041) by using SalI restriction enzyme to construct pUC19-His-MhpF vector (SEQ ID NO: 60). HIS3 cassette was an amplification product obtained by PCR using pRS413 (ATCC8758) as a template and a primer set of SEQ ID NO: 61 and SEQ ID NO: 62. In pUC19-His-MhpF vector, mhpF is expressed in the presence of GPD promoter.

A mhpF introduction cassette was obtained by PCR using pUC19-His-MhpF vector as a template, and a primer set of SEQ ID NOS: 63 and 64 to which a leu2 homologous recombination sequence and a promoter were linked. The leu2 homologous recombination sequence includes a mutation site in a parent strain that is unable to express a functional protein.

This constructed mhpF insertion cassette was introduced into S. cerevisiae CEN.PK2-1D(Δ adh1::Idh, Δ pdc1 ::Idh, Δ cyb2::Idh, Δ gpd1::Idh) by heat shock transformation, followed by culturing the cells in a histidine dropout medium (6.7 g/L of yeast nitrogen base without amino acids (Sigma-Aldrich: Cat. no. Y0626), and 1.9 g/L of yeast synthetic dropout medium without histidine (Sigma-Aldrich: Cat. no. Y1751), and 2 (w/v)% of glucose) to substitute chromosomal Leu2 ORF with the cassette.

To verify the introduction of mhpF gene into Leu2 locus in the obtained strain, the deletion and introduction or not of the gene were confirmed by PCR using the cell genome as a template and a primer set of SEQ ID NOS: 65 and 66. As a result, S. cerevisiae CEN.PK2-1D (Δ adh1::Idh, Δ pdc1 ::Idh, Δ cyb2::Idh, Δ gpd1::Idh, mhpF) was prepared.

(3.2) Construction and Introduction of ald6 Deletion Vector

Acetaldehyde dehydrogenase 6 (ald6) gene deletion cassette was amplified by PCR using pUC57-ura3HA deletion vector as a template and a primer set of SEQ ID NOS: 67 and 68. The sequences of SEQ ID NOS: 67 and 68 include a site that is to be substituted with ald6 gene by recombination with a homologous sequence of chromosome of S. cerevisiae.

To delete ald6 gene from S. cerevisiae CEN.PK2-1D (Δadh1::Idh, mhpF, Δpdc1:Idh, Δcyb2:Idh, Δgpd1:Idh) strain, the prepared "ald6 deletion cassette" was introduced into the strain by heat shock transformation, followed by culturing the resulting cells in a selection marker minimal Ura-dropout medium at about 30° C. for 3 days to delete chromosomal ald6 gene. To analyze the genotype of the constructed strain, the deletion or not of ald6 gene was confirmed by PCR using the genome of the constructed strain as a template and a primer set of SEQ ID NOS: 69 and 70.

As a result, the constructed strain was identified to be S. cerevisiae CEN.PK2-1D (Δ adh1::Idh, Δ pdc1 ::Idh, Δ cyb2::Idh, Δ gpd1::Idh, mhpF, Δald6) strain.

(3.3) Construction and Introduction of EutE Gene Introduction Vector (3.3.1) Construction of Enzyme Dual Function Overexpression Vector pCS-Ex1

A 689-bp DNA fragment (GPD promoter) was obtained from pRS426GPD vector that is widely used as a yeast overexpression vector, by PCR using a primer set of SEQ ID NO: 71 and SEQ ID NO: 72. This DNA fragment was mixed with pCtB1 vector (Genbank Accession Number KJ922019) treated with KpnI, cloned by using an In-fusion kit (Clontech, cat. 639650), and then introduced into TOP10 strain (Invitrogen, cat. C4040-06) as an E. coli strain for cloning, by using a conventional method. After the introduction, the strain was smeared on a LB agar medium (10 g/L of Bacto Tryptone, 5 g/L of yeast extract, 10 g/L of NaCl, and 15 g/L of Bacto Agar) containing 50 ug/mL of kanamycin, and then cultured to form colonies. After plasmid DNA was separated from the colonies, the presence of a plasmid sequence of SEQ ID NO: 74 was confirmed. As a result, a pCS-Ex1 vector as a yeast dual function overexpression vector was obtained. The term "dual function" indicates a function of gene expression after gene insertion into genome and a function of gene expression in vector.

(3.3.2) Construction of Yeast Dual Function E. coli eutE Gene Overexpression Vector A 1447-bp DNA fragment, i.e., EutE gene, was obtained from genome DNA of E. coli. MG1655 strain by PCR using a primer set of SEQ ID NO: 74 and SEQ ID NO: 75. This DNA fragment was mixed with pCS-Ex1 vector treated with KpnI and SacI, cloned by using an In-fusion kit (Clontech cat. 639650), and then introduced into TOP10 strain (Invitrogen cat. C4040-06) as an E. coli strain for cloning, by using a conventional method. After the introduction, the strain was smeared on a LB agar medium containing 50 ug/mL of kanamycin, and cultured to form colonies. After plasmid DNA was separated from the colonies, the presence of a plasmid sequence of SEQ ID NO: 76 was confirmed. As a result, MD1040 vector as a yeast dual function E. coli eutE gene overexpression vector was obtained.

(3.3.3) Preparation of Yeast Having Overexpressed E. coli eutE Gene

A 3985-bp DNA fragment was obtained from the prepared MD1040 vector by PCR using a primer set of SEQ ID NO: 77 and SEQ ID NO: 78. This fragment was introduced into S. cerevisiae CEN.PK2-1D (Δadh1::Idh, Δpdc1 ::Idh, Δcyb2::Idh, Δgpd1::Idh, mhpF, Δald6) by using a conventional method, followed by smearing on a SD-URA agar medium [6.7 g/L of Yeast nitrogen base without amino acids (Sigma-Aldrich: Cat. no. Y0626), 1.9 g/L of Yeast synthetic drop-out without uracil (Sigma-Aldrich: Cat. no. Y1501), 20 g/L of D-glucose, and 20 g/L of Bacto Agar] that is a uracil-free minimal medium, to form colonies. After 3 days, a colony including a 4357-bp DNA fragment was selected from among the formed colonies by PCR using a primer set of SEQ ID NO: 79 and SEQ ID NO: 80. In the case of genome DNA of wild-type strain, a 2300-bp DNA fragment may be obtained by PCR using a primer set of SEQ ID NO: 79 and SEQ ID NO: 80. The obtained clone was inoculated to a YPD medium (20 g/L of Bacto Peptone, 10 g/L of yeast extract, and 20 g/L of D-glucose), and cultured while stirring at about 230 rpm at about 30° C., and then smeared on a 5-FOA-including reverse-selective medium (6.7 g/L of Yeast nitrogen base without amino acids (Sigma-Aldrich: Cat. no. Y0626), 1.9 g/L of Yeast synthetic drop-out without uracil (Sigma-Aldrich: Cat. no. Y1501), 0.1 g/L of Uracil, 20 g/L of D-glucose, 1 g/L of 5-fluoroorotic acid (5-FOA), and 20 g/L of Bacto Agar) to form colonies. After 3 days, a colony including a 2963-bp DNA fragment was selected from among the colonies by PCR using a primer set of SEQ ID NO: C3 and SEQ ID NO: C4.

As a result, the constructed strain was identified to be S. cerevisiae CEN.PK2-1D (Δ adh1::Idh, Δ pdc1::Idh, Δ cyb2:: Idh, Δ gpd1::Idh, mhpF, Δ ald6, EutE) (hereinafter, also referred to as "SP1130").

(4) Construction of S. cerevisiae CEN.PK2-1D SP1130 (Δ rim15) or SP1130 (Δ igo2)

(4.1) Construction and Introduction of Rim15 Deletion Vector

A rim15 gene deletion cassette was amplified by PCR using pUC57-ura3HA deletion vector as a template and a primer set of SEQ ID NOS: 81 and 82. The sequences of SEQ ID NOS: 81 and 82 include a site that is to be substituted with rim15 gene by recombination with a homologous sequence of chromosome of S. cerevisiae.

To delete rim15 gene from S. cerevisiae CEN.PK2-1D SP1130 strain, the constructed "rim15 deletion cassette" was introduced into the strain by heat shock transformation, followed by culturing the result cells in a selection marker minimal Ura-dropout medium at about 30° C. for 3 days to delete chromosomal rim15 gene. To analyze the genotype of the constructed strain, the deletion or not of rim15 gene was confirmed by PCR using the genome of the constructed strain as a template and a primer set of SEQ ID NOS: 83 and 84.

As a result, the constructed strain was identified to be S. cerevisiae CEN.PK2-1D SP1130 (Δ rim15).

(4.2) Construction and Introduction of igo2 Gene Deletion Vector

Igo2 gene deletion cassette was amplified by PCR using pUC57-ura3HA deletion vector as a template and a primer set of SEQ ID NOS: 85 and 86. The sequences of SEQ ID NOS: 85 and 86 include a site that is to be substituted with igo2 gene by recombination with a homologous sequence of chromosome of S. cerevisiae.

To delete igo2 gene from S. cerevisiae CEN.PK2-1D SP1130 strain, the constructed "igo2 deletion cassette" was introduced into the strain by heat shock transformation, followed by culturing the result cells in a selection marker minimal Ura-dropout medium at about 30° C. for 3 days to delete chromosomal igo2 gene. To analyze the genotype of the constructed strain, the deletion or not of igo2 gene was confirmed by PCR using the genome of the constructed strain as a template and a primer set of SEQ ID NOS: 87 and 88.

As a result, the constructed strain was identified to be S. cerevisiae CEN.PK2-1D SP1130 (Δ igo2).

2. Confirmation of Lactate-Producing Characteristics of Constructed Strain

The constructed S. cerevisiae CEN.PK2-1D SP1130 (Δ rim15) and SP1130 (Δ igo2) strains were each smeared on a plate culture medium including a YPD solid medium (Yeast extract 1 (w/v) %, peptone 1 (w/v) %, and glucose 2 (w/v) %), and cultured at about 30° C. for about 24 hours. Then, the resulting strain was inoculated into 50 mL of a YPD liquid medium including 40 g/L glucose in a 250-mL flask and cultured at about 30° C. for about 16 hours under an aerobic condition while stirring the flask with a vent cap at about 230 rpm for the aerobic condition. A control group was prepared in the same manner except that S. cerevisiae CEN.PK2-1D SP1130 strain was used.

After a cell concentration of the culture solution was measured as an $OD_{600}$ value by using a spectrophotometer, the culture solution was centrifuged to remove supernatant, followed by inoculating the precipitated cells in 50 mL of a YPD liquid medium including 60 g/L of glucose and 2 g/L $CaCO_3$ in a 250-mL flask to a concentration at $OD_{600}$ of 0.5, and incubating about 30° C. for about 24 hours or longer under a microaerobic condition while shaking the flask with a flat cap in a shaking incubator at about 90 rpm.

After the culture solution was sampled at intervals during the incubation, the samples were centrifuged at about 13,000 rpm for about 10 minutes for supernatant, followed by analyzing the concentrations of various metabolites, lactate, and glucose in the supernatant by high-performance liquid chromatography (HPLC). In particular, the culture supernatant was filtered through a 0.45-um syringe filter to quantify L-lactate and glucose by using an HPLC analyzer (Waters e2695 Separation Module instrument equipped with a Waters 2414 Differential Refractometer and a Waters 2998 Photodiode Array Detector, available from Waters, Milford, Mass.). The HPLC column was an Aminex HPX-87H Organic Acid Analysis Column (300 mm×7.8 mm; Bio-Rad) equilibrated with 2.5 mM $H_2SO_4$ in water at about 60° C. and a flow rate of about 0.5 mL/min.

Table 1 shows the concentrations of cells, glucose, and lactate in the cell cultures after the incubation in the YPD liquid medium under the microaerobic condition for about 48 hours.

TABLE 1

| Strain | Cell concentration ($OD_{600}$) | Consumed glucose (g/l) | Lactate (g/l) |
|---|---|---|---|
| SP1130 | 3.22 | 50.64 | 39.40 |
| SP1130 (Δ rim15) | 4.90 | 63.56 | 45.54 |
| SP1130 (Δ igo2) | 3.50 | 59.77 | 46.24 |

Referring to Table 1, the yield of lactate was increased in the SP1130(Δ rim15) and SP1130(Δ igo2) strains by about 15.58% and about 17.36%, respectively, with respect to the SP1130 strain as the control group. That is, the S. cerevisiae strains in which rim15 gene and/or igo2 gene were disrupted showed unexpectedly higher lactate productivities compared to the non-disrupted strain.

Figure 3:
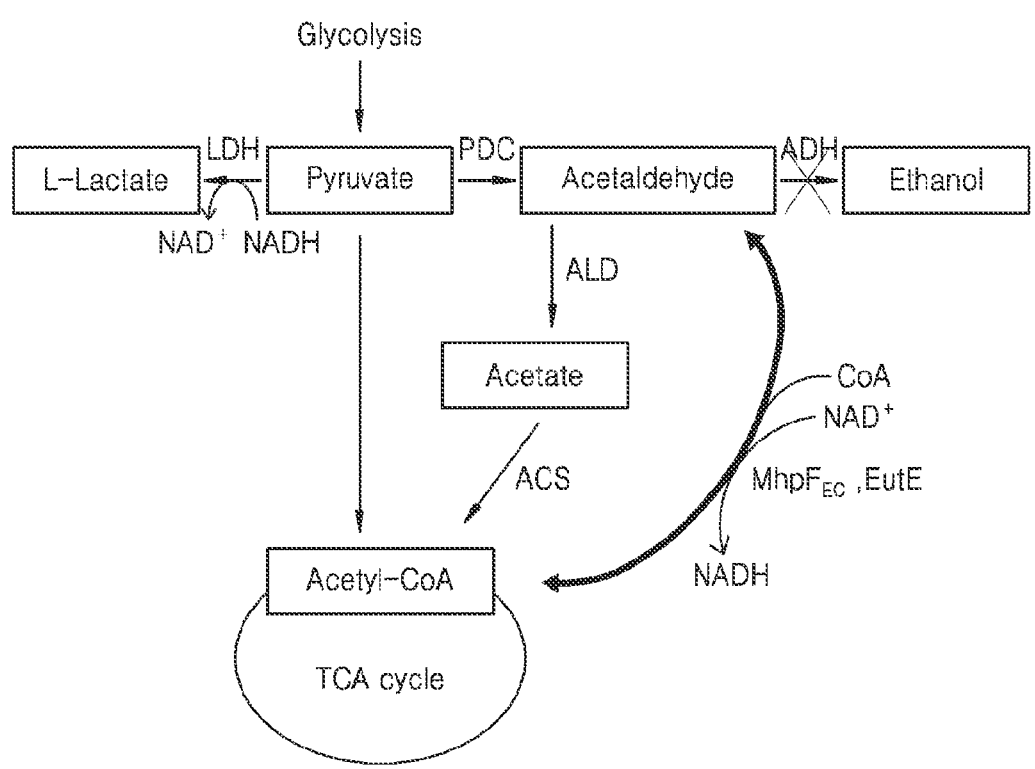
FIG. 3 illustrates an expected metabolic pathway associated with the conversion of pyruvate generated in the glycolysis pathway into lactate in S. cerevisiae CEN.PK2-1D SP1130 used as a parent strain in an example according to the present disclosure.

FIG. 3 illustrates an expected metabolic pathway associated with the conversion of pyruvate generated by glycolysis into lactate in S. cerevisiae CEN.PK2-1D SP1130 used as a parent strain in an example according to the present disclosure. In FIG. 3, $MhpF_{EC}$ indicates E. coli-derived exogenous acylating acetaldehyde dehydrogenase (A-ALD).

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present disclosure as defined by the following claims.

What is claimed is:

1. A recombinant yeast cell capable of producing lactate comprising:
   a genetic modification that reduces the activity of rim15 protein, igo2 protein, or any combination thereof, as compared to a parent yeast cell;
   and further comprising a genetic modification that increases the activity of an enzyme that catalyzes the conversion from pyruvate into lactate as compared to a parent yeast cell.

2. The recombinant yeast cell of claim 1, wherein the rim15 protein has an amino acid sequence of SEQ ID NO: 1, the igo2 protein has an amino acid sequence of SEQ ID NO: 3, and the enzyme catalyzing the conversion from pyruvate to lactate is a lactate dehydrogenase (LDH) classified as EC 1.1.2.27 or EC 1.1.1.28.

3. The recombinant yeast cell of claim 1 comprising a disruption mutation in a rim15 gene, igo2 gene, or a combination thereof, and comprises an exogenous gene that encodes an enzyme catalyzing the conversion from pyruvate to lactate.

4. The recombinant yeast cell of claim 1, wherein the yeast cell is a *Saccharomyces*, *Candida*, *Schizosaccharomyces*, *Kluyveromyces*, *Pichia*, *Issachenkia*, or *Hansenula* yeast cell.

5. The recombinant yeast cell of claim 1 further comprising a genetic modification that reduces the activity of an enzyme that catalyzes the conversion of acetaldehyde to ethanol, an enzyme that catalyzes the conversion of pyruvate to acetaldehyde, an enzyme that catalyzes the conversion of lactate to pyruvate, an enzyme that catalyzes the conversion of dihydroxyacetone phosphate (DHAP) to glycerol-3-phosphate (G3P), an enzyme that catalyzes the conversion of glycerol-3-phosphate (G3P) to glycerol, an enzyme that catalyzes the conversion of acetaldehyde to acetate, or a combination thereof, as compared to a parent yeast cell.

6. The recombinant yeast cell of claim 5, wherein the enzyme that catalyzes the conversion from acetaldehyde to ethanol belongs to EC 1.1.1.1, the enzyme that catalyzes the conversion from pyruvate to acetaldehyde belongs to EC 4.1.1.1, the enzyme that catalyzes the conversion from lactate to pyruvate belongs to EC 1.1.2.4 or EC 1.1.2.3, the enzyme that catalyzes the conversion from dihydroxyacetone phosphate (DHAP) to glycerol-3-phosphate (G3P) belongs to EC 1.1.1.8, the enzyme that catalyzes the conversion from glycerol-3-phosphate (G3P) to glycerol belongs to EC 3.1.3.21, the enzyme that catalyzes the conversion from acetaldehyde to acetate belongs to EC 1.2.1.4.

7. The recombinant yeast cell of claim 5, wherein the enzyme that catalyzes the conversion from acetaldehyde to ethanol is alcohol dehydrogenase (ADH), the enzyme that catalyzes the conversion from pyruvate to acetaldehyde is pyruvate decarboxylase (PDC), the enzyme that catalyzes the conversion from lactate to pyruvate is lactate cytochrome-c oxidoreductase (CYB2), the enzyme that catalyzes the conversion from dihydroxyacetone phosphate (DHAP) to glycerol-3-phosphate (G3P) is NAD-dependent glycerol-3-phosphate dehydrogenase (GPD), the enzyme that catalyzes the conversion from glycerol-3-phosphate (G3P) to glycerol is glycerol phosphate phosphatase (GPP), the enzyme that catalyzes the conversion from acetaldehyde to acetate is acetaldehyde dehydrogenase.

8. The recombinant yeast cell of claim 5, wherein the yeast cell comprises a disruption mutation of a gene that encodes the enzyme catalyzing the conversion from acetaldehyde to ethanol, a gene that encodes the enzyme catalyzing the conversion from pyruvate to acetaldehyde, a gene that encodes the enzyme catalyzing the conversion from lactate to pyruvate, a gene that encodes the enzyme catalyzing the conversion from dihydroxyacetone phosphate (DHAP) to glycerol-3-phosphate (G3P), a gene that encodes the enzyme catalyzing the conversion from glycerol-3-phosphate (G3P) to glycerol, a gene that encodes the enzyme catalyzing the conversion from acetaldehyde to acetate, or a combination thereof.

9. A method of producing lactate, the method comprising:
culturing the recombinant yeast cell of claim 1 in a culture medium to obtain a culture including lactate; and
separating lactate from the culture medium.

10. The method of claim 9, wherein the rim15 protein has an amino acid sequence of SEQ ID NO: 1, the igo2 protein has an amino acid sequence of SEQ ID NO: 3, and the enzyme catalyzing the conversion from pyruvate to lactate is a lactate dehygrogenase (LDH) classified as EC 1.1.2.27 or EC 1.1.1.28.

11. The method of claim 10, wherein the recombinant yeast cell comprises a disruption mutation of a rim15 gene, igo2 gene, or a combination thereof is disrupted, and the recombinant yeast cell further comprises an exogenous gene that encodes the enzyme that catalyzes the conversion of pyruvate to lactate.

12. The method of claim 9, wherein the recombinant yeast cell is a *Saccharomyces, Candida, Schizosaccharomyces, Kluyveromyces, Pichia, Issachenkia,* or *Hansenula* yeast cell.

13. The method of claim 9, wherein the recombinant yeast cell further comprises a genetic modification that reduces the activity of an enzyme that catalyzes the conversion of acetaldehyde to ethanol, an enzyme that catalyzes the conversion of pyruvate to acetaldehyde, an enzyme that catalyzes the conversion of lactate to pyruvate, an enzyme that catalyzes the conversion of dihydroxyacetone phosphate (DHAP) to glycerol-3-phosphate (G3P), an enzyme that catalyzes the conversion of glycerol-3-phosphate (G3P) to glycerol, an enzyme that catalyzes the conversion of acetaldehyde to acetate, or a combination thereof, as compared to a parent yeast cell.

14. The method of claim 13, wherein the enzyme that catalyzes the conversion of acetaldehyde to ethanol belongs to EC 1.1.1.1, the enzyme that catalyzes the conversion of pyruvate to acetaldehyde belongs to EC 4.1.1.1, the enzyme that catalyzes the conversion of lactate to pyruvate belongs to EC 1.1.2.4 or EC 1.1.2.3, the enzyme that catalyzes the conversion of dihydroxyacetone phosphate (DHAP) to glycerol-3-phosphate (G3P) belongs to EC 1.1.1.8, the enzyme that catalyzes the conversion of glycerol-3-phosphate (G3P) to glycerol belongs to EC 3.1.3.21, the enzyme that catalyzes the conversion of acetaldehyde to acetate belongs to EC 1.2.1.4.

15. The method of claim 13, wherein the enzyme that catalyzes the conversion of acetaldehyde to ethanol is alcohol dehydrogenase (ADH), the enzyme that catalyzes the conversion of pyruvate to acetaldehyde is pyruvate decarboxylase (PDC), the enzyme that catalyzes the conversion of lactate to pyruvate is lactate cytochrome-c oxidoreductase (CYB2), the enzyme that catalyzes the conversion of dihydroxyacetone phosphate (DHAP) to glycerol-3-phosphate (G3P) is NAD-dependent glycerol-3-phosphate dehydrogenase (GPD), the enzyme that catalyzes the conversion of glycerol-3-phosphate (G3P) to glycerol is glycerol phosphate phosphatase (GPP), the enzyme that catalyzes the conversion of acetaldehyde to acetate is acetaldehyde dehydrogenase.

16. The method of claim 13, wherein the recombinant yeast cell comprises a disruption mutation in a gene that encodes the enzyme that catalyzes the conversion of acetaldehyde to ethanol, a gene that encodes the enzyme that catalyzes the conversion of pyruvate to acetaldehyde, a gene that encodes the enzyme that catalyzes the conversion of lactate to pyruvate, a gene that encodes the enzyme that catalyzes the conversion of dihydroxyacetone phosphate (DHAP) to glycerol-3-phosphate (G3P), a gene that encodes the enzyme that catalyzes the conversion of glycerol-3-phosphate (G3P) to glycerol, a gene that encodes the enzyme that catalyzes the conversion of acetaldehyde to acetate, or a combination thereof.

17. The method of claim 9, wherein the culturing is performed in a range from about pH 3 to about pH 5.

18. The method of claim 9, wherein the culturing is performed under a microaerobic condition.

19. A method of producing a recombinant yeast cell that produces lactate comprising:
introducing into a yeast cell a gene that encodes an enzyme catalyzing conversion from pyruvate to lactate; and
disrupting in the yeast cell a gene that encodes rim15 protein, a gene that encodes igo2 protein, or both a gene that encodes rim15 protein and a gene that encodes igo2 protein.

* * * * *

SEQUENCE LISTING

<160> NUMBER OF SEQ ID NOS: 88

<210> SEQ ID NO 1
<211> LENGTH: 1770
<212> TYPE: PRT
<213> ORGANISM: Saccharomyces cerevisiae S288c rim15p

<400> SEQUENCE: 1

Met Phe Asn Arg Ser Asn Thr Ala Gly Gly Ser Gln Ala Met Lys Glu

```
                1               5                    10                   15
            Gly Leu Gly Ile Asn Lys Leu Ser Pro Ile Ser Ser Asn Ser Asn Pro
                        20                  25                  30
            Ser Ser Leu Thr Ser Ser Asn Tyr Glu Lys Tyr Leu Gln Leu Ala Thr
                        35                  40                  45
            Glu Lys Asn Pro Cys Met Ile Leu Glu Leu Glu Leu Asp Gly Lys Val
                50                  55                  60
            Arg Tyr Gly Ser Pro Gln Trp Asn Thr Ile Thr Gly Val Ala Asp Asp
             65                  70                  75                  80
            Ser Gly Ser Ser Pro Thr Tyr Ile Ala Asp Leu Ile Leu Gly Ser Asp
                        85                  90                  95
            Gln Asp Lys Gly Val Phe Gln Lys Ala Thr Asp Met Leu Leu Met Asn
                        100                 105                 110
            Asp Asp Thr Ser Cys Thr Ile Thr Phe Lys Ile Lys Ala Ala Asp Tyr
                        115                 120                 125
            Glu Gly Ser Ala Gly Cys Asp Asp Glu Ser Thr Ile Thr Thr Leu Glu
                        130                 135                 140
            Ala Arg Gly Ile Leu Ile Arg Asp Gly His Thr Gln Leu Pro Ser His
            145                 150                 155                 160
            Thr Met Trp Ile Val Lys Pro Arg Thr Asn Asp Trp Ser Asp Phe Tyr
                                165                 170                 175
            Ala Asn Glu Asp Ala Gln Asp Met Val Ile Gln Leu Ser Asp Asn
                        180                 185                 190
            Cys Asp Asp Ile Asp Ile Gln Leu Pro Glu Glu Phe Ala Lys Thr Leu
                        195                 200                 205
            Gly Phe Gly Ala Lys Ile Phe Val Gln Tyr Leu Lys Arg Ile Arg Leu
                        210                 215                 220
            Glu Met Ile Ile Asp Glu Phe Asn Leu Pro Leu Pro Lys Met Glu Leu
            225                 230                 235                 240
            Cys Arg Val Cys Glu Asn Phe Val Pro Val Trp Trp Leu Glu Thr His
                                245                 250                 255
            Ser Gln Ser Cys Val Cys Glu His Arg Thr Glu Ser Leu Ile Gln Leu
                        260                 265                 270
            Leu His Asp Asn Leu Leu Glu Gln Gln Ala Ile Leu Ala Asn Phe Thr
                        275                 280                 285
            Lys Asp Ser Glu Tyr Lys Gly Ser Gln Ile Gln Val Arg Ser Asn Asn
                        290                 295                 300
            Phe Leu Asn Gln Val Leu Asp Ser Leu Arg Glu Leu Cys Gln Asp Ala
            305                 310                 315                 320
            Ile Asp Ile Asn Pro Ser Glu Met Val Pro Asp Leu Tyr His Ser Leu
                                325                 330                 335
            Ser Thr Phe Pro Gln Asp Asn Gly Asn Asn Asn Asn Asn Asn Asn Asn
                        340                 345                 350
            Asn Asn Asn Asn Asn Ala Leu Leu Asp Gln Phe Pro Ile Gln Lys
                        355                 360                 365
            Asp Thr Val Ser Leu Asn Ser Tyr Phe Gln Phe Ser Pro Arg Thr Asn
                        370                 375                 380
            His Asn Ile Gln Asn Val Thr Ser Trp Gln Ser Arg Phe Phe Leu Asn
            385                 390                 395                 400
            Asp Asp Gln Asp Pro Gly Leu Ala Leu Leu Ile His Asp Thr Leu Asp
                        405                 410                 415
            Leu Ala Arg Lys Lys Val Asp Ala Val Leu Arg Leu Asp Asn Ala Met
                        420                 425                 430
```

```
Thr Tyr Ser Leu Lys Ile Lys Asn Glu Val Asn Tyr Val Val Gln
        435                 440                 445
Leu Ile Arg Glu Gln Ile Glu Ile Asn Lys His Ala Ile Leu Thr His
    450                 455                 460
Pro Met Asn Leu Arg Ser Ser Ile Phe His Ser Pro Leu Pro Gln
465                 470                 475                 480
Ile His Ser Gln Gln Pro Glu Ala Glu Asn Leu Ile Tyr Ser Ser
                485                 490                 495
Thr Pro Leu Gln Val Gln His Asp Gln Cys Ala Ser Phe Glu Ala Pro
            500                 505                 510
Ser Lys Ser His Leu Glu Pro Ile Pro Phe Pro Val Ser Ser Ile Glu
        515                 520                 525
Glu Thr Pro Thr Ala Asn Asp Ile Arg His Pro Ser Pro Leu Pro Arg
    530                 535                 540
Ser Cys Ser Asn Thr Val Met Lys Leu Pro Thr Pro Arg Arg Lys Leu
545                 550                 555                 560
Asp Ser Asn Gly Leu Phe Ser Asp Ala Tyr Leu Asn Ala Asp Ile Ile
                565                 570                 575
Pro Asn Pro Ser Ile Glu Ser Thr Ile Ser Ile Asp Arg Asp Asn Asn
            580                 585                 590
Thr Asn Ser Arg Gly Ser Ser Met Lys Gln Tyr Gly Ile Gly Glu Ala
        595                 600                 605
Thr Asp Ser Arg Thr Ser Asn Ser Glu Arg Pro Ser Ser Ser Ser Ser
    610                 615                 620
Arg Leu Gly Ile Arg Ser Arg Ser Ile Thr Pro Arg Gln Lys Ile Glu
625                 630                 635                 640
Tyr Ser His Val Asp Asn Asp Arg Thr Asn Glu Met Leu Ser Arg
                645                 650                 655
Asp Lys Asp Ser Leu Gln Pro Gln Pro Ser Val Asp Thr Thr Ile Thr
            660                 665                 670
Ser Ser Thr Gln Ala Thr Thr Thr Gly Thr Lys Thr Asn Ser Asn Asn
        675                 680                 685
Ser Thr Asn Ser Val Leu Pro Lys Leu Met Thr Ser Ile Ser Leu Thr
    690                 695                 700
Pro Arg Arg Gly Ser Pro Ser Phe Gly Asn Leu Ala Ser His Ser Met
705                 710                 715                 720
Gln Gln Thr Asn Ser Phe Lys Leu Ile His Asp Lys Ser Pro Ile Ser
                725                 730                 735
Ser Pro Phe Thr Phe Ser Lys Asp Phe Leu Thr Pro Glu Gln His Pro
            740                 745                 750
Ser Asn Ile Ala Arg Thr Asp Ser Ile Asn Asn Ala Met Leu Thr Ser
        755                 760                 765
Pro Asn Met Pro Leu Ser Pro Leu Leu Leu Ala Thr Asn Gln Thr Val
    770                 775                 780
Lys Ser Pro Thr Pro Ser Ile Lys Asp Tyr Asp Ile Leu Lys Pro Ile
785                 790                 795                 800
Ser Lys Gly Ala Tyr Gly Ser Val Tyr Leu Ala Arg Lys Lys Leu Thr
                805                 810                 815
Gly Asp Tyr Phe Ala Ile Lys Val Leu Arg Lys Ser Asp Met Ile Ala
            820                 825                 830
Lys Asn Gln Val Thr Asn Val Lys Ser Glu Arg Ala Ile Met Met Val
        835                 840                 845
```

```
Gln Ser Asp Lys Pro Tyr Val Ala Arg Leu Phe Ala Ser Phe Gln Asn
    850                 855                 860

Lys Asp Asn Leu Phe Leu Val Met Glu Tyr Leu Pro Gly Gly Asp Leu
865                 870                 875                 880

Ala Thr Leu Ile Lys Met Met Gly Tyr Leu Pro Asp Gln Trp Ala Lys
                885                 890                 895

Gln Tyr Leu Thr Glu Ile Val Val Gly Val Asn Asp Met His Gln Asn
            900                 905                 910

Gly Ile Ile His His Asp Leu Lys Pro Glu Asn Leu Leu Ile Asp Asn
                915                 920                 925

Ala Gly His Val Lys Leu Thr Asp Phe Gly Leu Ser Arg Ala Gly Leu
    930                 935                 940

Ile Arg Arg His Lys Phe Val Pro His Lys Ser Ser Leu Ser Ile Ser
945                 950                 955                 960

Ser Thr Leu Pro Ile Asp Asn Pro Ala Asn Asn Phe Thr Met Asn Asn
                965                 970                 975

Asn Asn Ser Asn His Ser Gln Leu Ser Thr Pro Asp Ser Phe Thr Ser
            980                 985                 990

Asp His Lys Gln Tyr Asn Arg Ser Lys Lys Ser Ser Leu Gly Gln Gln
    995                 1000                1005

Tyr Glu His Ser Glu Tyr Ser Ser Thr Ser Asn Ser His Ser Met Thr
    1010                1015                1020

Pro Thr Pro Ser Thr Asn Thr Val Val Tyr Pro Ser Tyr Tyr Arg Gly
1025                1030                1035                1040

Lys Asp Arg Ser His Gly Ser Ser Asn Ile Asp Leu Pro Ala Ser Leu
                1045                1050                1055

Arg Arg Ser Glu Ser Gln Leu Ser Phe Ser Leu Leu Asp Ile Ser Arg
            1060                1065                1070

Ser Ser Thr Pro Pro Leu Ala Asn Pro Thr Asn Ser Asn Ala Asn Asn
    1075                1080                1085

Ile Met Arg Arg Lys Ser Leu Thr Glu Asn Lys Ser Phe Ser Asn Asp
    1090                1095                1100

Leu Leu Ser Ser Asp Ala Ile Ala Ala Thr Asn Thr Asn Ile Asn Ser
1105                1110                1115                1120

Asn Asn Asn Ile Ser Leu Ser Pro Ala Pro Ser Asp Leu Ala Leu Phe
                1125                1130                1135

Tyr Pro Asp Asp Ser Lys Gln Asn Lys Lys Phe Phe Gly Thr Pro Asp
            1140                1145                1150

Tyr Leu Ala Pro Glu Thr Ile Glu Gly Lys Gly Glu Asp Asn Lys Gln
    1155                1160                1165

Cys Asp Trp Trp Ser Val Gly Cys Ile Phe Phe Glu Leu Leu Leu Gly
    1170                1175                1180

Tyr Pro Pro Phe His Ala Glu Thr Pro Asp Ala Val Phe Lys Lys Ile
1185                1190                1195                1200

Leu Ser Gly Val Ile Gln Trp Pro Glu Phe Lys Asn Glu Glu Glu Glu
                1205                1210                1215

Arg Glu Phe Leu Thr Pro Glu Ala Lys Asp Leu Ile Glu Lys Leu Leu
            1220                1225                1230

Val Val Asp Pro Ala Lys Arg Leu Gly Ala Lys Gly Ile Gln Glu Ile
    1235                1240                1245

Lys Asp His Pro Tyr Phe Lys Asn Val Asp Trp Asp His Val Tyr Asp
    1250                1255                1260

Glu Glu Ala Ser Phe Val Pro Thr Ile Asp Asn Pro Glu Asp Thr Asp
```

-continued

```
            1265                1270                1275                1280

Tyr Phe Asp Leu Arg Gly Ala Glu Leu Gln Asp Phe Gly Asp Asp Ile
                1285                1290                1295

Glu Asn Asp Asn Ala Asn Ile Leu Phe Gly Lys His Gly Ile Asn Thr
        1300                1305                1310

Asp Val Ser Glu Leu Ser Ala Ala Asn Leu Ser Pro Pro Leu Asn His
        1315                1320                1325

Lys Asn Ile Leu Ser Arg Lys Leu Ser Met Ser Asn Thr Thr Asn Arg
        1330                1335                1340

Ser Ser Asn Asn Ser Asn Ser Ser Val His Asp Phe Gly Ala His Thr
    1345                1350                1355                1360

Pro Val Asn Lys Leu Ser Ile Ala Ser Val Leu Glu Ser Val Pro Gln
            1365                1370                1375

Glu Thr Gly Tyr Ile Thr Pro Asn Gly Thr Gly Thr Thr Thr Thr Ser
            1380                1385                1390

Ala Lys Asn Ser Pro Asn Leu Lys Asn Leu Ser Leu Ala Ile Pro Pro
        1395                1400                1405

His Met Arg Asp Arg Arg Ser Ser Lys Leu Asn Asp Ser Gln Thr Glu
    1410                1415                1420

Phe Gly Ser Phe Asn Phe Arg Asn Leu Ser Ala Leu Asp Lys Ala Asn
1425                1430                1435                1440

Lys Asp Ala Ile Asn Arg Leu Lys Ser Glu His Phe Ser Glu Gln Pro
            1445                1450                1455

Gly Val His Arg Arg Thr Ser Ser Ala Ser Leu Met Gly Ser Ser Ser
            1460                1465                1470

Asp Gly Ser Val Ser Thr Pro Gly Ser Asn Ala Ser Asn Thr Thr Ser
        1475                1480                1485

Gly Gly Lys Leu Lys Ile His Lys Pro Thr Ile Ser Gly Ser Pro Ser
        1490                1495                1500

Thr Phe Gly Thr Phe Pro Lys Thr Phe Leu Arg Ser Asp Ser Phe Ser
1505                1510                1515                1520

Thr Arg Ser Tyr Ser Pro Glu Arg Ser Ile Ser Ile Asp Ser Ser Thr
            1525                1530                1535

Leu Ser Arg Lys Gly Ser Ile Ile Gly Asp Asn Gln Gln Thr Thr Ala
            1540                1545                1550

Asn Ser Ser Asp Ser Pro Thr Met Thr Lys Phe Lys Ser Pro Leu Ser
        1555                1560                1565

Pro Ala Asn Thr Thr Thr Val Ser Ser Tyr Phe Ser Arg Gln Arg Val
        1570                1575                1580

Leu Ser Lys Ser Phe Ser Gln Arg Thr Asn Ser Ser Asp Leu Ser Ala
1585                1590                1595                1600

Glu Glu Ser Asp Arg Leu Gln Ala Ile Ser Arg Val Asn Ser Leu Arg
            1605                1610                1615

Asn Arg Arg Arg Ser Gly Arg Lys Ser Ser Ser Thr Ser Glu Ile Gly
            1620                1625                1630

Tyr His Met Asp Val Leu Val Cys Glu Pro Ile Pro Ile His Arg Tyr
        1635                1640                1645

Arg Val Thr Lys Asp Leu Glu Asn Leu Gly Cys Thr Val Val Ser Val
    1650                1655                1660

Gly Ala Gly Asp Glu Leu Val Ser Arg Ala Thr Ser Gly Val Ser Phe
1665                1670                1675                1680

Asp Leu Ile Met Thr Ala Leu Lys Leu Pro Lys Leu Gly Ala Ile Asp
            1685                1690                1695
```

Ile Val Gln Leu Leu Lys Gln Thr Asn Gly Ala Asn Ser Thr Thr Pro
        1700                1705                1710

Ile Val Ala Ile Thr Asn Tyr Phe Gln Glu Ala Ala Thr Ser Arg Val
    1715                1720                1725

Phe Asp Asp Val Leu Glu Lys Pro Val Lys Leu Asp Glu Leu Lys Lys
    1730                1735                1740

Leu Val Ala Lys Tyr Ala Leu Lys Lys Ser Gln Glu Asp Glu His
1745                1750                1755                1760

Thr Ile Leu Ser Asp Ser Asp Glu Thr His
        1765                1770

<210> SEQ ID NO 2
<211> LENGTH: 5313
<212> TYPE: DNA
<213> ORGANISM: Saccharomyces cerevisiae S288c Rim15p gene

<400> SEQUENCE: 2

| | | | | |
|---|---|---|---|---|
| atgttcaata | gaagtaacac | cgcaggcgga | tctcaggcta | tgaaagaggg  acttggcata | 60 |
| aacaagctct | ccccgatatc | atcgaattcg | aacccaagct | cattgacttc  ctccaattat | 120 |
| gaaaaatatc | tgcagctggc | cacagagaag | aatccgtgta | tgatcttgga  gctggaactg | 180 |
| gacggcaagg | tgcgatatgg | ctctccacag | tggaacacga | tcacaggagt  cgccgatgat | 240 |
| agtggctctt | ctccgacgta | cattgcagac | cttattctcg | gatccgatca  agataaaggt | 300 |
| gtctttcaaa | aggccacaga | catgctgctc | atgaatgatg | acaccagttg  cactataacg | 360 |
| ttcaagataa | aggcagccga | ctatgaaggt | agcgcaggct | gtgacgatga  agtacgata | 420 |
| acgaccttgg | aagcacgtgg | tatcttaatc | agggatggcc | acacacagtt  gccctctcac | 480 |
| acgatgtgga | tagtcaagcc | tcgcacaaac | gactggtcag | acttttatgc  caacgaagac | 540 |
| gctcaagacg | acatggtcat | ccagttatcc | gataattgcg | acgatatcga  tatccaactt | 600 |
| cccgaagagt | tcgccaagac | gcttgggttc | ggcgctaaga | tcttcgtgca  gtacttgaag | 660 |
| agaatacgac | tggaaatgat | aatagacgag | ttcaatctac | ctctgccaaa  aatggaacta | 720 |
| tgccgggtct | gtgagaactt | tgtccctgtt | tggtggttgg | agacccattc  gcaaagttgc | 780 |
| gtttgcgagc | atagaacgga | atcgctcata | caattactac | acgataatct  tcttgagcaa | 840 |
| caggcgatct | tggcaaactt | cacgaaagat | tcagagtata | agggcagtca  gatacaggta | 900 |
| cgttccaaca | acttccttaa | ccaagtttta | gactccttaa | gagagctgtg  tcaggacgcc | 960 |
| atagatatca | cccgagtgga | aatggttcct | gatctttacc | acagtctttc  aacatttcct | 1020 |
| caagataatg | gtaataataa | caataataat | aataataata | ataataataa  caatgctttg | 1080 |
| ttagatcaat | tccctatcca | aaaagataca | gttagcttga | attcatattt  tcagttttcc | 1140 |
| ccaaggacta | accacaacat | tcaaaacgtc | acgtcgtggc | aatcaagatt  ttttctcaat | 1200 |
| gatgatcagg | atcctggact | agctcttttg | attcacgata | ctctggactt  ggcaaggaaa | 1260 |
| aaagtggatg | ccgtgttgag | gttggataac | gcaatgacct | attctttaaa  gattaaaaac | 1320 |
| gaggtcaaca | actatgtggt | acaactgatc | cgcgagcaaa | ttgaaataaa  taagcatgca | 1380 |
| atcctaactc | acccaatgaa | tttaaggtct | tcttccatat | tcattccccc  actgccgcaa | 1440 |
| attcactctc | aacaaccaga | agccgagaat | ctcatatatt | cctcctctac  tcccctgcaa | 1500 |
| gtccaacacg | accaatgtgc | gtcctttgaa | gcaccctcca | agtctcatct  ggagcctatt | 1560 |
| cctttccccgg | tttcttccat | tgaagaaaca | ccaactgcaa | atgatatcag  gcatccttct | 1620 |
| cctttgccccc | gtagttgtag | caacaccgtt | atgaaactac | cgacacctcg  aaggaaactt | 1680 |

```
gactcaaacg gattattctc tgatgcctat ttaaacgctg acatcattcc gaacccaagt    1740
atcgaatcca cgatatctat tgatagagat aataacacta atagtagggg tagtagtatg    1800
aaacagtatg gtattggtga agccaccgac tctcggacta gtaactcgga agaccttct    1860 tcctcttcgt caaggctggg gataagatca agatccataa caccaagaca aaagatagaa    1920
tactcacatg tagataatga tgaccgcacc aacgaaatgc tgtctagaga taaagattct    1980
cttcaacctc aaccttccgt agataccacc ataacatcct ctactcaggc gaccaccacg    2040
ggtaccaaga ctaatagtaa caattccaca aactcagtat taccaaaact aatgacaagt    2100
atttccttga ccccaaggcg tggttcacca tcatttggta atctcgcaag ccattctatg    2160
cagcagacaa acagttttaa actgattcat gataaatcgc cgatatcttc accttttcaca   2220 ttctccaagg atttttaac cccagagcag caccccttcca atattgccag aacagatagt    2280
atcaataatg caatgttaac ttcaccgaat atgccattat caccccttttt attggccaca   2340 aaccaaaactt taaatctcc aacgcctagc ataaaagatt acgatatctt gaaaccaatc    2400
agcaaaggtg cttatggtag tgtttatcta gcacggaaaa aactcacagg agattatttt    2460
gctataaagg ttctaaggaa atcagatatg attgccaaaa atcaagtaac aaatgtcaaa    2520
tccgagagag caatcatgat ggttcaaagt gataagccct atgttgcgag actatttgct    2580
agtttccaaa ataaagataa ccttttctta gtgatgaat attaccagg tggagattttg    2640 gccactttaa tcaagatgat ggggtatctg cccgatcaat gggccaagca atacctaacc    2700
gaaatcgttg tcggtgtgaa tgatatgcat caaaatggga tcattcatca tgacttaaag    2760
cctgaaaatc tactaattga taatgcaggt catgtgaaat aacagattt cggttttatca    2820 agagctggtc tgattcgccg tcacaagttt gtcccacata agtcgtcgct aagtatcagt    2880
tccactttac caatcgataa cccagcaaat aattttacca tgaacaacaa caatagtaat    2940
cattctcaat tatcaacccc agatagcttc acatcagatc ataagcagta taatagaagc    3000
aagaagtcat cactaggtca gcaatacgaa cactcagaat actcaagtac ttccaattcc    3060
cactcaatga cgccaacgcc cagtacgaac actgttgttt atccttcata ttaccgtggg    3120
aaggacagat cacacggaag ttcgaacatc gatctcccag cgtcccttag aagaagtgaa    3180
tctcaattat cattttccct ccttgatatt tctcgttcta gtactcctcc tttagcaaat    3240
cccacaaatt cgaacgctaa taatattatg agaaggaaat cactcactga gaataaatcc    3300 tttttctaatg acctattatc ttcagatgct atcgcagcta ccaatacgaa tattaactcg    3360
aataataaca tttcccttttc gccagcacct tcggatttag ctttgttta tcctgatgat    3420 agcaagcaaa ataagaaatt ttttgggact cccgattatc tcgctccaga aactattgaa    3480
ggaaagggtg aagataacaa gcaatgcgac tggtggtcag ttggttgtat attttttcgaa   3540 ttactttttag ggtatcctcc attccatgca gaaacaccag atgctgtttt taagaaaatt    3600
ctatcaggag tcattcaatg gccagagttt aaaaatgaag aagaagagcg agaattccta    3660
acaccagagg caaaagattt gatagaaaaa ttgttggttg tggatcctgc gaaaagactg    3720
ggtgcgaaag gaattcaaga aattaaagat caccccttatt tcaagaatgt ggattgggat    3780
catgtttacg atgaggaagc ttcttttgtc cctacaatag acaatccaga agatactgat    3840
tattttgacc taaggggtgc agagctccaa gattttggag acgatatcga aaacgataat    3900
gccaatattt tgtttggtaa acatggcatt aacaccgatg tttctgaatt atctgcagct    3960
aatctctctc caccattgaa tcataaaaat attttatccc gtaaactatc gatgagtaac    4020
```

```
accactaata ggagctcaaa taattccaac agtagcgtgc atgactttgg tgcacataca    4080
ccggttaata aattaagtat tgcttctgta ttagagtcag tacctcaaga aacaggatat    4140
attacaccta acgggaccgg tacaactact acaagtgcca aaaactcacc caatctgaag    4200
aatttgtcac tggctatacc tccacatatg agggatcgca gatcaagtaa attgaatgat    4260
tcacaaacgg aatttggttc ttttaatttc aggaatttat cggctcttga taaagctaat    4320
aaagatgcta taaatagact gaaaagtgaa cattttttctg aacaacctgg ggttcacaga    4380
agaacctctt ctgcgtcact aatggggtca tcctcagacg gatcagtgtc aactccaggg    4440
agtaacgctt caaacactac atctggtggc aagttgaaaa tacataagcc taccatatcc    4500
ggttctcctt caacatttgg cacatttccc aaaacatttt tgaggtctga ttcattctcc    4560
acaagatcat attctcctga acgaagtatt agtatcgact cgtcaacatt atcaaggaag    4620
ggtagtataa tcggggataa ccaacaaaca acagcaaata gctcggattc acctacgatg    4680
actaaattca agtcgccact atcacctgct aataccacca ccgtgagctc atattttttca    4740
agacagaggg ttctatcaaa gagttttttcg caacggacca attccagtga tctctcggca    4800
gaggaaagcg accgactaca ggctatatca agagttaact ctttaagaaa caggaggcgt    4860
agtggccgaa agagctcgag cacttctgag attggatacc acatggatgt tcttgtttgt    4920
gagcctatac cgattcatag atatcgggtt actaaagact tagaaaattt gggctgtacc    4980
gtcgtcagtg ttggtgccgg tgatgaacta gttagtagag ccactagtgg tgtaagtttt    5040
gacttaatta tgacagcctt gaagcttcca aaacttggtg ctattgacat tgttcaacta    5100
ctaaagcaaa caaatggtgc taattcgaca acaccaattg tggccataac aaattattttt   5160
caggaggcgg caaccagtag agtctttgac gatgtttttag aaaaaccggt aaaacttgac    5220
gagctaaaaa aattggtggc taagtacgca ctgaaaaagt ctcaagaaga tgaagagcat    5280
actatattga gcgattctga tgaaacgcac tga                                 5313
```

<210> SEQ ID NO 3
<211> LENGTH: 131
<212> TYPE: PRT
<213> ORGANISM: Saccharomyces cerevisiae S288c Igo2p

<400> SEQUENCE: 3

```
Met Ser Glu Asp Leu Ser Pro Thr Ser Ser Arg Val Asp Leu Ser Asn
  1               5                  10                  15

Pro His Gly Phe Thr Lys Glu Gly Val Asp Leu Ser Lys Leu Ser Pro
             20                  25                  30

Gln Glu Leu Lys Leu Tyr Lys Met Tyr Gly Lys Leu Pro Ser Lys Lys
         35                  40                  45

Asp Leu Leu Arg His Lys Met Gln Asp Arg Gln Tyr Phe Asp Ser Gly
     50                  55                  60

Asp Tyr Ala Leu Lys Lys Ala Gly Val Ile Lys Ser Asp Asp Val Ile
 65                  70                  75                  80

Val Asn Asn Ser Ser Asn Asn Leu Pro Val Thr Asn Pro Ser Gly Leu
                 85                  90                  95

Arg Glu Ser Ile Ile Arg Arg Arg Met Ser Ser Ser Gly Gly Asp
            100                 105                 110

Ser Ile Ser Arg Gln Gly Ser Ile Ser Ser Gly Pro Pro Arg Ser
        115                 120                 125

Pro Asn Lys
    130
```

<210> SEQ ID NO 4
<211> LENGTH: 396
<212> TYPE: DNA
<213> ORGANISM: Saccharomyces cerevisiae S288c Igo2p gene

<400> SEQUENCE: 4

```
atgtcagagg atctttcacc tacaagcagc agggtggatt tgagcaatcc tcatgggttt      60
accaaagagg gagtggattt atcgaagctg tcaccacaag aactaaaatt gtataaaatg     120
tatgggaagc ttccatccaa aaagatctg ttaagacata agatgcagga tcgtcaatat     180
tttgacagcg gagattatgc attgaaaaag gccggagtca ttaagtcgga tgacgttatc     240
gtgaataatt ctagtaataa tctaccagtg accaatccta gcggtttaag agagtctatt     300
attagaagac gtatgagtag tagtagtggt ggcgattcta tctcgagaca aggaagtatc     360
tcaagtggac ctccaccaag atctccaaat aaatga                              396
```

<210> SEQ ID NO 5
<211> LENGTH: 332
<212> TYPE: PRT
<213> ORGANISM: Pelodiscus sinensis japonicus LDH protein

<400> SEQUENCE: 5

```
Met Ser Val Lys Glu Leu Leu Ile Gln Asn Val His Lys Glu Glu His
  1               5                  10                  15

Ser His Ala His Asn Lys Ile Thr Val Val Gly Val Gly Ala Val Gly
                 20                  25                  30

Met Ala Cys Ala Ile Ser Ile Leu Met Lys Asp Leu Ala Asp Glu Leu
         35                  40                  45

Ala Leu Val Asp Val Ile Glu Asp Lys Leu Arg Gly Glu Met Leu Asp
     50                  55                  60

Leu Gln His Gly Ser Leu Phe Leu Arg Thr Pro Lys Ile Val Ser Gly
 65                  70                  75                  80

Lys Asp Tyr Ser Val Thr Ala His Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
```

Ile Ser Thr Met Val Lys Gly Met Tyr Gly Val Ser Ser Asp Val Phe
            260                 265                 270

Leu Ser Val Pro Cys Val Leu Gly Tyr Ala Gly Ile Thr Asp Val Val
        275                 280                 285

Lys Met Thr Leu Lys Ser Glu Glu Glu Lys Leu Arg Lys Ser Ala
290                 295                 300

Asp Thr Leu Trp Gly Ile Gln Lys Glu Leu Gln Phe
305                 310                 315                 320

325                 330

<210> SEQ ID NO 6
<211> LENGTH: 999
<212> TYPE: DNA
<213> ORGANISM: Pelodiscus sinensis japonicus LDH gene

<400> SEQUENCE: 6
atgtccgtaa aggaactact tatacaaaac gtccataagg aggagcattc tcacgctcac      60
aataagataa cagttgtagg agtaggtgca gtaggtatgg catgtgctat ttcgatatta    120
atgaaagact ggctgatga actagccttg gttgatgtga ttgaggataa gttacgtgga    180
gaaatgttag atttgcaaca tggttcattg ttcttgagaa cccccaaaat tgtctcgggt    240
aaggattatt cagtcactgc tcattctaaa ctggttatca ttacagcagg tgcaagacag    300
caagaagggg agagcagact aaatctggtt caacgtaatg tcaacatctt caagtttatc    360
atcccgaacg tagtaaaata cagtccagac tgcatgttgc ttgttgtgag taatccagtt    420
gacatcttaa cctatgttgc gtggaaaatc agtgggtttc aaaacatag gtgattggc     480
tcaggatgca accttgatag cgccaggttt aggtatctaa tgggagaaaa attaggtatt    540
cactccttat cttgtcatgg ctggataata ggcgaacatg gtgattcttc ggtacctgtt    600
tggtccgggg ttaatgtggc tggtgttagt ttaaaagcat tatatcctga cctgggtact    660
gatgccgata agaacattg gaaagaagtg cacaaacaag tggttgattc tgcttacgaa    720
gttattaaac ttaagggcta cacttcttgg gctataggtc tatcagtagc tgatttggca    780
gaaaccgtta tgaaaaattt aagaagagtc cacccaattt ccacgatggt caagggtatg    840
tacggtgtta gctctgacgt cttcttatct gttccttgtg ttttgggata tgcgggaatt    900
acagacgtcg tgaagatgac attgaaatca gaggaagagg aaaaactaag aaagtcagcc    960
gatactctgt ggggcattca aaaggaattg cagttttaa                           999

<210> SEQ ID NO 7
<211> LENGTH: 332
<212> TYPE: PRT
<213> ORGANISM: Ornithorhynchus anatinus LDH protein

<400> SEQUENCE: 7

Met Ala Gly Val Lys Glu Gln Leu Ile Gln Asn Leu Leu Lys Glu Glu
1               5                   10                  15

Tyr Ala Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

```
Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
            115                 120                 125

Pro Asn Cys Lys Leu Leu Val Val Ser Asn Pro Val Asp Ile Leu Thr
        130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
            180                 185                 190

His Gly Asp Ser Ser Val Pro Val Trp Ser Gly Val Asn Val Ala Gly
            195                 200                 205

Val Ser Leu Lys Asn Leu His Pro Asp Leu Gly Thr Asp Ala Asp Lys
        210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
            275                 280                 285

Leu Ser Val Pro Cys Val Leu Gly Gln Asn Gly Ile Ser Asp Val Val
        290                 295                 300

Lys Ile Thr Leu Lys Ser Glu Glu Ala His Leu Lys Lys Ser Ala
305                 310                 315                 320

Asp Thr Leu Trp Gly Ile Gln Lys Glu Leu Gln Phe
                325                 330

<210> SEQ ID NO 8
<211> LENGTH: 332
<212> TYPE: PRT
<213> ORGANISM: Tursiops truncates LDH protein

<400> SEQUENCE: 8

Met Ala Thr Val Lys Asp Gln Leu Ile Gln Asn Leu Leu Lys Glu Glu
1               5                   10                  15

His Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65              70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
            115                 120                 125
```

```
Pro His Cys Lys Leu Leu Val Ser Asn Pro Val Asp Ile Leu Thr
    130                 135                 140
Tyr Val Ala Trp Lys Ile Ser Gly Phe Pro Lys Asn Arg Val Ile Gly
145                 150                 155                 160
Ser Gly Cys Asn Leu Asp Ser Ala Arg Phe Arg Tyr Leu Met Gly Glu
                165                 170                 175
Arg Leu Gly Val His Pro Leu Ser Cys His Gly Trp Ile Leu Gly Glu
            180                 185                 190
His Gly Asp Ser Ser Val Pro Val Trp Ser Gly Val Asn Val Ala Gly
        195                 200                 205
Val Ser Leu Lys Asn Leu His Pro Glu Leu Gly Thr Asp Ala Asp Lys
    210                 215                 220
Glu His Trp Lys Ala Ile His Lys Gln Val Val Asp Ser Ala Tyr Glu
225                 230                 235                 240
Val Ile Lys Leu Lys Gly Tyr Thr Ser Trp Ala Val Gly Leu Ser Val
                245                 250                 255
Ala Asp Leu Ala Glu Ser Ile Met Lys Asn Leu Arg Arg Val His Pro
            260                 265                 270
Ile Ser Thr Met Ile Lys Gly Leu Tyr Gly Ile Lys Glu Asp Val Phe
        275                 280                 285
Leu Ser Val Pro Cys Ile Leu Gly Gln Asn Gly Ile Ser Asp Val Val
    290                 295                 300
Lys Val Thr Leu Thr Pro Glu Glu Gln Ala Cys Leu Lys Lys Ser Ala
305                 310                 315                 320
Asp Thr Leu Trp Gly Ile Gln Lys Glu Leu Gln Phe
                325                 330

<210> SEQ ID NO 9
<211> LENGTH: 332
<212> TYPE: PRT
<213> ORGANISM: Rattus norvegicus LDH protein

<400> SEQUENCE: 9

Met Ala Ala Leu Lys Asp Gln Leu Ile Val Asn Leu Leu Lys Glu Glu
1               5                   10                  15
Gln Val Pro Gln Asn Lys Ile Thr Val Val Gly Val Gly Ala Val Gly
                20                  25                  30
Met Ala Cys Ala Ile Ser Ile Leu Met Lys Asp Leu Ala Asp Glu Leu
            35                  40                  45
Ala Leu Val Asp Val Ile Glu Asp Lys Leu Lys Gly Glu Met Met Asp
        50                  55                  60
Leu Gln His Gly Ser Leu Phe Leu Lys Thr Pro Lys Ile Val Ser Ser
65                  70                  75                  80
Lys Asp Tyr Ser Val Thr Ala Asn Ser Lys Leu Val Ile Ile Thr Ala
                85                  90                  95
Gly Ala Arg Gln Gln Glu Gly Glu Ser Arg Leu Asn Leu Val Gln Arg
            100                 105                 110
Asn Val Asn Ile Phe Lys Phe Ile Ile Pro Asn Val Val Lys Tyr Ser
        115                 120                 125
Pro Gln Cys Lys Leu Leu Ile Val Ser Asn Pro Val Asp Ile Leu Thr
    130                 135                 140
Tyr Val Ala Trp Lys Ile Ser Gly Phe Pro Lys Asn Arg Val Ile Gly
145                 150                 155                 160
Ser Gly Cys Asn Leu Asp Ser Ala Arg Phe Arg Tyr Leu Met Gly Glu
```

|     |     | 165 |     |     |     | 170 |     |     |     | 175 |     |
| --- | --- | --- | --- | --- | --- | --- | --- | --- | --- | --- | --- |

Arg Leu Gly Val His Pro Leu Ser Cys His Gly Trp Val Leu Gly Glu
                180                 185                 190

His Gly Asp Ser Ser Val Pro Val Trp Ser Gly Val Asn Val Ala Gly
            195                 200                 205

Val Ser Leu Lys Ser Leu Asn Pro Gln Leu Gly Thr Asp Ala Asp Lys
        210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
        290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 10
<211> LENGTH: 1140
<212> TYPE: DNA
<213> ORGANISM: Ornithorhynchus anatinus

<400> SEQUENCE: 10

```
ttccaagatg gccggcgtca aggaacagct gatccagaat cttctcaaag aggagtacgc      60
ccctcaaaat aagatcaccg tggttggagt tggtgctgtg ggcatggcct gtgccatcag     120
catcttgatg aaggatttgg ctgatgagct cgcccttgtt gatgtcattg aggataagct     180
gaagggagaa atgatggatc ttcagcatgg cagccttttc ctcaggactc caaagatcgt     240
ctctggcaaa gactacagcg tgactgccaa ctccaagctg gttatcatca ccgccggggc     300
ccgtcagcag gagggagaga ccgtctgaa tctggtccag cgcaatgtca acatctttaa     360
attcatcatt cccaacgttg tcaagtacag ccccaactgc aagctgcttg tggtgtccaa     420
tccagtggat attttgacct acgtggcctg gaagatcagt ggcttcccca gaaccgagt     480
tatcggaagc ggctgcaatc tggattctgc ccgcttccgc tatctgatgg agagaggct     540
gggcatccac tccacaagct gtcacggctg ggtcatcgga gaacacggag actctagtgt     600
tcccgtgtgg agcggggtga acgttgccgg tgtctctctg aagaacctgc accccgattt     660
gggaactgat gcagacaagg agcagtggaa ggatgttcat aagcaggtgg ttgacagtgc     720
ctacgaggtc atcaaactga agggctacac ctcctgggcc atcggcctct cggtagccga     780
tctggcagaa agcatcgtga gaatcttag gcgggtgcac cccatttcca ccatgattaa     840
gggcctgtac gggatcaaag atgaagtctt cctcagcgtc cctgtgtctg gggccagaa     900
cggcatctcg gacgtggtga agataaccct gaagtccgag gaggaggctc atctgaagaa     960
gagcgcagac accctgtggg gaattcagaa ggaactgcag ttttaaggct tttcaacatc    1020
ctagctgtct actgggtaac ggtagttagg ggattgggta tcccccactt ttgaagtagg    1080
ttagctgtct actgggtaac ggtagttagg ggattgggta tcccccactt ttgaagtagg    1140
```

<210> SEQ ID NO 11
<211> LENGTH: 1527
<212> TYPE: DNA
<213> ORGANISM: Tursiops truncatus

<400> SEQUENCE: 11

| | | | | | |
|---|---|---|---|---|---|
| acgtgtactc | ccgattcctt | tcggttctaa | gtccaatatg | gcaactgtca | aggatcagct | 60 |
| gattcagaat | cttcttaagg | aagaacatgt | cccccagaat | aagattacag | tggttggtgt | 120 |
| tggtgctgtt | ggcatggcct | gtgccatcag | tatcttaatg | aaggacttgg | cagatgaact | 180 |
| tgctcttgtt | gatgtcatag | aagacaaact | gaagggagag | atgatggatc | tccaacatgg | 240 |
| cagccttttc | cttagaacac | caaaaatcgt | ctctggcaaa | gactatagtg | tgacagcaaa | 300 |
| ctccaagctg | gttattatca | cagctggggc | acgtcagcaa | gagggagaaa | gccgtcttaa | 360 |
| tttggtccaa | cgtaatgtga | acatctttaa | attcatcgtt | cctaatattg | taaaatacag | 420 |
| cccacactgc | aagttgcttg | ttgtttccaa | tccagtggat | atcttgacct | atgtggcttg | 480 |
| gaagataagc | ggctttccca | aaaccgtgt | tattggaagt | ggttgcaatt | tggattcagc | 540 |
| ccggttccgt | tacctcatgg | gggaaaggct | gggagttcac | ccattaagct | gtcatggatg | 600 |
| gatccttggg | gagcatggag | actctagtgt | gcctgtatgg | agtggagtga | atgttgctgg | 660 |
| tgtctccctg | aagaatctgc | accccgaatt | aggcactgat | gccgataagg | aacattggaa | 720 |
| agcaattcac | aaacaggtgg | ttgacagtgc | ttatgaggtg | atcaaactga | aaggctacac | 780 |
| atcctgggcc | gttggactat | ctgtggcaga | tttggcagaa | agtataatga | agaatcttag | 840 |
| gcgggtgcat | ccgatttcca | ccatgattaa | gggtttgtat | ggaataaaag | aggatgtctt | 900 |
| ccttagtgtt | ccttgcatct | tgggacagaa | tggaatctca | gatgttgtga | aagtgactct | 960 |
| gactcctgag | gaacaggcct | gtttgaagaa | gagtgcagat | acactttggg | ggatccagaa | 1020 |
| agagctgcag | ttttaaagtc | taatatcata | ccacttcact | gtctaggcta | caataggatt | 1080 |
| ttagttggag | gttgtgcata | ttgtccttta | tatctgatct | gtgactaaag | cagtaatgtt | 1140 |
| aagacagcct | aggaaaaaca | tcaatttcct | aacattagca | ataggaatgg | ttcataaaac | 1200 |
| cctgcagctg | tatcctgatg | ctgcatggca | cttatcttgt | gttgtcctaa | attggttcgt | 1260 |
| gtaaaatagt | tctacttcct | caagaggtac | cactgacagt | gttgcagatg | ctgcagttgc | 1320 |
| ccttcaaacc | agatgtgtat | ttaactctgt | gttatataac | ttctggttcc | tttagccaag | 1380 |
| atgcctagtc | caacttttttt | ctctccaatt | aatcacattc | tgggattgat | tataaatcca | 1440 |
| gtattgcatg | tcttgtgcat | aactgttcta | aagaatctta | ttttatgtac | tatatgtatc | 1500 |
| agaatagtat | acattgccat | gtaatgt | | | | 1527 |

<210> SEQ ID NO 12
<211> LENGTH: 1609
<212> TYPE: DNA
<213> ORGANISM: Rattus norvegicus

<400> SEQUENCE: 12

| | | | | | |
|---|---|---|---|---|---|
| gtgtgctgga | gccactgtcg | ccgatctcgc | gcacgctact | gctgctgctc | gcccgtcgtc | 60 |
| ccccatcgtg | cactaagcgg | tcccaaaaga | ttcaaagtcc | aagatggcag | ccctcaagga | 120 |
| ccagctgatt | gtgaatcttc | ttaaggaaga | acaggtcccc | cagaacaaga | ttacagttgt | 180 |
| tggggttggt | gctgttggca | tggcttgtgc | catcagtatc | ttaatgaagg | acttggctga | 240 |
| tgagcttgcc | cttgttgatg | tcatagaaga | taagctaaag | ggagagatga | tggatcttca | 300 |
| gcatggcagc | cttttcctta | agacaccaaa | aattgtctcc | agcaaagatt | atagtgtgac | 360 |

```
tgcaaactcc aagctggtca ttatcaccgc gggggcccgt cagcaagagg gagagagccg    420
gctcaatttg gtccagcgaa acgtgaacat cttcaagttc atcattccaa atgttgtgaa    480
atacagtcca cagtgcaaac tgctcatcgt ctcaaaccca gtggatatct tgacctacgt    540
ggcttggaag atcagcggct tccccaaaaa cagagttatt ggaagtggtt gcaatctgga    600
ttcggctcgg ttccgttacc tgatgggaga aaggctggga gttcatccac tgagctgtca    660
cgggtgggtc ctgggagagc atggcgactc cagtgtgcct gtgtggagtg gtgtgaacgt    720
cgccggcgtc tccctgaagt ctctgaaccc gcagctgggc acggatgcag acaaggagca    780
gtggaaggat gtgcacaagc aggtggttga cagtgcatac gaagtgatca agctgaaagg    840
ttacacatcc tgggccattg gcctctccgt ggcagacttg gccgagagca taatgaagaa    900
ccttaggcgg gtgcatccca tttccaccat gattaagggt ctctatggaa tcaaggagga    960
tgtcttcctc agcgtcccat gtatcctggg acaaaatgga atctcagatg ttgtgaaggt   1020
gacactgact cctgacgagg aggcccgcct gaagaagagt gcagataccc tctgggaat    1080 ccagaaggag ctgcagttct aaagtcttcc cagtgtccta gcacttcact gtccaggctg   1140
cagcagggtt tctatggaga ccacgcactt ctcatctgag ctgtggttag tccagttggt   1200
ccagttgtgt tgaggtggtc tgggggaaat ctcagttcca cagctctacc ctgctaagtg   1260
gtacttgtgt agtggtaacc tggttagtgt gacaatccca ctgtctccaa gacacactgc   1320
caactgcatg caggctttga ttaccctgtg agcctgctgc attgctgtgc tacgcaccct   1380
caccaaacat gcctaggcca tgagttccca gttagttata agctggctcc agtgtgtaag   1440
tccatcgtgt atatccttgtg cataaatgtt ctacaggata tttctgtat tatatgtgtc    1500 tgtagtgtac attgcaatat tacgtgaaat gtaagatctg catatggatg atggaaccaa   1560
ccactcaagt gtcatgccaa ggaaaacacc aaataaacct tgaacagtg               1609
```

<210> SEQ ID NO 13
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 13

```
ttcgcggcca cctacgccgc tatctttgca acaactatct gcgataactc agcaaatttt     60
gcatattcgt gttgcagtat tgcgataatg ggagtcttac ttccaacata acggcagaaa    120
gaaatgtgag aaaattttgc atcctttgcc tccgttcaag tatataaagt cggcatgctt    180
gataatcttt ctttccatcc tacattgttc taattattct tattctcctt tattctttcc    240
taacatacca agaaattaat cttctgtcat tcgcttaaac actatatcaa ta            292
```

<210> SEQ ID NO 14
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 14

```
atttggcgag cgttggttgg tggatcaagc ccacgcgtag gcaatcctcg agcagatccg     60
ccaggcgtgt atatatagcg tggatggcca ggcaacttta gtgctgacac atacaggcat    120
atatatatgt gtgcgacgac acatgatcat atggcatgca tgtgctctgt atgtatataa    180
aactcttgtt ttcttctttt ctctaaatat tctttcctta tacattagga cctttgcagc    240
```

```
ataaattact atacttctat agacacgcaa acacaaatac acacactaa         289
```

<210> SEQ ID NO 15
<211> LENGTH: 401
<212> TYPE: DNA
<213> ORGANISM: Artificial Sequence
<220> FEATURE:
<223> OTHER INFORMATION: Synthetic TEF1 promoter

<400> SEQUENCE: 15

```
atagcttcaa aatgtttcta ctcctttttt actcttccag attttctcgg actccgcgca    60
tcgccgtacc acttcaaaac acccaagcac agcatactaa atttcccctc tttcttcctc   120
tagggtgtcg ttaattaccc gtactaaagg tttggaaaag aaaaaagaga ccgcctcgtt   180
tcttttcctt cgtcgaaaaa ggcaataaaa attttttatca cgtttctttt tcttgaaaat   240
ttttttttg attttttttct ctttcgatga cctcccattg atatttaagt taataaacgg   300
tcttcaattt ctcaagtttc agtttcattt ttcttgttct attacaactt tttttacttc   360
ttgctcatta gaaagaaagc atagcaatct aatctaagtt t                       401
```

<210> SEQ ID NO 16
<211> LENGTH: 798
<212> TYPE: DNA
<213> ORGANISM: Artificial Sequence
<220> FEATURE:
<223> OTHER INFORMATION: Synthetic PGK1 promoter

<400> SEQUENCE: 16

```
ctttcctctt tttattaacc ttaatttttta ttttagattc ctgacttcaa ctcaagacgc    60
acagatatta taacatctgc ataataggca tttgcaagaa ttactcgtga gtaaggaaag   120
agtgaggaac tatcgcatac ctgcatttaa agatgccgat ttgggcgcga atcctttatt   180
ttggcttcac cctcatacta ttatcagggc cagaaaaagg aagtgtttcc ctccttcttg   240
aattgatgtt accctcataa agcacgtggc ctcttatcga gaaagaaatt accgtcgctc   300
gtgatttgtt tgcaaaaaga acaaaactga aaaaacccag acacgctcga cttcctgtct   360
tcctattgat tgcagcttcc aatttcgtca cacaacaagg tcctagcgac ggctcacagg   420
ttttgtaaca agcaatcgaa ggttctggaa tggcgggaaa gggtttagta ccacatgcta   480
tgatgcccac tgtgatctcc agagcaaagt tcgttcgatc gtactgttac tctctctctt   540
tcaaacagaa ttgtccgaat cgtgtgacaa caacagcctg ttctcacaca ctcttttctt   600
ctaaccaagg gggtggttta gtttagtaga acctcgtgaa acttacattt acatatatat   660
aaacttgcat aaattggtca atgcaagaaa tacatatttg gtcttttcta attcgtagtt   720
tttcaagttc ttagatgctt tctttttctc ttttttacag atcatcaagg aagtaattat   780
ctactttta caacaaat                                                  798
```

<210> SEQ ID NO 17
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 17

```
agtttatcat tatcaatact cgccatttca aagaatacgt aaataattaa tagtagtgat    60
tttcctaact ttatttagtc aaaaaattag ccttttaatt ctgctgtaac ccgtacatgc   120
```

```
ccaaaatagg gggcgggtta cacagaatat ataacatcgt aggtgtctgg gtgaacagtt      180
tattcctggc atccactaaa tataatggag cccgcttttt aagctggcat ccagaaaaaa      240
aaagaatccc agcaccaaaa tattgttttc ttcaccaacc atcagttcat aggtccattc      300
tcttagcgca actacagaga acaggggcac aaacaggcaa aaacgggca caacctcaat       360 ggagtgatgc aacctgcctg gagtaaatga tgacacaagg caattgaccc acgcatgtat      420
ctatctcatt tcttacacc ttctattacc ttctgctctc tctgatttgg aaaaagctga       480 aaaaaaggt tgaaaccagt tccctgaaat tattcccta cttgactaat aagtatataa        540
agacggtagg tattgattgt aattctgtaa atctatttct taaacttctt aaattctact     600
tttatagtta gtcttttttt tagttttaaa acaccagaac ttagtttcga cggat           655

<210> SEQ ID NO 18
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 18
gccgggatcg aagaaatgat ggtaaatgaa ataggaaatc aaggagcatg aaggcaaaag       60
acaaatataa gggtcgaacg aaaaataaag tgaaagtgt tgatatgatg tatttggctt      120
tgcggcgccg aaaaacgag tttacgcaat tgcacaatca tgctgactct gtggcggacc       180
cgcgctcttg ccggcccggc gataacgctg ggcgtgaggc tgtgcccggc ggagtttttt      240
gcgcctgcat tttccaaggt ttaccctgcg ctaaggggcg agattggaga agcaataaga     300
atgccggttg gggttgcgat gatgacgacc acgacaactg gtgtcattat ttaagttgcc     360
gaaagaacct gagtgcattt gcaacatgag tatactagaa gaatgagcca agacttgcga     420
gacgcgagtt tgccggtggt gcgaacaata gagcgaccat gaccttgaag gtgagacgcg     480
cataaccgct agagtacttt gaagaggaaa cagcaatagg gttgctacca gtataaatag    540
acaggtacat acaacactgg aaatggttgt ctgtttgagt acgctttcaa ttcatttggg    600
tgtgcacttt attatgttac aatatggaag ggaactttac acttctccta tgcacatata    660
ttaattaaag tccaatgcta gtagagaagg ggggtaacac ccctccgcgc tcttttccga    720
tttttttcta aaccgtggaa tatttcggat atccttttgt tgtttccggg tgtacaatat    780
ggacttcctc ttttctggca accaaaccca tacatcggga ttcctataat accttcgttg    840
gtctccctaa catgtaggtg gcggagggga gatatacaat agaacagata ccagacaaga    900
cataatgggc taaacaagac tacaccaatt acactgcctc attgatggtg gtacataacg    960
aactaatact gtagccctag acttgatagc catcatcata tcgaagtttc actacccttt   1020
ttccatttgc catctattga agtaataata ggcgcatgca acttcttttc ttttttttc    1080 ttttctctct ccccgttgt tgtctcacca tatccgcaat gacaaaaaaa tgatggaaga    1140
cactaaagga aaaattaac gacaaagaca gcaccaacag atgtcgttgt tccagagctg    1200
atgaggggta tctcgaagca cacgaaactt tttccttcct tcattcacgc acactactct   1260
ctaatgagca acgtatacg gccttccttc cagttacttg aatttgaaat aaaaaaaagt    1320
ttgctgtctt gctatcaagt ataaatagac ctgcaattat taatcttttg tttcctcgtc   1380
attgttctcg ttcccttct tccttgtttc ttttctgca caatatttca agctatacca     1440
agcatacaat caactccaag ctggccgc                                       1468
```

```
<210> SEQ ID NO 19
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 19
tcatgtaatt agttatgtca cgcttacatt cacgccctcc ccccacatcc gctctaaccg      60
aaaaggaagg agttagacaa cctgaagtct aggtccctat ttattttttt atagttatgt     120
tagtattaag aacgttattt atatttcaaa ttttcttttt ttttctgtac agacgcgtgt     180
acgcatgtaa cattatactg aaaaccttgc ttgagaaggt tttgggacgc tcgaaggctt     240
taatttgcgg cc                                                         252

<210> SEQ ID NO 20
<211> LENGTH: 1047
<212> TYPE: DNA
<213> ORGANISM: Saccharomyces cerevisiae

<400> SEQUENCE: 20
atgtctatcc cagaaactca aaaggtgtt atcttctacg aatcccacgg taagttggaa       60
tacaaagata ttccagttcc aaagccaaag gccaacgaat tgttgatcaa cgttaaatac     120
tctggtgtct gtcacactga cttgcacgct tggcacggtg actggccatt gccagttaag     180
ctaccattag ttggtggtca cgaaggtgcc ggtgtcgttg tcggcatggg tgaaaacgtt     240
aagggctgga gatcggtga ctacgccggt atcaaatggt tgaacggttc ttgtatggcc      300
tgtgaatact gtgaattggg taacgaatcc aactgtcctc acgctgactt gtctggttac     360
acccacgacg gttctttcca agaatacgct accgctgacg ctgttcaagc cgctcacatt     420
cctcaaggta ctgacttggc tgaagtcgcc ccagttttgt gtgctggtat caccgtctac     480
aaggctttga gtctgctaa cttgatggcc ggtcactggg ttgctatctc cggtgctgct     540
ggtggtctag gttcttggc tgttcaatac gccaaggcta tgggttacag agtcttgggt     600
attgacggtg gtgaaggtaa ggaagaatta ttcagatcca tcggtggtga agtcttcatt     660
gacttcacta aggaaaagga cattgtcggt gctgttctaa aggccactga cggtggtgct     720
cacggtgtca tcaacgtttc cgtttccgaa gccgctattg aagcttccac cagatacgtt     780
agagctaacg gtaccaccgt tttggtcggt atgccagctg gtgccaagtg ttgttctgat     840
gtcttcaacc aagtcgtcaa gtccatctct attgttggtt cttacgtcgg taacagagct     900
gacaccagag aagctttgga cttcttcgcc agaggttga tcaagtctcc aatcaaggtt      960
gtcggcttgt ctaccttgcc agaaatttac gaaaagatgg aaagggtca atcgttggt     1020 agatacgttg ttgacacttc taaataa                                        1047

<210> SEQ ID NO 21
<211> LENGTH: 348
<212> TYPE: PRT
<213> ORGANISM: Saccharomyces cerevisiae

<400> SEQUENCE: 21

Met Ser Ile Pro Glu Thr Gln Lys Gly Val Ile Phe Tyr Glu Ser His
  1               5                  10                  15

Gly Lys Leu Glu Tyr Lys Asp Ile Pro Val Pro Lys Pro Lys Ala Asn
             20                  25                  30

Glu Leu Leu Ile Asn Val Lys Tyr Ser Gly Val Cys His Thr Asp Leu
         35                  40                  45
```

```
His Ala Trp His Gly Asp Trp Pro Leu Pro Val Lys Leu Pro Leu Val
         50                  55                  60

Gly Gly His Glu Gly Ala Gly Val Val Gly Met Gly Glu Asn Val
 65                  70                  75                  80

Lys Gly Trp Lys Ile Gly Asp Tyr Ala Gly Ile Lys Trp Leu Asn Gly
                 85                  90                  95

Ser Cys Met Ala Cys Glu Tyr Cys Glu Leu Gly Asn Glu Ser Asn Cys
             100                 105                 110

Pro His Ala Asp Leu Ser Gly Tyr Thr His Asp Gly Ser Phe Gln Gln
             115                 120                 125

Tyr Ala Thr Ala Asp Ala Val Gln Ala Ala His Ile Pro Gln Gly Thr
             130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                 165                 170                 175

Ser Gly Ala Ala Gly Gly Leu Gly Ser Leu Ala Val Gln Tyr Ala Lys
             180                 185                 190

Ala Met Gly Tyr Arg Val Leu Gly Ile Asp Gly Gly Glu Gly Lys Glu
             195                 200                 205

Glu Leu Phe Arg Ser Ile Gly Gly Glu Val Phe Ile Asp Phe Thr Lys
             210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                 245                 250                 255

Thr Arg Tyr Val Arg Ala Asn Gly Thr Thr Val Leu Val Gly Met Pro
             260                 265                 270

Ala Gly Ala Lys Cys Cys Ser Asp Val Phe Asn Gln Val Val Lys Ser
             275                 280                 285

Ile Ser Ile Val Gly Ser Tyr Val Gly Asn Arg Ala Asp Thr Arg Glu
             290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                 325                 330                 335

Gln Ile Val Gly Arg Tyr Val Val Asp Thr Ser Lys
             340                 345

<210> SEQ ID NO 22
<211> LENGTH: 563
<212> TYPE: PRT
<213> ORGANISM: Saccharomyces cerevisiae

<400> SEQUENCE: 22

Met Ser Glu Ile Thr Leu Gly Lys Tyr Leu Phe Glu Arg Leu Lys Gln
 1               5                  10                  15

Val Asn Val Asn Thr Val Phe Gly Leu Pro Gly Asp Phe Asn Leu Ser
                 20                  25                  30

Leu Leu Asp Lys Ile Tyr Glu Val Glu Gly Met Arg Trp Ala Gly Asn
             35                  40                  45

Ala Asn Glu Leu Asn Ala Ala Tyr Ala Ala Asp Gly Tyr Ala Arg Ile
         50                  55                  60

Lys Gly Met Ser Cys Ile Ile Thr Thr Phe Gly Val Gly Glu Leu Ser
```

```
            65                  70                  75                  80
Ala Leu Asn Gly Ile Ala Gly Ser Tyr Ala Glu His Val Gly Val Leu
                85                  90                  95

His Val Gly Val Pro Ser Ile Ser Ala Gln Ala Lys Gln Leu Leu
               100                 105                 110

Leu His His Thr Leu Gly Asn Gly Asp Phe Thr Val Phe His Arg Met
               115                 120                 125

Ser Ala Asn Ile Ser Glu Thr Thr Ala Met Ile Thr Asp Ile Ala Thr
130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
               180                 185                 190

Asp Ala Glu Ser Glu Lys Glu Val Ile Asp Thr Ile Leu Ala Leu Val
               195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
                260                 265                 270

Lys Glu Ala Val Glu Ser Ala Asp Leu Ile Leu Ser Val Gly Ala Leu
                275                 280                 285

Leu Ser Asp Phe Asn Thr Gly Ser Phe Ser Tyr Ser Tyr Lys Thr Lys
                290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
                355                 360                 365

Trp Met Trp Asn Gln Leu Gly Asn Phe Leu Gln Glu Gly Asp Val Val
                370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
                450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495
```

Ser Leu Leu Pro Thr Phe Gly Ala Lys Asp Tyr Glu Thr His Arg Val
              500                 505                 510

Ala Thr Thr Gly Glu Trp Asp Lys Leu Thr Gln Asp Lys Ser Phe Asn
              515                 520                 525

Asp Asn Ser Lys Ile Arg Met Ile Glu Ile Met Leu Pro Val Phe Asp
              530                 535                 540

Ala Pro Gln Asn Leu Val Glu Gln Ala Lys Leu Thr Ala Ala Thr Asn
545                 550                 555                 560

Ala Lys Gln

<210> SEQ ID NO 23
<211> LENGTH: 1692
<212> TYPE: DNA
<213> ORGANISM: Saccharomyces cerevisiae

<400> SEQUENCE: 23

```
atgtctgaaa ttactttggg taaatatttg ttcgaaagat taaagcaagt caacgttaac    60
accgttttcg gtttgccagg tgacttcaac ttgtccttgt tggacaagat ctacgaagtt   120
gaaggtatga gatgggctgg taacgccaac gaattgaacg ctgcttacgc cgctgatggt   180
tacgctcgta tcaagggtat gtcttgtatc atcaccacct tcggtgtcgg tgaattgtct   240
gctttgaacg gtattgccgg ttcttacgct gaacacgtcg gtgttttgca cgttgttggt   300
gtcccatcca tctctgctca agctaagcaa ttgttgttgc accacacctt gggtaacggt   360
gacttcactg ttttccacag aatgtctgcc aacatttctg aaaccactgc tatgatcact   420
gacattgcta ccgccccagc tgaaattgac agatgtatca gaaccactta cgtcacccaa   480
agaccagtct acttaggttt gccagctaac ttggtcgact gaacgtccc agctaagttg    540
ttgcaaactc caattgacat gtctttgaag ccaaacgatg ctgaatccga aaggaagtc    600
attgacacca tcttggcttt ggtcaaggat gctaagaacc cagttatctt ggctgatgct   660
tgttgttcca gacacgacgt caaggctgaa actaagaagt tgattgactt gactcaattc   720
ccagcttttcg tcaccccaat gggtaagggt tccattgacg aacaacaccc aagatacggt   780
ggtgtttacg tcggtaccct tgtccaagcca gaagttaagg aagccgttga atctgctgac   840
ttgattttgt ctgtcggtgc tttgttgtct gatttcaaca ccggttcttt ctcttactct   900
tacaagacca gaacattgt cgaattccac tccgaccaca tgaagatcag aaacgccact   960
ttcccaggtg tccaaatgaa attcgttttg caaaagttgt tgaccactat tgctgacgcc  1020
gctaagggtt acaagccagt tgctgtccca gctagaactc cagctaacgc tgctgtccca  1080
gcttctaccc cattgaagca agaatggatg tggaaccaat tgggtaactt cttgcaagaa  1140
ggtgatgttg tcattgctga aaccggtacc tccgctttcg gtatcaacca aaccactttc  1200
ccaaacaaca cctacggtat ctctcaagtc ttatggggtt ccattggttt caccactggt  1260
gctaccttgg gtgctgcttt cgctgctgaa gaaattgatc aaagaagag agttatctta  1320
ttcattggtg acggttcttt gcaattgact gttcaagaaa tctccaccat gatcagatgg  1380
ggcttgaagc catacttgtt cgtcttgaac aacgatggtt acaccattga aaagttgatt  1440
cacggtccaa aggctcaata caacgaaatt caaggtgggg accacctatc cttgttgcca  1500
actttcggtg ctaaggacta tgaaacccac agagtcgcta ccaccggtga atgggacaag  1560
ttgacccaag acaagtctt caacgacaac tctaagatca gaatgattga atcatgttg   1620
ccagtcttcg atgctccaca aaacttggtt gaacaagcta agttgactgc tgctaccaac  1680
```
gctaagcaat aa                                                      1692

<210> SEQ ID NO 24
<211> LENGTH: 591
<212> TYPE: PRT
<213> ORGANISM: Saccharomyces cerevisiae

<400> SEQUENCE: 24

Met Leu Lys Tyr Lys Pro Leu Leu Lys Ile Ser Lys Asn Cys Glu Ala
1               5                   10                  15

Ala Ile Leu Arg Ala Ser Lys Thr Arg Leu Asn Thr Ile Arg Ala Tyr
            20                  25                  30

Gly Ser Thr Val Pro Lys Ser Lys Ser Phe Glu Gln Asp Ser Arg Lys
        35                  40                  45

Arg Thr Gln Ser Trp Thr Ala Leu Arg Val Gly Ala Ile Leu Ala Ala
    50                  55                  60

Thr Ser Ser Val Ala Tyr Leu Asn Trp His Asn Gly Gln Ile Asp Asn
65                  70                  75                  80

Glu Pro Lys Leu Asp Met Asn Lys Gln Lys Ile Ser Pro Ala Glu Val
                85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
            405                 410                 415

Glu Leu Lys Lys Lys Thr Lys Leu Pro Ile Val Ile Lys Gly Val Gln
        420                 425                 430

Arg Thr Glu Asp Val Ile Lys Ala Glu Ile Gly Val Ser Gly Val
        435                 440                 445

Val Leu Ser Asn His Gly Gly Arg Gln Leu Asp Phe Ser Arg Ala Pro
450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
            485                 490                 495

Asp Val Leu Lys Ala Leu Cys Leu Gly Ala Lys Gly Val Gly Leu Gly
        500                 505                 510

Arg Pro Phe Leu Tyr Ala Asn Ser Cys Tyr Gly Arg Asn Gly Val Glu
        515                 520                 525

Lys Ala Ile Glu Ile Leu Arg Asp Glu Ile Glu Met Ser Met Arg Leu
530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
            565                 570                 575

Asn Glu Val Tyr Glu Gly Pro Thr Leu Thr Glu Phe Glu Asp Ala
        580                 585                 590

<210> SEQ ID NO 25
<211> LENGTH: 1776
<212> TYPE: DNA
<213> ORGANISM: Saccharomyces cerevisiae

<400> SEQUENCE: 25
atgctaaaat acaaaccttt actaaaaatc tcgaagaact gtgaggctgc tatcctcaga    60
gcgtctaaga ctagattgaa cacaatccgc gcgtacggtt ctaccgttcc aaaatccaag   120
tcgttcgaac aagactcaag aaaacgcaca cagtcatgga ctgccttgag agtcggtgca   180
attctagccg ctactagttc cgtggcgtat ctaaactggc ataatggcca atagacaac    240 gagccgaaac tggatatgaa taaacaaaag atttcgcccg ctgaagttgc caagcataac   300
aagcccgatg attgttgggt gtgatcaat ggttacgtat acgacttaac gcgattccta    360
ccaaatcatc caggtgggca ggatgttatc aagtttaacg ccgggaaaga tgtcactgct   420 attttttgaac cactacatgc tcctaatgtc atcgataagt atatagctcc cgagaaaaaa   480
ttgggtcccc ttcaaggatc catgcctcct gaacttgtct gtcctcctta tgctcctggt   540
gaaactaagg aagatatcgc tagaaaagaa caactaaaat cgctgctacc tcctctagat   600
aatattatta acctttacga ctttgaatac ttggcctctc aaactttgac taaacaagcg   660
tgggcctact attcctccgg tgctaacgac gaagttactc acagagaaaa ccataatgct   720
tatcatagga ttttttttcaa accaaagatc cttgtagatg tacgcaaagt agacatttca   780
actgacatgt tgggttctca tgtggatgtt cccttctacg tgtctgctac agctttgtgt   840
aaactgggaa accccttaga aggtgaaaaa gatgtcgcca gaggttgtgg ccaaggtgtg   900

```
acaaaagtcc cacaaatgat atctactttg gcttcatgtt ccectgagga aattattgaa    960
gcagcaccct ctgataaaca aattcaatgg taccaactat atgttaactc tgatagaaag   1020
atcactgatg atttggttaa aaatgtagaa aagctgggtg taaaggcatt atttgtcact   1080
gtggatgctc caagtttagg tcaaagagaa aaagatatga agctgaaatt ttccaataca   1140
aaggctggtc caaaagcgat gaagaaaact aatgtagaag aatctcaagg tgcttcgaga   1200
gcgttatcaa agtttattga cccctctttg acttggaaag atatagaaga gttgaagaaa   1260
aagacaaaac tacctattgt tatcaaaggt gttcaacgta ccgaagatgt tatcaaagca   1320
gcagaaatcg gtgtaagtgg ggtggttcta tccaatcatg gtggtagaca attagatttt   1380
tcaagggctc ccattgaagt cctggctgaa accatgccaa tcctggaaca acgtaacttg   1440
aaggataagt tggaagtttt cgtggacggt ggtgttcgtc gtggtacaga tgtcttgaaa   1500
gcgttatgtc taggtgctaa aggtgttggt ttgggtagac cattcttgta tgcgaactca   1560
tgctatggtc gtaatggtgt tgaaaaagcc attgaaattt taagagatga aattgaaatg   1620
tctatgagac tattaggtgt tactagcatt gcggaattga agcctgatct tttagatcta   1680
tcaacactaa aggcaagaac agttggagta ccaaacgacg tgctgtataa tgaagtttat   1740
gagggaccta ctttaacaga atttgaggat gcatga                             1776
```

<210> SEQ ID NO 26
<211> LENGTH: 391
<212> TYPE: PRT
<213> ORGANISM: Saccharomyces cerevisiae

<400> SEQUENCE: 26

```
Met Ser Ala Ala Ala Asp Arg Leu Asn Leu Thr Ser Gly His Leu Asn
  1               5                  10                  15

Ala Gly Arg Lys Arg Ser Ser Ser Val Ser Leu Lys Ala Ala Glu
             20                  25                  30

Lys Pro Phe Lys Val Thr Val Ile Gly Ser Gly Asn Trp Gly Thr Thr
         35                  40                  45

Ile Ala Lys Val Val Ala Glu Asn Cys Lys Gly Tyr Pro Glu Val Phe
     50                  55                  60

Ala Pro Ile Val Gln Met Trp Val Phe Glu Glu Ile Asn Gly Glu
 65                  70                  75                  80

Lys Leu Thr Glu Ile Ile Asn Thr Arg His Gln Asn Val Lys Tyr Leu
                 85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
```

```
            210                 215                 220
Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
        290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
        370                 375                 380

Glu Leu Asp Leu His Glu Asp
385                 390

<210> SEQ ID NO 27
<211> LENGTH: 1176
<212> TYPE: DNA
<213> ORGANISM: Saccharomyces cerevisiae

<400> SEQUENCE: 27
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga atacttgcc tggcatcact      300 ctacccgaca atttggttgc taatccagac ttgattgatt cagtcaagga tgtcgacatc     360
atcgttttca acattccaca tcaattttg ccccgtatct gtagccaatt gaaaggtcat      420
gttgattcac acgtcagagc tatctcctgt ctaaaggggtt tgaagttgg tgctaaaggt     480 gtccaattgc tatcctctta catcactgag gaactaggta ttcaatgtgg tgctctatct     540
ggtgctaaca ttgccaccga agtcgctcaa gaacactggt ctgaacaac agttgcttac      600 cacattccaa aggatttcag aggcgagggc aaggacgtcg accataaggt tctaaaggcc     660
ttgttccaca gaccttactt ccacgttagt gtcatcgaag atgttgctgg tatctccatc     720
tgtggtgctt tgaagaacgt tgttgcctta ggttgtggtt tcgtcgaagg tctaggctgg     780
ggtaacaacg cttctgctgc catccaaaga gtcggttggg gtgagatcat cagattcggt     840
caaatgtttt tcccagaatc tagaagaa acatactacc aagagtctgc tggtgttgct      900
gatttgatca ccacctgcgc tggtggtaga aacgtcaagg ttgctaggct aatggctact     960
tctggtaagg acgcctggga atgtgaaaag gagttgttga atggccaatc cgctcaaggt    1020
ttaattacct gcaaagaagt tcacgaatgg ttggaaacat gtggctctgt cgaagacttc    1080
```

```
ccattatttg aagccgtata ccaaatcgtt tacaacaact acccaatgaa gaacctgccg    1140
gacatgattg aagaattaga tctacatgaa gattag                              1176
```

<210> SEQ ID NO 28
<211> LENGTH: 753
<212> TYPE: DNA
<213> ORGANISM: Saccharomyces cerevisiae

<400> SEQUENCE: 28

```
atgcctttga ccacaaaacc tttatctttg aaaatcaacg ccgctctatt cgatgttgac      60
ggtaccatca tcatctctca accagccatt gctgctttct ggagagattt cggtaaagac    120
aagccttact tcgatgccga acacgttatt cacatctctc acggttggag aacttacgat    180
gccattgcca agttcgctcc agactttgct gatgaagaat acgttaacaa gctagaaggt    240
gaaatcccag aaaagtacgg tgaacactcc atcgaagttc caggtgctgt caagttgtgt    300
aatgctttga cgccttgcc aaggaaaaa tgggctgtcg ccacctctgg tacccgtgac    360
atggccaaga atggttcga cattttgaag atcaagagac cagaatactt catcaccgcc    420
aatgatgtca agcaaggtaa gcctcaccca gaaccatact aaagggtag aaacggtttg    480 ggtttcccaa ttaatgaaca agaccccatcc aaatctaagg ttgttgtctt tgaagacgca    540
ccagctggta ttgctgctgg taaggctgct ggctgtaaaa tcgttggtat tgctaccact    600
ttcgatttgg acttcttgaa ggaaaagggt tgtgacatca ttgtcaagaa ccacgaatct    660
atcagagtcg gtgaatacaa cgctgaaacc gatgaagtcg aattgatctt tgatgactac    720
ttatacgcta aggatgactt gttgaaatgg taa                                  753
```

<210> SEQ ID NO 29
<211> LENGTH: 250
<212> TYPE: PRT
<213> ORGANISM: Saccharomyces cerevisiae

<400> SEQUENCE: 29

```
Met Pro Leu Thr Thr Lys Pro Leu Ser Leu Lys Ile Asn Ala Ala Leu
 1               5                  10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile His Ile Ser His Gly Trp Arg Thr Tyr Asp Ala Ile Ala Lys
    50                  55                  60

Phe Ala Pro Asp Phe Ala Asp Glu Glu Tyr Val Asn Lys Leu Glu Gly
65                  70                  75                  80

Glu Ile Pro Glu Lys Tyr Gly Glu His Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Lys Lys Trp Phe Asp Ile
        115                 120                 125

Leu Lys Ile Lys Arg Pro Glu Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Phe Pro Ile Asn Glu Gln Asp Pro Ser Lys Ser Lys Val Val Val
                165                 170                 175
```

```
Phe Glu Asp Ala Pro Ala Gly Ile Ala Ala Gly Lys Ala Ala Gly Cys
            180                 185                 190

Lys Ile Val Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Glu Tyr Asn Ala Glu Thr Asp Glu Val Glu Leu Ile Phe Asp Asp Tyr
225                 230                 235                 240

Leu Tyr Ala Lys Asp Asp Leu Leu Lys Trp
                245                 250

<210> SEQ ID NO 30
<211> LENGTH: 500
<212> TYPE: PRT
<213> ORGANISM: Saccharomyces cerevisiae

<400> SEQUENCE: 30

Met Thr Lys Leu His Phe Asp Thr Ala Glu Pro Val Lys Ile Thr Leu
  1               5                  10                  15

Pro Asn Gly Leu Thr Tyr Glu Gln Pro Thr Gly Leu Phe Ile Asn Asn
             20                  25                  30

Lys Phe Met Lys Ala Gln Asp Gly Lys Thr Tyr Pro Val Glu Asp Pro
         35                  40                  45

Ser Thr Glu Asn Thr Val Cys Glu Val Ser Ser Ala Thr Thr Glu Asp
     50                  55                  60

Val Glu Tyr Ala Ile Glu Cys Ala Asp Arg Ala Phe His Asp Thr Glu
 65                  70                  75                  80

Trp Ala Thr Gln Asp Pro Arg Glu Arg Gly Arg Leu Leu Ser Lys Leu
                 85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300
```

```
Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
            325                 330                 335

Gly Asn Pro Phe Asp Lys Ala Asn Phe Gln Gly Ala Ile Thr Asn Arg
        340                 345                 350

Gln Gln Phe Asp Thr Ile Met Asn Tyr Ile Asp Ile Gly Lys Lys Glu
    355                 360                 365

Gly Ala Lys Ile Leu Thr Gly Gly Glu Lys Val Gly Asp Lys Gly Tyr
370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
            405                 410                 415

Thr Leu Glu Glu Gly Val Glu Met Ala Asn Ser Ser Glu Phe Gly Leu
        420                 425                 430

Gly Ser Gly Ile Glu Thr Glu Ser Leu Ser Thr Gly Leu Lys Val Ala
    435                 440                 445

Lys Met Leu Lys Ala Gly Thr Val Trp Ile Asn Thr Tyr Asn Asp Phe
450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
            485                 490                 495

Arg Ile Lys Leu
        500

<210> SEQ ID NO 31
<211> LENGTH: 1503
<212> TYPE: DNA
<213> ORGANISM: Saccharomyces cerevisiae

<400> SEQUENCE: 31
atgactaagc tacactttga cactgctgaa ccagtcaaga tcacacttcc aaatggtttg      60
acatacgagc aaccaaccgg tctattcatt aacaacaagt ttatgaaagc tcaagacggt     120
aagacctatc ccgtcgaaga tccttccact gaaaacaccg tttgtgaggt ctcttctgcc     180
accactgaag atgttgaata tgctatcgaa tgtgccgacc gtgcttttcca cgacactgaa    240 tgggctaccc aagacccaag agaaagaggc cgtctactaa gtaagttggc tgacgaattg     300
gaaagccaaa ttgacttggt ttcttccatt gaagctttgg acaatggtaa aactttggcc     360
ttagcccgtg gggatgttac cattgcaatc aactgtctaa gagatgctgc tgcctatgcc     420
gacaaagtca acggtagaac aatcaacacc ggtgacggct acatgaactt caccacctta     480
gagccaatcg tgtctgtgg tcaaattatt ccatggaact ttccaataat gatgttggct     540
tggaagatcg ccccagcatt ggccatgggt aacgtctgta tcttgaaacc cgctgctgtc     600
acacctttaa atgccctata ctttgcttct ttatgtaaga aggttggtat tccagctggt     660
gtcgtcaaca tcgttccagg tcctggtaga actgttggtg ctgctttgac caacgaccca     720
agaatcagaa agctggcttt taccggttct acagaagtcg gtaagagtgt tgctgtcgac     780
tcttctgaat ctaacttgaa gaaaatcact ttggaactag tggtaagtc cgcccatttg     840 gtctttgacg atgctaacat taagaagact ttaccaaatc tagtaaacgg tattttcaag     900
aacgctggtc aaatttgttc ctctggttct agaatttacg ttcaagaagg tatttacgac     960
```

```
gaactattgg ctgctttcaa ggcttacttg gaaaccgaaa tcaaagttgg taatccattt    1020
gacaaggcta acttccaagg tgctatcact aaccgtcaac aattcgacac aattatgaac    1080
tacatcgata tcggtaagaa agaaggcgcc aagatcttaa ctggtggcga aaaagttggt    1140
gacaagggtt acttcatcag accaaccgtt ttctacgatg ttaatgaaga catgagaatt    1200
gttaaggaag aaattttggg accagttgtc actgtcgcaa agttcaagac tttagaagaa    1260
ggtgtcgaaa tggctaacag ctctgaattc ggtctaggtt ctggtatcga aacagaatct    1320
ttgagcacag gtttgaaggt ggccaagatg ttgaaggccg gtaccgtctg gatcaacaca    1380
tacaacgatt ttgactccag agttccattc ggtggtgtta agcaatctgg ttacggtaga    1440
gaaatgggtg aagaagtcta ccatgcatac actgaagtaa agctgtcag aattaagttg     1500 taa                                                                  1503

<210> SEQ ID NO 32
<211> LENGTH: 1404
<212> TYPE: DNA
<213> ORGANISM: Escherichia coli

<400> SEQUENCE: 32
atgaatcaac aggatattga acaggtggtg aaagcggtac tgctgaaaat gcaaagcagt      60
gacacgccgt ccgccgccgt tcatgagatg ggcgttttcg cgtccctgga tgacgccgtt     120
gcggcagcca agtcgcccta gcaagggtta aaaagcgtgg caatgcgcca gttagccatt     180
gctgccattc gtgaagcagg cgaaaaacac gccagagatt agcggaact tgccgtcagt      240 gaaaccggca tggggcgcgt tgaagataaa tttgcaaaaa acgtcgctca ggcgcgcggc     300
acaccaggcg ttgagtgcct ctctccgcaa gtgctgactg cgacaacgg cctgacccta      360 attgaaaacg caccctgggg cgtggtggct tcggtgacgc cttccactaa cccggcggca     420
accgtaatta caacgccat cagcctgatt gccgcgggca acagcgtcat ttttgccccg      480
catccggcgg cgaaaaaagt ctcccagcgg gcgattacgc tgctcaacca ggcgattgtt     540
gccgcaggtg ggccggaaaa cttactggtt actgtggcaa atccggatat cgaaaccgcg     600
caacgcttgt tcaagtttcc gggtatcggc ctgctggtgg taaccggcgg cgaagcggta     660
gtagaagcgg cgcgtaaaca caccaataaa cgtctgattg ccgcaggcgc tggcaacccg     720
ccggtagtgg tggatgaaac cgccgacctc gcccgtgccg ctcagtccat cgtcaaaggc     780
gcttctttcg ataacaacat catttgtgcc gacgaaaagg tactgattgt tgttgatagc    840
gtagccgatg aactgatgcg tctgatggaa ggccagcacg cggtgaaact gaccgcagaa    900
caggcgcagc agctgcaacc ggtgttgctg aaaaatatcg acgagcgcgg aaaaggcacc    960
gtcagccgtg actgggttgg tcgcgacgca ggcaaaatcg cggcggcaat cggccttaaa    1020
gttccgcaag aaacgcgcct gctgtttgtg gaaaccaccg cagaacatcc gtttgccgtg    1080
actgaactga tgatgccggt gttgcccgtc gtgcgcgtcg ccaacgtggc ggatgccatt    1140
gcgctagcgg tgaaactgga aggcggttgc caccacacgg cggcaatgca ctcgcgcaac    1200
atcgaaaaca tgaaccagat ggcgaatgct attgatacca gcattttcgt taagaacgga    1260
ccgtgcattg ccgggctggg gctgggcggg gaaggctgga ccaccatgac catcaccacg    1320
ccaaccggtg aagggtaac cagcgcgcgt acgtttgtcc gtctgcgtcg ctgtgtatta     1380
gtcgatgcgt ttcgcattgt ttaa                                           1404

<210> SEQ ID NO 33
```

<211> LENGTH: 467
<212> TYPE: PRT
<213> ORGANISM: Escherichia coli

<400> SEQUENCE: 33

```
Met Asn Gln Gln Asp Ile Glu Gln Val Val Lys Ala Val Leu Leu Lys
1               5                   10                  15

Met Gln Ser Ser Asp Thr Pro Ser Ala Ala Val His Glu Met Gly Val
            20                  25                  30

Phe Ala Ser Leu Asp Asp Ala Ala Ala Lys Val Ala Gln Gln
        35                  40                  45

Gly Leu Lys Ser Val Ala Met Arg Gln Leu Ala Ile Ala Ala Ile Arg
    50                  55                  60

Glu Ala Gly Glu Lys His Ala Arg Asp Leu Ala Glu Leu Ala Val Ser
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190

Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Val Glu Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
        275                 280                 285

Met Glu Gly Gln His Ala Val Lys Leu Thr Ala Glu Gln Ala Gln Gln
    290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Lys Val Pro Gln Glu Thr Arg Leu Leu Phe Val Glu Thr
            340                 345                 350

Thr Ala Glu His Pro Phe Ala Val Thr Glu Leu Met Met Pro Val Leu
        355                 360                 365

Pro Val Val Arg Val Ala Asn Val Ala Asp Ala Ile Ala Leu Ala Val
    370                 375                 380

Lys Leu Glu Gly Gly Cys His His Thr Ala Ala Met His Ser Arg Asn
```

```
                385                 390                 395                 400
Ile Glu Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
                420                 425                 430

Trp Thr Thr Met Thr Ile Thr Thr Pro Thr Gly Glu Gly Val Thr Ser
                435                 440                 445

Ala Arg Thr Phe Val Arg Leu Arg Arg Cys Val Leu Val Asp Ala Phe
450                 455                 460

Arg Ile Val
465

<210> SEQ ID NO 34
<211> LENGTH: 316
<212> TYPE: PRT
<213> ORGANISM: Escherichia coli

<400> SEQUENCE: 34

Met Ser Lys Arg Lys Val Ala Ile Ile Gly Ser Gly Asn Ile Gly Thr
1               5                   10                  15

Asp Leu Met Ile Lys Ile Leu Arg His Gly Gln His Leu Glu Met Ala
                20                  25                  30

Val Met Val Gly Ile Asp Pro Gln Ser Asp Gly Leu Ala Arg Ala Arg
            35                  40                  45

Arg Met Gly Val Ala Thr Thr His Glu Gly Val Ile Gly Leu Met Asn
        50                  55                  60

Met Pro Glu Phe Ala Asp Ile Asp Ile Val Phe Asp Ala Thr Ser Ala
65                  70                  75                  80

Gly Ala His Val Lys Asn Asp Ala Ala Leu Arg Glu Ala Lys Pro Asp
                85                  90                  95

Ile Arg Leu Ile Asp Leu Thr Pro Ala Ala Ile Gly Pro Tyr Cys Val
                100                 105                 110

Pro Val Val Asn Leu Glu Ala Asn Val Asp Gln Leu Asn Val Asn Met
            115                 120                 125

Val Thr Cys Gly Gly Gln Ala Thr Ile Pro Met Val Ala Ala Val Ser
        130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
                165                 170                 175

Thr Thr Ser Arg Ala Ile Glu Val Val Gly Gly Ala Ala Lys Gly Lys
            180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Asp Ile Glu Ala
210                 215                 220

Ser Ile Asn Glu Met Ala Glu Ala Val Gln Ala Tyr Val Pro Gly Tyr
225                 230                 235                 240

Arg Leu Lys Gln Arg Val Gln Phe Glu Val Ile Pro Gln Asp Lys Pro
                245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
        275                 280                 285
```

Asn Leu Asp Ile Met Thr Ser Ser Ala Leu Ala Thr Ala Glu Lys Met
    290                 295                 300

Ala Gln Ser Leu Ala Arg Lys Ala Gly Glu Ala Ala
305                 310                 315

<210> SEQ ID NO 35
<211> LENGTH: 951
<212> TYPE: DNA
<213> ORGANISM: Escherichia coli

<400> SEQUENCE: 35

| | | |
|---|---|---|
| atgagtaagc gtaaagtcgc cattatcggt tctggcaaca ttggtaccga tctgatgatt | 60 |
| aaaattttgc gtcacggtca gcatctggag atggcggtga tggttggcat tgatcctcag | 120 |
| tccgacggtc tggcgcgcgc cagacgtatg ggcgtcgcca ccacccatga agggtgatc | 180 |
| ggactgatga acatgcctga atttgctgat atcgacattg tatttgatgc gaccagcgcc | 240 |
| ggtgctcatg tgaaaaacga tgccgcttta cgcgaagcga accggatat tcgcttaatt | 300 |
| gacctgacgc ctgctgccat cggccttac tgcgtgccgg tggttaacct cgaggcgaac | 360 |
| gtcgatcaac tgaacgtcaa catggtcacc tgcggcggcc aggccaccat tccaatggtg | 420 |
| gcggcagttt cacgcgtggc gcgtgttcat tacgccgaaa ttatcgcttc tatcgccagt | 480 |
| aaatctgccg gacctggcac gcgtgccaat atcgatgaat ttacggaaac cacttcccga | 540 |
| gccattgaag tggtgggcgg cgcggcaaaa ggaaggcga ttattgtgct aacccagca | 600 |
| gagccaccgt tgatgatgcg tgacacggtg tatgtattga gcgacgaagc ttcacaagat | 660 |
| gatatcgaag cctcaatcaa tgaaatggct gaggcggtgc aggcttacgt accgggttat | 720 |
| cgcctgaaac agcgcgtgca gtttgaagtt atcccgcagg ataaaccggt caatttaccg | 780 |
| ggcgtggggc aattctccgg actgaaaaca gcggtctggc tggaagtcga aggcgcagcg | 840 |
| cattatctgc ctgcctatgc gggcaacctc gacattatga cttccagtgc gctggcgaca | 900 |
| gcggaaaaaa tggcccagtc actggcgcgc aaggcaggag aagcggcatg a | 951 |

<210> SEQ ID NO 36
<211> LENGTH: 954
<212> TYPE: DNA
<213> ORGANISM: Artificial Sequence
<220> FEATURE:
<223> OTHER INFORMATION: Synthetic S.cerevisiae codon optimized mhpF
    gene

<400> SEQUENCE: 36

| | | |
|---|---|---|
| atgtcaaagc gaaaagtagc tatcataggt tcaggtaata ttggtactga tttgatgatc | 60 |
| aaaatcctga catggcca gcacttggag atggccgtca tggttggtat cgacccacaa | 120 |
| tccgatggct agctagagc taggagaatg ggtgttgcca caactcacga agggttatt | 180 |
| ggcttaatga acatgccaga atttgcagac atcgatatag ttttgatgc tactagtgca | 240 |
| ggggcacatg tgaaaaacga cgcggcttta agaagccaa agccagatat tagattaatt | 300 |
| gatcttaccc ctgctgctat aggtccttac tgcgttcctg tagttaacct tgaagctaat | 360 |
| gtggaccagt tgaacgtgaa tatggttaca tgtggtggcc aagctaccat accaatggtt | 420 |
| gctgctgtct ctagagtggc cagagtacat tatgccgaga tcattgcgtc tatcgcatct | 480 |
| aagtctgccg gtcctggaac aagggctaac atcgatgagt tcactgagac aacctctaga | 540 |
| gctatcgaag tagtaggagg cgcagcaaaa ggtaaagcga tcattgtttt gaatcctgcc | 600 |
| gaaccaccat tgatgatgag agatacggtc tacgtgctat cagatgaagc ttcccaggat | 660 |

```
gacattgaag ctagcattaa tgagatggca gaagccgttc aagcatacgt gccaggatat    720
agactcaaac aaagagtcca atttgaggtc attccacaag acaagccagt taatctccca    780
ggggtcggtc aattctcagg actaaaaact gctgtttggt tagaagtaga aggagctgct    840
cattacctac cagcctacgc cggtaatttg gatataatga catcttccgc tcttgcaaca    900
gcagaaaaga tggcacaaag tctggcccgt aaggcaggag aagcggcata ataa          954
```

<210> SEQ ID NO 37
<211> LENGTH: 31
<212> TYPE: DNA
<213> ORGANISM: Artificial Sequence
<220> FEATURE:
<223> OTHER INFORMATION: primer
<400> SEQUENCE: 37

```
cgagctcttc gcggccacct acgccgctat c                                    31
```

<210> SEQ ID NO 38
<211> LENGTH: 32
<212> TYPE: DNA
<213> ORGANISM: Artificial Sequence
<220> FEATURE:
<223> OTHER INFORMATION: primer
<400> SEQUENCE: 38

```
gctctagata ttgatatagt gtttaagcga at                                   32
```

<210> SEQ ID NO 39
<211> LENGTH: 27
<212> TYPE: DNA
<213> ORGANISM: Artificial Sequence
<220> FEATURE:
<223> OTHER INFORMATION: primer
<400> SEQUENCE: 39

```
cggccatggc gggagctcgc atgcaag                                         27
```

<210> SEQ ID NO 40
<211> LENGTH: 28
<212> TYPE: DNA
<213> ORGANISM: Artificial Sequence
<220> FEATURE:
<223> OTHER INFORMATION: primer
<400> SEQUENCE: 40

```
cgggatatca ctagtgagct cgctccgc                                        28
```

<210> SEQ ID NO 41
<211> LENGTH: 2321
<212> TYPE: DNA
<213> ORGANISM: Artificial Sequence
<220> FEATURE:
<223> OTHER INFORMATION: Synthetic HPH cassette
<400> SEQUENCE: 41

```
gccgggagag ctcgcatgca agtaacctat tcaaagtaat atctcataca tgtttcatga    60
gggtaacaac atgcgactgg gtgagcatat gttccgctga tgtgatgtgc aagataaaca   120
agcaaggcag aaactaactt cttcttcatg taataaacac accccgcgtt tatttaccta   180
tctctaaact tcaacacctt atatcataac taatatttct tgagataagc acactgcacc   240
cataccttcc ttaaaacgt agcttccagt ttttggtggt tccggcttcc ttcccgattc    300
cgcccgctaa acgcatattt ttgttgcctg gtggcatttg caaaatgcat aacctatgca   360
```

```
tttaaaagat tatgtatgct cttctgactt ttcgtgtgat gaggctcgtg gaaaaaatga    420
ataatttatg aatttgagaa caattttgtg ttgttacggt attttactat ggaataatca    480
atcaattgag gattttatgc aaatatcgtt tgaatatttt tccgacccct tgagtacttt    540
tcttcataat tgcataatat tgtccgctgc ccctttttct gttagacggt gtcttgatct    600
acttgctatc gttcaacacc accttatttt ctaactattt tttttttagc tcatttgaat    660
cagcttatgg tgatggcaca ttttttgcata aacctagctg tcctcgttga acataggaaa    720
aaaaaatata taaacaaggc tctttcactc tccttgcaat cagatttggg tttgttccct    780
ttattttcat atttcttgtc atattccttt ctcaattatt attttctact cataacctca    840
cgcaaaataa cacagtcaaa tcctcgagat gaaaaagcct gaactcaccg cgacgtctgt    900
cgagaagttt ctgatcgaaa agttcgacag cgtctccgac ctgatgcagc tctcggaggg    960
cgaagaatct cgtgctttca gcttcgatgt aggagggcgt ggatatgtcc tgcgggtaaa   1020
tagctgcgcc gatggtttct acaaagatcg ttatgtttat cggcactttg catcggccgc   1080
gctcccgatt ccggaagtgc ttgacattgg ggaattcagc gagagcctga cctattgcat   1140
ctcccgccgt gcacagggtg tcacgttgca agacctgcct gaaaccgaac tgcccgctgt   1200
tctgcagccg gtcgcggagg ccatggatgc gatcgctgcg gccgatctta gccagacgag   1260
cgggttcggc ccattcggac cgcaaggaat cggtcaatac actacatggc gtgatttcat   1320
atgcgcgatt gctgatcccc atgtgtatca ctggcaaact gtgatggacg acaccgtcag   1380
tgcgtccgtc gcgcaggctc tcgatgagct gatgctttgg gccgaggact gccccgaagt   1440
ccggcacctc gtgcacgcgg atttcggctc caacaatgtc ctgacggaca atggccgcat   1500
aacagcggtc attgactgga gcgaggcgat gttcggggat cccaatacg aggtcgccaa    1560 catcttcttc tggaggccgt ggttggcttg tatggagcag cagacgcgct acttcgagcg   1620
gaggcatccg gagcttgcag gatcgccgcg gctccgggcg tatatgctcc gcattggtct   1680
tgaccaactc tatcagagct tggttgacgg caatttcgat gatgcagctt gggcgcaggg   1740
tcgatgcgac gcaatcgtcc gatccggagc cgggactgtc gggcgtacac aaatcgcccg   1800
cagaagcgcg gccgtctgga ccgatggctg tgtagaagta ctcgccgata gtggaaaccg   1860
acgccccagc actcgtccgg atcgggagat gggggaggct aactgaggat ccgtagatac   1920
attgatgcta tcaatcaaga gaactggaaa gattgtgtaa ccttgaaaaa cggtgaaact   1980
tacgggtcca agattgtcta cagatttttcc tgatttgcca gcttactatc cttcttgaaa   2040
atatgcactc tatatctttt agttcttaat tgcaacacat agatttgctg tataacgaat   2100
tttatgctat ttttaaaatt tggagttcag tgataaaagt gtcacagcga atttcctcac   2160
atgtagggac cgaattgttt acaagttctc tgtaccacca tggagacatc aaaaattgaa   2220
aatctatgga aagatatgga cggtagcaac aagaatatag cacgagccgc ggagcgagct   2280
cggccgcact agtgatatcc cgcggccatg gcggccggga g                        2321
```

<210> SEQ ID NO 42
<211> LENGTH: 75
<212> TYPE: DNA
<213> ORGANISM: Artificial Sequence
<220> FEATURE:
<223> OTHER INFORMATION: primer

<400> SEQUENCE: 42

```
acaatatttc aagctatacc aagcatacaa tcaactatct catatacaat gggccgcaaa    60
```

```
ttaaagcctt cgagc                                                          75

<210> SEQ ID NO 43
<211> LENGTH: 75
<212> TYPE: DNA
<213> ORGANISM: Artificial Sequence
<220> FEATURE:
<223> OTHER INFORMATION: primer

<400> SEQUENCE: 43
aatcataaga aattcgctta tttagaagtg tcaacaacgt atctaccaac gactaaaggg         60
aacaaaagct ggagc                                                          75

<210> SEQ ID NO 44
<211> LENGTH: 18
<212> TYPE: DNA
<213> ORGANISM: Artificial Sequence
<220> FEATURE:
<223> OTHER INFORMATION: primer

<400> SEQUENCE: 44
gaaacagcta tgaccatg                                                       18

<210> SEQ ID NO 45
<211> LENGTH: 32
<212> TYPE: DNA
<213> ORGANISM: Artificial Sequence
<220> FEATURE:
<223> OTHER INFORMATION: primer

<400> SEQUENCE: 45
gacatgacga gctcgaattg ggtaccggcc gc                                       32

<210> SEQ ID NO 46
<211> LENGTH: 4173
<212> TYPE: DNA
<213> ORGANISM: Artificial Sequence
<220> FEATURE:
<223> OTHER INFORMATION: Synthetic pUC57-Ura3HA vector

<400> SEQUENCE: 46
gatgacggtg aaaacctctg acacatgcag ctcccggaga cggtcacagc ttgtctgtaa         60
gcggatgccg ggagcagaca gcccgtcag ggcgcgtcag cgggtgttgg cgggtgtcgg        120
ggctggctta actatgcggc atcagagcag attgtactga gagtgcacca tatgcggtgt        180
gaaataccgc acagatgcgt aaggagaaaa taccgcatca ggcgccattc gccattcagg        240
ctgcgcaact gttgggaagg gcgatcggtg cgggcctctt cgctattacg ccagctggcg        300
aaagggggat gtgctgcaag gcgattaagt tgggtaacgc cagggttttc ccagtcacga        360
cgttgtaaaa cgacggccag tgaattcgag ctcggtacct cgcgaatgca tctagatatc        420
ggatcccgac gagctgcacc gcggtggcgg ccgtatcttt acccatacg atgttcctga        480 ctatgcgggc tatccctatg acgtcccgga ctatgcagga tcctatccat atgacgttcc        540
agattacgct gctcagtgcg gccgcctgag agtgcaccat accacagctt tcaattcaa         600 ttcatcattt tttttttatt cttttttttg atttcggttt ctttgaaatt ttttgattc         660 ggtaatctcc gaacagaagg aagaacgaag gaaggagcac agacttagat tggtatatat        720
acgcatatgt agtgttgaag aaacatgaaa ttgcccagta ttcttaaccc aactgcacag        780
aacaaaaacc tgcaggaaac gaagataaat catgtcgaaa gctacatata aggaacgtgc        840
tgctactcat cctagtcctg ttgctgccaa gctatttaat atcatgcacg aaaagcaaac        900
```

```
aaacttgtgt gcttcattgg atgttcgtac caccaaggaa ttactggagt tagttgaagc      960
attaggtccc aaaatttgtt tactaaaaac acatgtggat atcttgactg attttttccat    1020 ggagggcaca gttaagccgc taaaggcatt atccgccaag tacaattttt tactcttcga    1080
agacagaaaa tttgctgaca ttggtaatac agtcaaattg cagtactctg cgggtgtata    1140
cagaatagca gaatgggcag acattacgaa tgcacacggt gtggtgggcc caggtattgt    1200
tagcggtttg aagcaggcgg cagaagaagt aacaaaggaa cctagaggcc ttttgatgtt    1260
agcagaattg tcatgcaagg gctccctatc tactggagaa tatactaagg gtactgttga    1320
cattgcgaag agcgacaaag attttgttat cggctttatt gctcaaagag acatgggtgg    1380
aagagatgaa ggttacgatt ggttgattat gacacccggt gtgggtttag atgacaaggg    1440
agacgcattg ggtcaacagt atagaaccgt ggatgatgtg gtctctacag gatctgacat    1500
tattattgtt ggaagaggac tatttgcaaa gggaagggat gctaaggtag agggtgaacg    1560
ttacagaaaa gcaggctggg aagcatattt gagaagatgc ggccagcaaa actaaaaaac    1620
tgtattataa gtaaatgcat gtatactaaa ctcacaaatt agagcttcaa tttaattata    1680
tcagttatta ccctatgcgg tgtgaaatac cgcacagatg cgtaaggaga aaataccgca    1740
tcaggaaatt gtagcggccg cgaatttgag cttatctttt acccatacga tgttcctgac    1800
tatgcgggct atccctatga cgtcccggac tatgcaggat cctatccata tgacgttcca    1860
gattacgcta ctagcggggg gcccggtgac gggcccgtcg actgcagagg cctgcatgca    1920
agcttggcgt aatcatggtc atagctgttt cctgtgtgaa attgttatcc gctcacaatt    1980
ccacacaaca tacgagccgg aagcataaag tgtaaagcct ggggtgccta atgagtgagc    2040
taactcacat taattgcgtt gcgctcactg cccgctttcc agtcgggaaa cctgtcgtgc    2100
cagctgcatt aatgaatcgg ccaacgcgcg gggagaggcg gtttgcgtat tgggcgctct    2160
tccgcttcct cgctcactga ctcgctgcgc tcggtcgttc ggctgcggcg agcggtatca    2220
gctcactcaa aggcggtaat acggttatcc acagaatcag gggataacgc aggaaagaac    2280
atgtgagcaa aaggccagca aaaggccagg aaccgtaaaa aggccgcgtt gctggcgttt    2340
ttccataggc tccgcccccc tgacgagcat cacaaaaatc gacgctcaag tcagaggtgg    2400
cgaaacccga caggactata aagataccag gcgtttcccc ctggaagctc cctcgtgcgc    2460
tctcctgttc cgaccctgcc gcttaccgga tacctgtccg cctttctccc ttcgggaagc    2520
gtggcgcttt ctcatagctc acgctgtagg tatctcagtt cggtgtaggt cgttcgctcc    2580
aagctgggct gtgtgcacga accccccgtt cagcccgacc gctgcgcctt atccggtaac    2640
tatcgtcttg agtccaaccc ggtaagacac gacttatcgc cactggcagc agccactggt    2700
aacaggatta gcagagcgag gtatgtaggc ggtgctacag agttcttgaa gtggtggcct    2760
aactacggct acactagaag aacagtattt ggtatctgcg ctctgctgaa gccagttacc    2820
ttcggaaaaa gagttggtag ctcttgatcc ggcaaacaaa ccaccgctgg tagcggtggt    2880
ttttttgttt gcaagcagca gattacgcgc agaaaaaaag gatctcaaga agatcctttg    2940
atcttttcta cggggtctga cgctcagtgg aacgaaaact cacgttaagg gattttggtc    3000
atgagattat caaaaaggat cttcacctag atccttttaa attaaaaatg aagttttaaa    3060
tcaatctaaa gtatatatga gtaaacttgg tctgacagtt accaatgctt aatcagtgag    3120
gcacctatct cagcgatctg tctatttcgt tcatccatag ttgcctgact ccccgtcgtg    3180
tagataacta cgatacggga gggcttacca tctggcccca gtgctgcaat gataccgcga    3240
```

```
gacccacgct caccggctcc agatttatca gcaataaacc agccagccgg aagggccgag    3300
cgcagaagtg gtcctgcaac tttatccgcc tccatccagt ctattaattg ttgccgggaa    3360
gctagagtaa gtagttcgcc agttaatagt ttgcgcaacg ttgttgccat tgctacaggc    3420
atcgtggtgt cacgctcgtc gtttggtatg gcttcattca gctccggttc caacgatca    3480 aggcgagtta catgatcccc catgttgtgc aaaaaagcgg ttagctcctt cggtcctccg    3540
atcgttgtca gaagtaagtt ggccgcagtg ttatcactca tggttatggc agcactgcat    3600
aattctctta ctgtcatgcc atccgtaaga tgcttttctg tgactggtga gtactcaacc    3660
aagtcattct gagaatagtg tatgcggcga ccgagttgct cttgcccggc gtcaatacgg    3720
gataataccg cgccacatag cagaacttta aaagtgctca tcattggaaa acgttcttcg    3780
gggcgaaaac tctcaaggat cttaccgctg ttgagatcca gttcgatgta acccactcgt    3840
gcacccaact gatcttcagc atcttttact ttcaccagcg tttctgggtg agcaaaaaca    3900
ggaaggcaaa atgccgcaaa aaagggaata agggcgacac ggaaatgttg aatactcata    3960
ctcttccttt ttcaatatta ttgaagcatt tatcagggtt attgtctcat gagcggatac    4020
atatttgaat gtatttagaa aaataaacaa ataggggttc gcgcacatt tccccgaaaa    4080 gtgccacctg acgtctaaga aaccattatt atcatgacat taacctataa aataggcgt    4140 atcacgaggc cctttcgtct cgcgcgtttc ggt                                 4173
```

<210> SEQ ID NO 47
<211> LENGTH: 62
<212> TYPE: DNA
<213> ORGANISM: Artificial Sequence
<220> FEATURE:
<223> OTHER INFORMATION: primer

<400> SEQUENCE: 47

```
gcttataaaa ctttaactaa taattagaga ttaaatcgct taaggtttcc cgactggaaa    60
gc                                                                   62
```

<210> SEQ ID NO 48
<211> LENGTH: 64
<212> TYPE: DNA
<213> ORGANISM: Artificial Sequence
<220> FEATURE:
<223> OTHER INFORMATION: primer

<400> SEQUENCE: 48

```
ctactcataa cctcacgcaa aataacacag tcaaatcaat caaaccagtc acgacgttgt    60
aaaa                                                                 64
```

<210> SEQ ID NO 49
<211> LENGTH: 65
<212> TYPE: DNA
<213> ORGANISM: Artificial Sequence
<220> FEATURE:
<223> OTHER INFORMATION: primer

<400> SEQUENCE: 49

```
ccgaaatgat tccctttcct gcacaacacg agatctttca cgcatccagt cacgacgttg    60
taaaa                                                                65
```

<210> SEQ ID NO 50
<211> LENGTH: 65
<212> TYPE: DNA
<213> ORGANISM: Artificial Sequence

```
<220> FEATURE:
<223> OTHER INFORMATION: primer

<400> SEQUENCE: 50
aaagtagcct taaagctagg ctataatcat gcatcctcaa attctaggtt tcccgactgg    60
aaagc                                                                65

<210> SEQ ID NO 51
<211> LENGTH: 70
<212> TYPE: DNA
<213> ORGANISM: Artificial Sequence
<220> FEATURE:
<223> OTHER INFORMATION: primer

<400> SEQUENCE: 51
ccctatgtct ctggccgatc acgcgccatt gtccctcaga aacaaatcaa ccagtcacga    60
cgttgtaaaa                                                           70

<210> SEQ ID NO 52
<211> LENGTH: 70
<212> TYPE: DNA
<213> ORGANISM: Artificial Sequence
<220> FEATURE:
<223> OTHER INFORMATION: primer

<400> SEQUENCE: 52
tagaagcaac tgtgccgaca gcctctgaat gagtggtgtt gtaaccaccc aggtttcccg    60
actggaaagc                                                           70

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
ggacgtaaag ggtagcctcc                                                20

<210> SEQ ID NO 54
<211> LENGTH: 22
<212> TYPE: DNA
<213> ORGANISM: Artificial Sequence
<220> FEATURE:
<223> OTHER INFORMATION: primer

<400> SEQUENCE: 54
gaagcggacc cagacttaag cc                                             22

<210> SEQ ID NO 55
<211> LENGTH: 25
<212> TYPE: DNA
<213> ORGANISM: Artificial Sequence
<220> FEATURE:
<223> OTHER INFORMATION: primer

<400> SEQUENCE: 55
cgcaagaacg tagtatccac atgcc                                          25

<210> SEQ ID NO 56
<211> LENGTH: 21
<212> TYPE: DNA
<213> ORGANISM: Artificial Sequence
<220> FEATURE:
```

```
<223> OTHER INFORMATION: primer

<400> SEQUENCE: 56
ggatatttac agaacgatgc g                                              21

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57
tcaatgagac tgttgtcctc ctact                                          25

<210> SEQ ID NO 58
<211> LENGTH: 24
<212> TYPE: DNA
<213> ORGANISM: Artificial Sequence
<220> FEATURE:
<223> OTHER INFORMATION: primer

<400> SEQUENCE: 58
tacatccttg tcgagccttg ggca                                           24

<210> SEQ ID NO 59
<211> LENGTH: 5999
<212> TYPE: DNA
<213> ORGANISM: Artificial Sequence
<220> FEATURE:
<223> OTHER INFORMATION: Synthetic pJ1214-mhpF vector

<400> SEQUENCE: 59
atgcagctca gattctttgt ttgaaaaatt agcgctctcg cgttgcattt ttgttttaca      60
aaaatgaagc acagattctt cgttggtaaa atagcgcttt cgcgttgcat ttctgttctg     120
taaaaatgca gctcagattc tttgtttgaa aaattagcgc tctcgcgttg cattttttgtt     180 ctacaaaatg aagcacagat gcttcgttca ggtggcactt tcggggaaa tgtgcgcgga      240 accctatttt gtttattttt ctaaatacat tcaaatatgt atccgctcat gagacaataa     300
ccctgatatt ggtcagaatt ggttaattgg ttgtaacact gacccctatt tgtttatttt     360
tctaaataca ttcaaatatg tatccgctca tgagacaata accctgataa atgcttcaat     420
aatattgaaa aaggaagaat atgagtattc aacatttccg tgtcgccctt attcccttttt    480 ttgcggcatt tgccttcct gttttgctc acccagaaac gctggtgaaa gtaaaagatg      540
ctgaagatca gttgggtgca cgagtgggtt acatcgaact ggatctcaac agcggtaaga    600
tccttgagag ttttcgcccc gaagaacgtt ttccaatgat gagcactttt aaagttctgc    660
tatgtggcgc ggtattatcc cgtattgacg ccgggcaaga gcaactcggt cgccgcatac    720
actattctca gaatgacttg gttgagtact caccagtcac agaaaagcat cttacggatg    780
gcatgacagt aagagaatta tgcagtgctg ccataaccat gagtgataac actgcggcca    840
acttacttct gacaacgatc ggaggaccga aggagctaac cgcttttttg cacaacatgg    900
gggatcatgt aactcgcctt gatcgttggg aaccggagct gaatgaagcc ataccaaacg    960
acgagcgtga caccacgatg cctgtagcga tggcaacaac gttgcgcaaa ctattaactg   1020
gcgaactact tactctagct tcccggcaac aattaataga ctggatggag gcggataaag   1080
ttgcaggacc acttctgcgc tcggcccttc cggctggctg gttattgct gataaatccg   1140 gagccggtga gcgtggttct cgcggtatca tcgcagcgct ggggccagat ggtaagccct   1200
```

```
cccgtatcgt agttatctac acgacgggga gtcaggcaac tatggatgaa cgaaatagac    1260
agatcgctga gataggtgcc tcactgatta agcattggta actcatgacc aaaatccctt    1320
aacgtgagtt acgcgcgcgt cgttccactg agcgtcagac cccgtagaaa agatcaaagg    1380
atcttcttga gatccttttt ttctgcgcgt aatctgctgc ttgcaaacaa aaaaaccacc    1440
gctaccagcg gtggtttgtt tgccggatca agagctacca actcttttc cgaaggtaac    1500 tggcttcagc agagcgcaga taccaaatac tgttcttcta gtgtagccgt agttagccca    1560
ccacttcaag aactctgtag caccgcctac atacctcgct ctgctaatcc tgttaccagt    1620
ggctgctgcc agtggcgata agtcgtgtct taccgggttg gactcaagac gatagttacc    1680
ggataaggcg cagcggtcgg gctgaacggg gggttcgtgc acacagccca gcttggagcg    1740
aacgacctac accgaactga gatacctaca gcgtgagcta tgagaaagcg ccacgcttcc    1800
cgaagggaga aggcggaca ggtatccggt aagcggcagg gtcggaacag gagagcgcac    1860
gagggagctt ccaggggaa acgcctggta tctttatagt cctgtcgggt ttcgccacct    1920
ctgacttgag cgtcgatttt tgtgatgctc gtcaggggg cggagcctat ggaaaaacgc    1980
cagcaacgcg gccttttac ggttcctggc cttttgctgg ccttttgctc acatgttctt    2040
tcctgcgtta tcccctgatt ctgtggataa ccgtattacc gcctttgagt gagctgatac    2100
cgctcggggt cgtgcaggta tagcttcaaa atgtttctac tcctttttta ctcttccaga    2160
ttttctcgga ctccgcgcat cgccgtacca cttcaaaaca cccaagcaca gcatactaaa    2220
tttcccctct ttcttcctct agggtgtcgt taattacccg tactaaaggt ttggaaaaga    2280
aaaaagtgac cgcctcgttt cttttcttc gtcgaaaaag gcaataaaaa tttttatcac    2340
gtttcttttt cttgaaaatt ttttttttg attttttct ctttcgatga cctcccattg    2400
atatttaagt taataaacgg acttcaattt ctcaagtttc agtttcattt ttcttgttct    2460
attacaactt tttttacttc ttgctcatta gaaagaaagc atagcaatct aatctaagtt    2520
taaaatgtca aagcgaaaag tagctatcat aggttcaggt aatattggta ctgatttgat    2580
gatcaaaatc ctgagacatg ccagcactt ggagatggcc gtcatggttg gtatcgaccc    2640
acaatccgat ggcttagcta gagctaggag aatgggtgtt gccacaactc acgaaggggt    2700
tattggctta atgaacatgc cagaatttgc agacatcgat atagttttg atgctactag    2760 tgcagggca catgtgaaaa acgacgcggc tttaagagaa gccaagccag atattagatt    2820
aattgatctt acccctgctg ctataggtcc ttactgcgtt cctgtagtta accttgaagc    2880
taatgtggac cagttgaacg tgaatatggt tacatgtggg ggccaagcta ccataccaat    2940
ggttgctgct gtctctagag tggccagagt acattatgcc gagatcattg cgtctatcgc    3000
atctaagtct gccggtcctg gaacaagggc taacatcgat gagttcactg agacaacctc    3060
tagagctatc gaagtagtag gaggcgcagc aaaaggtaaa gcgatcattg ttttgaatcc    3120
tgccgaacca cctttgatga tgagagatac ggtctacgtg ctatcagatg aagcttccca    3180
ggatgacatt gaagctagca ttaatgagat ggcagaagcc gttcaagcat acgtgccagg    3240
atatagactc aaacaaagag tccaatttga ggtcattcca caagacaagc cagttaatct    3300 cccagggtc ggtcaattct caggactaaa aactgctgtt tggttagaag tagaaggagc    3360
tgctcattac ctaccagcct acgccggtaa tttggatata atgacatctt ccgctcttgc    3420
aacagcagaa aagatggcac aaagtctggc ccgtaaggca ggagaagcgg cataataaat    3480
catgtaatta gttatgtcac gcttacattc acgccctccc cccacatccg ctctaaccga    3540
```

```
aaaggaagga gttagacaac ctgaagtcta ggtccctatt tatttttta  tagttatgtt   3600 agtattaaga acgttattta tatttcaaat ttttctttt  tttctgtaca gacgcgtgta   3660
cgcatgtaac attatactga aaaccttgct tgagaaggtt ttgggacgct cgaaggcttt   3720
aatttgcggc ccctcacctg cacgcaaaaa gcttttcaat tcaattcatc attttttt   3780 tattctttt  tttgatttcg gtttctttga aattttttg  attcggtaat ctccgaacag   3840
aaggaagaac gaaggaagga gcacagactt agattggtat atatacgcat atgtagtgtt   3900
gaagaaacat gaaattgccc agtattctta acccaactgc acagaacaaa accagcagg   3960 aaacgaagat aaatcatgtc gaaagctaca tataaggaac gtgctgctac tcatcctagt   4020
cctgttgctg ccaagctatt taatatcatg cacgaaaagc aaacaaactt gtgtgcttca   4080
ttggatgttc gtaccaccaa ggaattactg gagttagttg aagcattagg tcccaaaatt   4140
tgtttactaa aaacacatgt ggatatcttg actgatttt  ccatggaggg cacagttaag   4200
ccgctaaagg cattatccgc caagtacaat tttttactct tcgaagatag aaaatttgct   4260
gacattggta atacagtcaa attgcagtac tctgcgggtg tatacagaat agcagaatgg   4320
gcagacatta cgaatgcaca cggtgtggtg ggcccaggta ttgttagcgg tttgaagcag   4380
gcggcagaag aagtaacaaa ggaacctaga ggccttttga tgttagcaga attgtcatgc   4440
aagggctccc tatctactgg agaatatact aagggtactg ttgacattgc gaaaagcgac   4500
aaagattttg ttatcggctt tattgctcaa agagacatgg gtggaagaga tgaaggttac   4560
gattggttga ttatgacacc cggtgtgggt ttagatgaca agggagatgc attgggtcaa   4620
cagtatagaa ccgtggatga tgttgtctct acaggatctg acattattat tgttggaaga   4680
ggactatttg caagggaag  ggatgctaag gtagagggtg aacgttacag aaaagcaggc   4740
tgggaagcat atttgagaag atgcggccag caaaactaaa aaactgtatt ataagtaaat   4800
gcatgtatac taaactcaca aattagagct tcaattaat  tatatcagtt attcccacg    4860 ctatgatcca atatcaaagg aaatgatagc attgaaggat gagactaatc caattgagga   4920
gtggcagcat atagaacagc taaagggtag tgctgaagga agcatacgat accccgcatg   4980
gaatgggata atatcacagg aggtactaga ctacctttca tcctacataa atagacgcat   5040
ataagtacgc atttaagcat aaacacgcac tatgccgttc ttctcatgta tatatatata   5100
caggcaacac gcagatatag gtgcgacgtg aacagtgagc tgtatgtgcg cagctcgcgt   5160
tgcattttcg gaagcgctcg ttttcggaaa cgctttgaag ttcctattcc gaagttccta   5220
ttctctagaa agtataggaa cttcagagcg cttttgaaaa ccaaaagcgc tctgaagtcg   5280
cactttcaaa aaaccaaaaa cgcaccggac tgtaacgagc tactaaaata ttgcgaatac   5340
cgcttccaca acattgctc  aaagtatct  ctttgctata tatctctgtg ctatatccct   5400
atataaccta cccatccacc tttcgctcct tgaacttgca tctaaactcg acctctacat   5460
tttttatgtt tatctctagt attactcttt agacaaaaaa attgtagtaa gaactattca   5520
tagagtgaat cgaaaacaat acgaaaatgt aaacatttcc tatacgtagt atatagagac   5580
aaaatagaag aaaccgttca taattttctg accaatgaag aatcatcaac gctatcactt   5640
tctgttcaca agtatgcgc  aatccacatc ggtatagaat ataatcgggg atgcctttat   5700
cttgaaaaaa tgcacccgca gcttcgctag taatcagtaa acgcgggaag tggagtcagg   5760 cttttttat  ggaagagaaa atagacacca agtagccctt cttctaacct taacggacct   5820
acagtgcaaa aagttatcaa gagactgcat tatagagcgc acaaaggaga aaaaagtaa   5880 tctaagatgc tttgttagaa aaatagcgct ctcgggatgc atttttgtag aacaaaaaag   5940
```

-continued

```
aagtatagat tctttgttgg taaaatagcg ctctcgcgtt gcatttctgt tctgtaaaa    5999
```

<210> SEQ ID NO 60
<211> LENGTH: 5779
<212> TYPE: DNA
<213> ORGANISM: Artificial Sequence
<220> FEATURE:
<223> OTHER INFORMATION: Synthetic pUC19-His-MhpF

<400> SEQUENCE: 60

```
tcgacctgca ggcatgcaag cttggcgtaa tcatggtcat agctgtttcc tgtgtgaaat      60
tgttatccgc tcacaattcc acacaacata cgagccggaa gcataaagtg taaagcctgg     120
ggtgcctaat gagtgagcta actcacatta attgcgttgc gctcactgcc cgctttccag     180
tcgggaaacc tgtcgtgcca gctgcattaa tgaatcggcc aacgcgcggg gagaggcggt     240
ttgcgtattg ggcgctcttc cgcttcctcg ctcactgact cgctgcgctc ggtcgttcgg     300
ctgcggcgag cggtatcagc tcactcaaag gcggtaatac ggttatccac agaatcaggg     360
gataacgcag gaaagaacat gtgagcaaaa ggccagcaaa aggccaggaa ccgtaaaaag     420
gccgcgttgc tggcgttttt ccataggctc cgcccccctg acgagcatca caaaaatcga     480
cgctcaagtc agaggtggcg aaacccgaca ggactataaa gataccaggc gtttccccct     540
ggaagctccc tcgtgcgctc tcctgttccg accctgccgc ttaccggata cctgtccgcc     600
tttctccctt cgggaagcgt ggcgctttct catagctcac gctgtaggta tctcagttcg     660
gtgtaggtcg ttcgctccaa gctgggctgt gtgcacgaac cccccgttca gcccgaccgc     720
tgcgccttat ccggtaacta tcgtcttgag tccaacccgg taagacacga cttatcgcca     780
ctggcagcag ccactggtaa caggattagc agagcgaggt atgtaggcgg tgctacagag     840
ttcttgaagt ggtggcctaa ctacggctac actagaagaa cagtatttgg tatctgcgct     900
ctgctgaagc cagttacctt cggaaaaaga gttggtagct cttgatccgg caaacaaacc     960
accgctggta gcggtggttt ttttgtttgc aagcagcaga ttacgcgcag aaaaaaagga    1020
tctcaagaag atcctttgat cttttctacg gggtctgacg ctcagtggaa cgaaaactca    1080
cgttaaggga ttttggtcat gagattatca aaaaggatct tcacctagat ccttttaaat    1140
taaaaatgaa gttttaaatc aatctaaagt atatatgagt aaacttggtc tgacagttac    1200
caatgcttaa tcagtgaggc acctatctca gcgatctgtc tatttcgttc atccatagtt    1260
gcctgactcc ccgtcgtgta gataactacg atacgggagg gcttaccatc tggccccagt    1320
gctgcaatga taccgcgaga cccacgctca ccggctccag atttatcagc aataaaccag    1380
ccagccggaa gggccgagcg cagaagtggt cctgcaactt tatccgcctc catccagtct    1440
attaattgtt gccgggaagc tagagtaagt agttcgccag ttaatagttt gcgcaacgtt    1500
gttgccattg ctacaggcat cgtggtgtca cgctcgtcgt ttggtatggc ttcattcagc    1560
tccggttccc aacgatcaag gcgagttaca tgatccccca tgttgtgcaa aaaagcggtt    1620
agctccttcg gtcctccgat cgttgtcaga agtaagttgg ccgcagtgtt atcactcatg    1680
gttatggcag cactgcataa ttctcttact gtcatgccat ccgtaagatg cttttctgtg    1740
actggtgagt actcaaccaa gtcattctga gaatagtgta tgcggcgacc gagttgctct    1800
tgcccggcgt caatacggga taataccgcg ccacatagca gaactttaaa agtgctcatc    1860
attggaaaac gttcttcggg gcgaaaactc tcaaggatct taccgctgtt gagatccagt    1920
tcgatgtaac ccactcgtgc acccaactga tcttcagcat cttttacttt caccagcgtt    1980
```

```
tctgggtgag caaaaacagg aaggcaaaat gccgcaaaaa agggaataag ggcgacacgg    2040
aaatgttgaa tactcatact cttccttttt caatattatt gaagcattta tcagggttat    2100
tgtctcatga gcggatacat atttgaatgt atttagaaaa ataaacaaat aggggttccg    2160
cgcacatttc cccgaaaagt gccacctgac gtctaagaaa ccattattat catgacatta    2220
acctataaaa ataggcgtat cacgaggccc tttcgtctcg cgcgtttcgg tgatgacggt    2280
gaaaacctct gacacatgca gctcccggag acggtcacag cttgtctgta agcggatgcc    2340
gggagcagac aagcccgtca gggcgcgtca gcgggtgttg gcgggtgtcg ggctggctt    2400 aactatgcgg catcagagca gattgtactg agagtgcacc atatgcggtg tgaaataccg    2460
cacagatgcg taaggagaaa ataccgcatc aggcgccatt cgccattcag gctgcgcaac    2520
tgttgggaag ggcgatcggt gcgggcctct cgctattac gccagctggc gaaaggggga    2580
tgtgctgcaa ggcgattaag ttgggtaacg ccagggtttt cccagtcacg acgttgtaaa    2640
acgacggcca gtgaattcga gctcagttta tcattatcaa tactcgccat ttcaaagaat    2700
acgtaaataa ttaatagtag tgattttcct aactttattt agtcaaaaaa ttagccttt    2760 aattctgctg taacccgtac atgcccaaaa taggggcgg gttacacaga atatataaca    2820
tcgtaggtgt ctgggtgaac agtttattcc tggcatccac taaatataat ggagcccgct    2880
ttttaagctg gcatccagaa aaaaaaagaa tcccagcacc aaaatattgt tttcttcacc    2940
aaccatcagt tcataggtcc attctcttag cgcaactaca gagaacaggg gcacaaacag    3000
gcaaaaaacg ggcacaacct caatggagtg atgcaacctg cctggagtaa atgatgacac    3060
aaggcaattg acccacgcat gtatctatct cattttctta caccttctat taccttctgc    3120
tctctctgat ttggaaaaag ctgaaaaaaa aggttgaaac cagttccctg aaattattcc    3180
cctacttgac taataagtat ataaagacgg taggtattga ttgtaattct gtaaatctat    3240
ttcttaaact tcttaaattc tacttttata gttagtcttt tttttagttt taaaacacca    3300
gaacttagtt tcgacggatt ctagaactag tggatccatg tcaaagcgaa aagtagctat    3360
cataggttca ggtaatattg gtactgattt gatgatcaaa atcctgagac atggccagca    3420
cttggagatg gccgtcatgg ttggtatcga cccacaatcc gatggcttag ctagagctag    3480
gagaatgggt gttgccacaa ctcacgaagg ggttattggc ttaatgaaca tgccagaatt    3540
tgcagacatc gatatagttt ttgatgctac tagtgcaggg gcacatgtga aaaacgacgc    3600
ggctttaaga gaagccaagc cagatattag attaattgat cttacccctg ctgctatagg    3660
tccttactgc gttcctgtag ttaaccttga agctaatgtg gaccagttga acgtgaatat    3720
ggttacatgt ggtggccaag ctaccatacc aatggttgct gctgtctcta gagtggccag    3780
agtacattat gccgagatca ttgcgtctat cgcatctaag tctgccggtc ctggaacaag    3840
ggctaacatc gatgagttca ctgagacaac ctctagagct atcgaagtag taggaggcgc    3900
agcaaaaggt aaagcgatca ttgttttgaa tcctgccgaa ccacctttga tgatgagaga    3960
tacggtctac gtgctatcag atgaagcttc ccaggatgac attgaagcta gcattaatga    4020
gatggcagaa gccgttcaag catacgtgcc aggatataga ctcaaacaaa gagtccaatt    4080
tgaggtcatt ccacaagaca agccagttaa tctcccaggg gtcggtcaat ctcaggact    4140 aaaaactgct gtttggttag aagtagaagg agctgctcat tacctaccag cctacgccgg    4200
taatttggat ataatgacat cttccgctct tgcaacagca gaaagatgg cacaaagtct    4260 ggcccgtaag gcaggagaag cggcataata aatcctcgag tcatgtaatt agttatgtca    4320
cgcttacatt cacgccctcc ccccacatcc gctctaaccg aaaaggaagg agttagacaa    4380
```

-continued

```
cctgaagtct aggtccctat ttatttttt atagttatgt tagtattaag aacgttattt    4440
atatttcaaa tttttctttt ttttctgtac agacgcgtgt acgcatgtaa cattatactg    4500
aaaaccttgc ttgagaaggt tttgggacgc tcgaaggctt taatttgcgg ccggtaccca    4560
attcgagctc ggtacccggg gatcctctag agtcgacaat tcccgtttta agagcttggt    4620
gagcgctagg agtcactgcc aggtatcgtt tgaacacggc attagtcagg gaagtcataa    4680
cacagtcctt tcccgcaatt ttcttttct attactcttg gcctcctcta gtacactcta    4740
tattttttta tgcctcggta atgattttca ttttttttt tccctagcg gatgactctt     4800 ttttttctt agcgattggc attatcacat aatgaattat acattatata agtaatgtg     4860 atttcttcga agaatatact aaaaaatgag caggcaagat aaacgaaggc aaagatgaca    4920
gagcagaaag ccctagtaaa gcgtattaca atgaaaccca agattcagat tgcgatctct    4980
ttaaagggtg gtcccctagc gatagagcac tcgatcttcc cagaaaaaga ggcagaagca    5040
gtagcagaac aggccacaca atcgcaagtg attaacgtcc acacaggtat agggtttctg    5100
gaccatatga tacatgctct ggccaagcat tccggctggt cgctaatcgt tgagtgcatt    5160
ggtgacttac acatagacga ccatcacacc actgaagact gcgggattgc tctcggtcaa    5220
gcttttaaag aggccctact ggcgcgtgga gtaaaaaggt ttggatcagg atttgcgcct    5280
ttggatgagg cactttccag agcggtggta gatctttcga acaggccgta cgcagttgtc    5340
gaacttggtt tgcaaaggga gaaagtagga gatctctctt gcgagatgat cccgcatttt    5400
cttgaaagct ttgcagaggc tagcagaatt accctccacg ttgattgtct gcgaggcaag    5460
aatgatcatc accgtagtga gagtgcgttc aaggctcttg cggttgccat aagagaagcc    5520
acctcgccca atggtaccaa cgatgttccc tccaccaaag gtgttcttat gtagtgacac    5580
cgattattta aagctgcagc atacgatata tatacatgtg tatatatgta tacctatgaa    5640
tgtcagtaag tatgtatacg aacagtatga tactgaagat gacaaggtaa tgcatcattc    5700
tatacgtgtc attctgaacg aggcgcgctt tccttttttc ttttgcttt ttctttttt     5760 ttctcttgaa ctcgacggg                                                 5779
```

<210> SEQ ID NO 61
<211> LENGTH: 31
<212> TYPE: DNA
<213> ORGANISM: Artificial Sequence
<220> FEATURE:
<223> OTHER INFORMATION: primer

<400> SEQUENCE: 61
cctcctgagt cgacaattcc cgttttaaga g                               31

<210> SEQ ID NO 62
<211> LENGTH: 30
<212> TYPE: DNA
<213> ORGANISM: Artificial Sequence
<220> FEATURE:
<223> OTHER INFORMATION: primer

<400> SEQUENCE: 62
cgaccgtggt cgaccgtcg agttcaagag                                  30

<210> SEQ ID NO 63
<211> LENGTH: 67
<212> TYPE: DNA
<213> ORGANISM: Artificial Sequence
<220> FEATURE:

<223> OTHER INFORMATION: primer

<400> SEQUENCE: 63
tatatatttc aaggatatac cattctaatg tctgcccta agaagatcgt gctgcaaggc    60
gattaag    67

<210> SEQ ID NO 64
<211> LENGTH: 67
<212> TYPE: DNA
<213> ORGANISM: Artificial Sequence
<220> FEATURE:
<223> OTHER INFORMATION: primer

<400> SEQUENCE: 64
gagaatcttt ttaagcaagg attttcttaa cttcttcggc gacagcatcg gctcgtatgt    60
tgtgtgg    67

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
gtttcgtcta ccctatgaac    20

<210> SEQ ID NO 66
<211> LENGTH: 21
<212> TYPE: DNA
<213> ORGANISM: Artificial Sequence
<220> FEATURE:
<223> OTHER INFORMATION: primer

<400> SEQUENCE: 66
ccaataggtg gttagcaatc g    21

<210> SEQ ID NO 67
<211> LENGTH: 64
<212> TYPE: DNA
<213> ORGANISM: Artificial Sequence
<220> FEATURE:
<223> OTHER INFORMATION: primer

<400> SEQUENCE: 67
caagaaacat ctttaacata cacaaacaca tactatcaga atacccagtc acgacgttgt    60
aaaa    64

<210> SEQ ID NO 68
<211> LENGTH: 65
<212> TYPE: DNA
<213> ORGANISM: Artificial Sequence
<220> FEATURE:
<223> OTHER INFORMATION: primer

<400> SEQUENCE: 68
gtattttgtg tatatgacgg aaagaaatgc aggttggtac attacaggtt tcccgactgg    60
aaagc    65

<210> SEQ ID NO 69
<211> LENGTH: 24
<212> TYPE: DNA
<213> ORGANISM: Artificial Sequence
<220> FEATURE:
<223> OTHER INFORMATION: primer

<400> SEQUENCE: 69
gcatcgggaa cgtatgtaac attg                                    24

<210> SEQ ID NO 70
<211> LENGTH: 19
<212> TYPE: DNA
<213> ORGANISM: Artificial Sequence
<220> FEATURE:
<223> OTHER INFORMATION: primer

<400> SEQUENCE: 70
tgacgtaaga ccaagtaag                                          19

<210> SEQ ID NO 71
<211> LENGTH: 55
<212> TYPE: DNA
<213> ORGANISM: Artificial Sequence
<220> FEATURE:
<223> OTHER INFORMATION: primer

<400> SEQUENCE: 71
ctatagggcg aattggctag cttatcatta tcaatactcg ccatttcaaa gaata   55

<210> SEQ ID NO 72
<211> LENGTH: 66
<212> TYPE: DNA
<213> ORGANISM: Artificial Sequence
<220> FEATURE:
<223> OTHER INFORMATION: primer

<400> SEQUENCE: 72
ctcgaggggg ggcccggtac ctcgaaacta agttctggtg ttttaaaact aaaaaaaga   60 ctaact                                                            66

<210> SEQ ID NO 73
<211> LENGTH: 6110
<212> TYPE: DNA
<213> ORGANISM: Artificial Sequence
<220> FEATURE:
<223> OTHER INFORMATION: Synthetic pCS-Ex1 vector

<400> SEQUENCE: 73
ctaaattgta agcgttaata ttttgttaaa attcgcgtta aatttttgtt aaatcagctc   60
attttttaac caataggccg aaatcggcaa atcccttat aaatcaaaag aatagaccga   120
gatagggttg agtacgcatt taagcataaa cacgcactat gccgttcttc tcatgtatat   180
atatatacag gcaacacgca gatataggtg cgacgtgaac agtgagctgt atgtgcgcag   240
ctcgcgttgc attttcggaa gcgctcgttt tcggaaacgc tttgaagttc ctattccgaa   300
gttcctattc tctagctaga agtatagga acttcagagc gcttttgaaa accaaaagcg   360
ctctgaagac gcactttcaa aaaccaaaa acgcaccgga ctgtaacgag ctactaaaat   420
attgcgaata ccgcttccac aaacattgct caaaagtatc tctttgctat atatctctgt   480
gctatatccc tatataacct acccatccac ctttcgctcc ttgaacttgc atctaaactc   540
gacctctaca tttttatgt ttatctctag tattactctt tagacaaaaa aattgtagta   600
agaactattc atagagtgaa tcgaaaacaa tacgaaaatg taaacatttc ctatacgtag   660
tatatagaga caaaatagaa gaaaccgttc ataatttct gaccaatgaa gaatcatcaa   720

```
cgctatcact ttctgttcac aaagtatgcg caatccacat cggtatagaa tataatcggg      780
gatgccttta tcttgaaaaa atgcacccgc agcttcgcta gtaatcagta aacgcgggaa      840
gtggagtcag gcttttttta tggaagagaa aatagacacc aaagtagcct tcttctaacc      900
ttaacggacc tacagtgcaa aaagttatca agagactgca ttatagagcg cacaaaggag      960
aaaaaaagta atctaagatg ctttgttaga aaaatagcgc tctcgggatg cattttttgta    1020 gaacaaaaaa gaagtataga ttctttgttg gtaaaatagc gctctcgcgt tgcatttctg     1080
ttctgtaaaa atgcagctca gattctttgt ttgaaaaatt agcgctctcg cgttgcattt     1140
ttgttttaca aaaatgaagc acagattctt cgttggtaaa atagcgcttt cgcgttgcat     1200
ttctgttctg taaaaatgca gctcagattc tttgtttgaa aaattagcgc tctcgcgttg     1260 cattttttgtt ctacaaaatg aagcacagat gcttcgttaa tgtgctgcaa ggcgattaag    1320
ttgggtaacg ccagggtttt cccagtcacg acgttgtaaa acgacggcca gtgaattgta     1380
atacgactca ctatagggcg aattggctag cttatcatta tcaatactcg ccatttcaaa    1440
gaatacgtaa ataattaata gtagtgattt tcctaacttt atttagtcaa aaaattagcc    1500
ttttaattct gctgtaaccc gtacatgccc aaaatagggg gcgggttaca cagaatatat    1560
aacatcgtag gtgtctgggt gaacagttta ttcctggcat ccactaaata taatggagcc    1620 cgcttttaa gctggcatcc agaaaaaaaa agaatcccag caccaaaata ttgttttctt     1680
caccaaccat cagttcatag gtccattctc ttagcgcaac tacagagaac aggggcacaa    1740
acaggcaaaa aacgggcaca acctcaatgg agtgatgcaa cctgcctgga gtaaatgatg    1800
acacaaggca attgacccac gcatgtatct atctcatttt cttacacctt ctattacctt    1860
ctgctctctc tgatttggaa aaagctgaaa aaaaaggttg aaaccagttc cctgaaatta    1920
ttcccctact tgactaataa gtatataaag acggtaggta ttgattgtaa ttctgtaaat    1980
ctatttctta aacttcttaa attctacttt tatagttagt cttttttttta gttttaaaac    2040 accagaactt agtttcgagg taccgggccc cccctcgagg tcgacggtat cgataagctt    2100
gatatcgaat tcctgcagcc cggggggatcc actagttcta gagcggccgc caccgcggtg    2160
gagctcggtt ctgcttatcc ttacgacgtg cctgactacg cctgaacccg atgcaaatga    2220
gacgatcgtc tattcctggt ccggttttct ctgccctctc ttctattcac ttttttttata    2280 ctttatataa aattatataa atgacataac tgaaacgcca cacgtcctct cctattcgtt    2340
aacgcctgtc tgtagcgctg ttactgaagc tgcgcaagta gttttttcac cgtataggcc    2400
ctctttttct ctctctttct ttctctcccg cgctgatctc ttcttcgaaa cacagagtgc    2460
accataccac cttttcaatt catcattttt tttttattct tttttttgat ttcggtttcc    2520
ttgaaatttt tttgattcgg taatctccga acagaaggaa gaacgaagga aggagcacag    2580
acttagattg gtatatatac gcatatgtag tgttgaagaa acatgaaatt gcccagtatt    2640
cttaacccaa ctgcacagaa caaaaacctc caggaaacga agataaatca tgtcgaaagc    2700
tacatataag gaacgtgctg ctactcatcc tagtcctgtt gctgccaagc tatttaatat    2760
catgcacgaa aagcaaacaa acttgtgtgc ttcattggat gttcgtacca ccaaggaatt    2820
actggagtta gttgaagcat taggtcccaa aatttgttta ctaaaaacac atgtggatat    2880
cttgactgat ttttccatgg agggcacagt taagccgcta aaggcattat ccgccaagta    2940
caatttttta ctcttcgaag acagaaaatt tgctgacatt ggtaatacag tcaaattgca    3000
gtactctgcg ggtgtataca gaatagcaga atgggcagac attacgaatg cacacggtgt    3060
ggtgggccca ggtattgtta gcggtttgaa gcaggcggca gaagaagtaa caaaggaacc    3120
```

```
tagaggccttt tgatgttag cagaattgtc atgcaagggc tccctatcta ctggagaata   3180
tactaagggt actgttgaca ttgcgaagag cgacaaagat tttgttatcg gctttattgc   3240
tcaaagagac atgggtggaa gagatgaagg ttacgattgg ttgattatga cacccggtgt   3300
gggtttagat gacaagggag acgcattggg tcaacagtat agaaccgtgg atgatgtggt   3360
ctctacagga tctgacatta ttattgttgg aagaggacta tttgcaaagg aagggatgc    3420 taaggtagag ggtgaacgtt acagaaaagc aggctgggaa gcatatttga aagatgcgg    3480 ccagcaaaac taatcatgta attagttatg tcacgcttac attcacgccc tcccccaca   3540 tccgctctaa ccgaaaagga aggagttaga caacctgaag tctaggtccc tatttatttt   3600
tttatagtta tgttagtatt aagaacgtta tttatatttc aaattttttct tttttttctg  3660 tacagacgcg tgtacgcatg taacattata ctgaaaacct tgcttgagaa ggttttggga   3720
cgctcgaagg ctttaatttg cgtctgtagc gctgttactg aagctgcgca agtagttttt   3780
tcaccgtata ggccctcttt ttctctctct ttctttctct cccgcgctga tctcttcttc   3840
gaaacatcat gaataaaaag aaaaaggaaa tcaagaaaaa aagccataa tttatcccac    3900 atttttttt attgtcgctg ttcacaccgc ataacgaaga tattggctag ctaaccagct    3960
tttgttccct ttagtgaggg ttaatttcga gcttggcgta atcatggtca tagctgtttc   4020
ctgtgtgaaa ttgttatccg ctcacaattc cacacaacat acgagccgga agcataaagt   4080
gtaaagcctg gggtgcctaa tgagtgagct aactcacatt aattgcgttg cgctcactgc   4140
ccgctttcca gtcgggaaac ctgtcgtgcc agctgcatta atgaatcggc caacgcgcgg   4200
ggagaggcgg tttgcgtatt gggcgctctt ccgcttcctc gctcactgac tcgctgcgct   4260
cggtcgttcg gctgcggcga gcggtatcag ctcactcaaa ggcggtaata cggttatcca   4320
cagaatcagg ggataacgca ggaaagaaca tgtgagcaaa aggccagcaa aaggccagga   4380
accgtaaaaa ggccgcgttg ctggcgtttt tccataggct ccgcccccct gacgagcatc   4440
acaaaaatcg acgctcaagt cagaggtggc gaaacccgac aggactataa agataccagg   4500
cgtttccccc tggaagctcc ctcgtgcgct ctcctgttcc gaccctgccg cttaccggat   4560
acctgtccgc ctttctccct tcgggaagcg tggcgctttc tcatagctca cgctgtaggt   4620
atctcagttc ggtgtaggtc gttcgctcca agctgggctg tgtgcacgaa ccccccgttc   4680
agcccgaccg ctgcgcctta tccggtaact atcgtcttga gtccaacccg gtaagacacg   4740
acttatcgcc actggcagca gccactggta acaggattag cagagcgagg tatgtaggcg   4800
gtgctacaga gttcttgaag tggtggccta actacggcta cactagaagg acagtatttg   4860
gtatctgcgc tctgctgaag ccagttacct tcggaaaaag agttggtagc tcttgatccg   4920
gcaaacaaac caccgctggt agcggtggtt tttttgtttg caagcagcag attacgcgca   4980
gaaaaaaagg atctcaagaa gatcctttga tcttttctac ggggtctgac gctcagtgga   5040
acgaaaactc acgttaaggg attttggtca tgagattatc aaaaaggatc ttcacctaga   5100
tccttttaaa ttaaaaatga agttttaaat caatctaaag tatatatgag taaacttggt   5160
ctgacatcag aagaactcgt caagaaggcg atagaaggcg atgcgctgcg aatcgggagc   5220 ggcgatacccg taaagcacga ggaagcggtc agcccattcg ccgccaagct cttcagcaat   5280
atcacgggta gccaacgcta tgtcctgata gcggtccgcc acacccagcc ggccacagtc   5340
gatgaatcca gaaaagcggc catttttccac catgatattc ggcaagcagg catcgccatg   5400
ggtcacgacg agatcctcgc cgtcgggcat gctcgccttg agcctggcga acagttcggc   5460
```

```
tggcgcgagc ccctgatgct cttcgtccag atcatcctga tcgacaagac cggcttccat    5520
ccgagtacgt gctcgctcga tgcgatgttt cgcttggtgg tcgaatgggc aggtagccgg    5580
atcaagcgta tgcagccgcc gcattgcatc agccatgatg gatactttct cggcaggagc    5640
aaggtgagat gacaggagat cctgccccgg cacttcgccc aatagcagcc agtcccttcc    5700
cgcttcagtg acaacgtcga gcacagctgc gcaaggaacg cccgtcgtgg ccagccacga    5760
tagccgcgct gcctcgtctt gcagttcatt cagggcaccg acaggtcgg tcttgacaaa     5820 aagaaccggg cgcccctgcg ctgacagccg gaacacggcg gcatcagagc agccgattgt    5880
ctgttgtgcc cagtcatagc cgaatagcct ctccacccaa gcggccggag aacctgcgtg    5940
caatccatct tgttcaattc gagtgcattc aacatcagcc atactcttcc tttttcaata    6000
ttattgaagc atttatcagg gttattgtct catgagcgga tacatatttg aatgtattta    6060
gaaaaataaa caaatagggg ttccgcgcac atttccccga aaagtgccac                6110
```

<210> SEQ ID NO 74
<211> LENGTH: 55
<212> TYPE: DNA
<213> ORGANISM: Artificial Sequence
<220> FEATURE:
<223> OTHER INFORMATION: primer

<400> SEQUENCE: 74

```
accagaactt agtttcgaga aacaatgaat caacaggata ttgaacaggt ggtga           55
```

<210> SEQ ID NO 75
<211> LENGTH: 50
<212> TYPE: DNA
<213> ORGANISM: Artificial Sequence
<220> FEATURE:
<223> OTHER INFORMATION: primer

<400> SEQUENCE: 75

```
gtaaggataa gcagaaccgt taaacaatgc gaaacgcatc gactaataca                 50
```

<210> SEQ ID NO 76
<211> LENGTH: 7413
<212> TYPE: DNA
<213> ORGANISM: Artificial Sequence
<220> FEATURE:
<223> OTHER INFORMATION: Synthetic MD1040 vector

<400> SEQUENCE: 76

```
ctaaattgta agcgttaata ttttgttaaa attcgcgtta aattttgtt aaatcagctc       60 attttttaac caataggccg aaatcggcaa aatcccttat aaatcaaaag aatagaccga      120
gatagggttg agtacgcatt taagcataaa cacgcactat gccgttcttc tcatgtatat     180
atatatacag gcaacacgca gatataggtg cgacgtgaac agtgagctgt atgtgcgcag     240
ctcgcgttgc attttcggaa gcgctcgttt cggaaacgc tttgaagttc ctattccgaa      300
gttcctattc tctagctaga aagtatagga acttcagagc gcttttgaaa accaaaagcg     360
ctctgaagac gcactttcaa aaaccaaaa acgcaccgga ctgtaacgag ctactaaaat      420
attgcgaata ccgcttccac aaacattgct caaaagtatc tctttgctat atatctctgt    480
gctatatccc tatataacct acccatccac ctttcgctcc ttgaacttgc atctaaactc    540
gacctctaca ttttttatgt ttatctctag tattactctt tagacaaaaa aattgtagta    600
agaactattc atagagtgaa tcgaaaacaa tacgaaaatg taaacatttc ctacgcgtag    660
tatatagaga caaaatagaa gaaaccgttc ataattttct gaccaatgaa gaatcatcaa    720
```

```
cgctatcact ttctgttcac aaagtatgcg caatccacat cggtatagaa tataatcggg      780
gatgccttta tcttgaaaaa atgcacccgc agcttcgcta gtaatcagta aacgcgggaa      840
gtggagtcag gctttttta tggaagagaa aatagacacc aaagtagcct tcttctaacc       900
ttaacggacc tacagtgcaa aaagttatca agagactgca ttatagagcg cacaaaggag      960
aaaaaaagta atctaagatg ctttgttaga aaaatagcgc tctcgggatg cattttgta     1020 gaacaaaaaa gaagtataga ttctttgttg gtaaaatagc gctctcgcgt tgcatttctg     1080
ttctgtaaaa atgcagctca gattctttgt ttgaaaaatt agcgctctcg cgttgcattt     1140
ttgttttaca aaaatgaagc acagattctt cgttggtaaa atagcgcttt cgcgttgcat     1200
ttctgttctg taaaaatgca gctcagattc tttgtttgaa aaattagcgc tctcgcgttg     1260 cattttgtt ctacaaaatg aagcacagat gcttcgttaa tgtgctgcaa ggcgattaag     1320
ttgggtaacg ccagggtttt cccagtcacg acgttgtaaa acgacggcca gtgaattgta     1380
atacgactca ctatagggcg aattggctag cttatcatta tcaatactcg ccatttcaaa     1440
gaatacgtaa ataattaata gtagtgattt tcctaacttt atttagtcaa aaaattagcc     1500
ttttaattct gctgtaaccc gtacatgccc aaaataggg gcgggttaca cagaatatat      1560
aacatcgtag gtgtctgggt gaacagttta ttcctggcat ccactaaata taatggagcc     1620 cgcttttaa gctggcatcc agaaaaaaa agaatcccag caccaaaata ttgttttctt      1680
caccaaccat cagttcatag gtccattctc ttagcgcaac tacagagaac aggggcacaa     1740
acaggcaaaa aacgggcaca acctcaatgg agtgatgcaa cctgcctgga gtaaatgatg     1800
acacaaggca attgacccac gcatgtatct atctcatttt cttacacctt ctattacctt     1860
ctgctctctc tgatttggaa aaagctgaaa aaaaggttg aaaccagttc cctgaaatta      1920
ttcccctact tgactaataa gtatataaag acggtaggta ttgattgtaa ttctgtaaat     1980
ctatttctta aacttcttaa attctacttt tatagttagt ctttttttta gttttaaaac     2040
accagaactt agtttcgaga aacaatgaat caacaggata ttgaacaggt ggtgaaagcg     2100
gtactgctga aaatgcaaag cagtgacacg ccgtccgccg ccgttcatga gatgggcgtt     2160
ttcgcgtccc tggatgacgc cgttgcggca gccaaagtcg cccagcaagg gttaaaaagc     2220
gtggcaatgc gccagttagc cattgctgcc attcgtgaag caggcgaaaa acacgccaga     2280
gatttagcgg aacttgccgt cagtgaaacc ggcatggggc gcgttgaaga taaatttgca     2340
aaaaacgtcg ctcaggcgcg cggcacacca ggcgttgagt gcctctctcc gcaagtgctg     2400
actggcgaca acggcctgac cctaattgaa acgcaccct ggggcgtggt ggcttcggtg      2460
acgccttcca ctaacccggc ggcaaccgta attaacaacg ccatcagcct gattgccgcg     2520
ggcaacagct catttttgc cccgcatccg cggcgaaaa aagtctccca gcgggcgatt      2580
acgctgctca accaggcgat tgttgccgca ggtgggccgg aaaacttact ggttactgtg     2640
gcaaatccgg atatcgaaac cgcgcaacgc ttgttcaagt ttccgggtat cggcctgctg     2700
gtggtaaccg gcggcgaagc ggtagtagaa gcggcgcgta acacaccaa taaacgtctg     2760 attgccgcag gcgctggcaa cccgccggta gtggtggatg aaaccgccga cctcgcccgt     2820
gccgctcagt ccatcgtcaa aggcgcttct ttcgataaca acatcatttg tgccgacgaa     2880
aaggtactga ttgttgttga tagcgtagcc gatgaactga tgcgtctgat ggaaggccag     2940
cacgcggtga aactgaccgc agaacaggcg cagcagctgc aaccggtgtt gctgaaaaat     3000
atcgacgagc gcggaaaagg caccgtcagc cgtgactggg ttggtcgcga cgcaggcaaa     3060
```

```
atcgcggcgg caatcggcct taaagttccg caagaaacgc gcctgctgtt tgtggaaacc    3120
accgcagaac atccgtttgc cgtgactgaa ctgatgatgc cggtgttgcc cgtcgtgcgc    3180
gtcgccaacg tggcggatgc cattgcgcta gcggtgaaac tggaaggcgg ttgccaccac    3240
acggcggcaa tgcactcgcg caacatcgaa aacatgaacc agatggcgaa tgctattgat    3300
accagcattt tcgttaagaa cggaccgtgc attgccgggc tggggctggg cggggaaggc    3360
tggaccacca tgaccatcac cacgccaacc ggtgaagggg taaccagcgc gcgtacgttt    3420
gtccgtctgc gtcgctgtgt attagtcgat gcgtttcgca ttgtttaacg gttctgctta    3480
tccttacgac gtgcctgact acgcctgaac ccgatgcaaa tgagacgatc gtctattcct    3540
ggtccggttt tctctgccct ctcttctatt cactttttt atactttata taaaattata    3600
taaatgacat aactgaaacg ccacacgtcc tctcctattc gttaacgcct gtctgtagcg    3660
ctgttactga agctgcgcaa gtagtttttt caccgtatag gccctctttt tctctctctt    3720
tctttctctc ccgcgctgat ctcttcttcg aaacacagag tgcaccatac caccttttca    3780
attcatcatt tttttttat tctttttttt gatttcggtt tccttgaaat tttttgatt    3840 cggtaatctc cgaacagaag gaagaacgaa ggaaggagca cagacttaga ttggtatata    3900
tacgcatatg tagtgttgaa gaaacatgaa attgcccagt attcttaacc caactgcaca    3960
gaacaaaaac ctccaggaaa cgaagataaa tcatgtcgaa agctacatat aaggaacgtg    4020
ctgctactca tcctagtcct gttgctgcca agctatttaa tatcatgcac gaaaagcaaa    4080
caaacttgtg tgcttcattg gatgttcgta ccaccaagga attactggag ttagttgaag    4140
cattaggtcc caaaatttgt ttactaaaaa cacatgtgga tatcttgact gattttccca    4200
tggagggcac agttaagccg ctaaaggcat tatccgccaa gtacaatttt ttactcttcg    4260
aagacagaaa atttgctgac attggtaata cagtcaaatt gcagtactct gcgggtgtat    4320
acagaatagc agaatgggca gacattacga atgcacacgg tgtggtgggc ccaggtattg    4380
ttagcggttt gaagcaggcg gcagaagaag taacaaagga acctagaggc cttttgatgt    4440
tagcagaatt gtcatgcaag ggctccctat ctactggaga atatactaag ggtactgttg    4500
acattgcgaa gagcgacaaa gattttgtta tcggctttat tgctcaaaga gacatgggtg    4560
gaagagatga aggttacgat tggttgatta tgacacccgg tgtgggttta gatgacaagg    4620
gagacgcatt gggtcaacag tatagaaccg tggatgatgt ggtctctaca ggatctgaca    4680
ttattattgt tggaagagga ctatttgcaa agggaaggga tgctaaggta gagggtgaac    4740
gttacagaaa agcaggctgg gaagcatatt tgagaagatg cggccagcaa aactaatcat    4800
gtaattagtt atgtcacgct tacattcacg ccctcccccc acatccgctc taaccgaaaa    4860
ggaaggagtt agacaacctg aagtctaggt ccctatttat tttttttatag ttatgttagt    4920 attaagaacg ttatttatat ttcaaatttt tctttttttt ctgtacagac gcgtgtacgc    4980
atgtaacatt atactgaaaa ccttgcttga aaggttttg ggacgctcga aggctttaat    5040
ttgcgtctgt agcgctgtta ctgaagctgc gcaagtagtt ttttcaccgt ataggccctc    5100
tttttctctc tctttcttc tctcccgcgc tgatctcttc ttcgaaacat catgaataaa    5160
aagaaaaagg aaatcaagaa aaaaaagcca taatttatcc cacattttt tttattgtcg    5220 ctgttcacac cgcataacga agatattggc tagctaacca gcttttgttc cctttagtga    5280
gggttaattt cgagcttggc gtaatcatgg tcatagctgt ttcctgtgtg aaattgttat    5340
ccgctcacaa ttccacacaa catacgagcc ggaagcataa agtgtaaagc ctggggtgcc    5400
taatgagtga gctaactcac attaattgcg ttgcgctcac tgcccgcttt ccagtcggga    5460
```

```
aacctgtcgt gccagctgca ttaatgaatc ggccaacgcg cggggagagg cggtttgcgt    5520
attgggcgct cttccgcttc ctcgctcact gactcgctgc gctcggtcgt tcggctgcgg    5580
cgagcggtat cagctcactc aaaggcggta atacggttat ccacagaatc agggggataac   5640 gcaggaaaga acatgtgagc aaaaggccag caaaaggcca ggaaccgtaa aaaggccgcg    5700
ttgctggcgt ttttccatag gctccgcccc cctgacgagc atcacaaaaa tcgacgctca    5760
agtcagaggt ggcgaaaccc gacaggacta taaagatacc aggcgtttcc ccctggaagc    5820
tccctcgtgc gctctcctgt tccgaccctg ccgcttaccg gatacctgtc cgcctttctc    5880
ccttcgggaa gcgtggcgct ttctcatagc tcacgctgta ggtatctcag ttcggtgtag    5940
gtcgttcgct ccaagctggg ctgtgtgcac gaaccccccg ttcagcccga ccgctgcgcc    6000
ttatccggta actatcgtct tgagtccaac ccggtaagac acgacttatc gccactggca    6060
gcagccactg gtaacaggat tagcagagcg aggtatgtag gcggtgctac agagttcttg    6120
aagtggtggc ctaactacgg ctacactaga aggacagtat ttggtatctg cgctctgctg    6180
aagccagtta ccttcggaaa aagagttggt agctcttgat ccggcaaaca aaccaccgct    6240
ggtagcggtg gttttttgt ttgcaagcag cagattacgc gcagaaaaaa aggatctcaa    6300
gaagatcctt tgatctttc tacggggtct gacgctcagt ggaacgaaaa ctcacgttaa    6360
gggattttgg tcatgagatt atcaaaaagg atcttcacct agatcctttt aaattaaaaa    6420
tgaagtttta atcaatcta aagtatatat gagtaaactt ggtctgacat cagaagaact   6480
cgtcaagaag gcgatagaag gcgatgcgct gcgaatcggg agcggcgata ccgtaaagca    6540
cgaggaagcg gtcagcccat tcgccgccaa gctcttcagc aatatcacgg gtagccaacg    6600
ctatgtcctg atagcggtcc gccacaccca gccggccaca gtcgatgaat ccagaaaagc    6660 ggccatttc caccatgata ttcggcaagc aggcatcgcc atgggtcacg acgagatcct    6720
cgccgtcggg catgctcgcc ttgagcctgg cgaacagttc ggctggcgcg agccctgat    6780 gctcttcgtc cagatcatcc tgatcgacaa gaccggcttc catccgagta cgtgctcgct    6840
cgatgcgatg tttcgcttgg tggtcgaatg ggcaggtagc cggatcaagc gtatgcagcc    6900
gccgcattgc atcagccatg atggatactt tctcggcagg agcaaggtga gatgacagga    6960
gatcctgccc cggcacttcg cccaatagca gccagtccct tcccgcttca gtgacaacgt    7020
cgagcacagc tgcgcaagga acgcccgtcg tggccagcca cgatagccgc gctgcctcgt    7080
cttgcagttc attcagggca ccggacaggt cggtcttgac aaaaagaacc gggcgcccct    7140
gcgctgacag ccggaacacg gcggcatcag agcagccgat tgtctgttgt gcccagtcat    7200
agccgaatag cctctccacc caagcggccg gagaacctgc gtgcaatcca tcttgttcaa    7260
ttcgagtgca ttcaacatca gccatactct cctttttca atattattga agcatttatc    7320
agggttattg tctcatgagc ggatacatat ttgaatgtat ttagaaaaat aaacaaatag    7380
gggttccgcg cacatttccc cgaaaagtgc cac                                7413
```

<210> SEQ ID NO 77  
<211> LENGTH: 59  
<212> TYPE: DNA  
<213> ORGANISM: Artificial Sequence  
<220> FEATURE:  
<223> OTHER INFORMATION: primer

<400> SEQUENCE: 77

```
aatcttgtgc tattgcagtc ctctttata tacagtataa tacgactcac tatagggcg       59
```

<210> SEQ ID NO 78
<211> LENGTH: 60
<212> TYPE: DNA
<213> ORGANISM: Artificial Sequence
<220> FEATURE:
<223> OTHER INFORMATION: primer

<400> SEQUENCE: 78
atgcgaattg cgtaattcac ggcgataacg tagtattaat taaccctcac taaagggaac    60

<210> SEQ ID NO 79
<211> LENGTH: 19
<212> TYPE: DNA
<213> ORGANISM: Artificial Sequence
<220> FEATURE:
<223> OTHER INFORMATION: primer

<400> SEQUENCE: 79
gcccacaact tatcaagtg                                                 19

<210> SEQ ID NO 80
<211> LENGTH: 19
<212> TYPE: DNA
<213> ORGANISM: Artificial Sequence
<220> FEATURE:
<223> OTHER INFORMATION: primer

<400> SEQUENCE: 80
ttataagaca agcgcaggg                                                 19

<210> SEQ ID NO 81
<211> LENGTH: 70
<212> TYPE: DNA
<213> ORGANISM: Artificial Sequence
<220> FEATURE:
<223> OTHER INFORMATION: Primer

<400> SEQUENCE: 81
atgttcaata gaagtaacac cgcaggcgga tctcaggcta tgaaagaggg ccagtcacga    60
cgttgtaaaa                                                           70

<210> SEQ ID NO 82
<211> LENGTH: 70
<212> TYPE: DNA
<213> ORGANISM: Artificial Sequence
<220> FEATURE:
<223> OTHER INFORMATION: Primer

<400> SEQUENCE: 82
tcagtgcgtt tcatcagaat cgctcaatat agtatgctct tcatcttctt aggtttcccg    60
actggaaagc                                                           70

<210> SEQ ID NO 83
<211> LENGTH: 25
<212> TYPE: DNA
<213> ORGANISM: Artificial Sequence
<220> FEATURE:
<223> OTHER INFORMATION: Primer

<400> SEQUENCE: 83
atgttcaata gaagtaacac cgcag                                          25

<210> SEQ ID NO 84
<211> LENGTH: 25

```
<210> SEQ ID NO 85
<211> LENGTH: 70
<212> TYPE: DNA
<213> ORGANISM: Artificial Sequence
<220> FEATURE:
<223> OTHER INFORMATION: Primer

<400> SEQUENCE: 84
tcagtgcgtt tcatcagaat cgctc                                          25

<210> SEQ ID NO 85
<211> LENGTH: 70
<212> TYPE: DNA
<213> ORGANISM: Artificial Sequence
<220> FEATURE:
<223> OTHER INFORMATION: Primer

<400> SEQUENCE: 85
atgtcagagg atctttcacc tacaagcagc agggtggatt tgagcaatcc ccagtcacga    60
cgttgtaaaa                                                           70

<210> SEQ ID NO 86
<211> LENGTH: 70
<212> TYPE: DNA
<213> ORGANISM: Artificial Sequence
<220> FEATURE:
<223> OTHER INFORMATION: Primer

<400> SEQUENCE: 86
tcatttattt ggagatcttg gtggaggtcc acttgagata cttccttgtc aggtttcccg    60
actggaaagc                                                           70

<210> SEQ ID NO 87
<211> LENGTH: 25
<212> TYPE: DNA
<213> ORGANISM: Artificial Sequence
<220> FEATURE:
<223> OTHER INFORMATION: Primer

<400> SEQUENCE: 87
atgtcagagg atctttcacc tacaa                                          25

<210> SEQ ID NO 88
<211> LENGTH: 25
<212> TYPE: DNA
<213> ORGANISM: Artificial Sequence
<220> FEATURE:
<223> OTHER INFORMATION: Primer

<400> SEQUENCE: 88
tcatttattt ggagatcttg gtgga                                          25
```